(12) United States Patent
Hu et al.

(10) Patent No.: US 12,379,376 B2
(45) Date of Patent: Aug. 5, 2025

(54) BIOSENSOR AND METHOD FOR DETECTION OF ANALYTES

(71) Applicant: UNIVERSITY OF NOTRE DAME DU LAC, Notre Dame, IN (US)

(72) Inventors: Jiayun Hu, Notre Dame, IN (US); Paul W. Bohn, Notre Dame, IN (US); Marvin J. Miller, South Bend, IN (US); Manuka Ghosh, Granger, IN (US)

(73) Assignee: UNIVERSITY OF NOTRE DAME DU LAC, Notre Dame, IN (US)

( * ) Notice: Subject to any disclaimer, the term of this patent is extended or adjusted under 35 U.S.C. 154(b) by 1107 days.

(21) Appl. No.: 17/297,385

(22) PCT Filed: Dec. 20, 2018

(86) PCT No.: PCT/US2018/066884
§ 371 (c)(1),
(2) Date: May 26, 2021

(87) PCT Pub. No.: WO2020/117282
PCT Pub. Date: Jun. 11, 2020

(65) Prior Publication Data
US 2022/0011304 A1 Jan. 13, 2022

Related U.S. Application Data

(60) Provisional application No. 62/774,542, filed on Dec. 3, 2018.

(51) Int. Cl.
*G01N 33/543* (2006.01)
*C12N 15/115* (2010.01)
(Continued)

(52) U.S. Cl.
CPC ..... *G01N 33/54373* (2013.01); *C12N 15/115* (2013.01); *G01N 21/658* (2013.01);
(Continued)

(58) Field of Classification Search
CPC ....... G01N 33/54373; G01N 33/54346; G01N 21/658; G01N 33/5308; G01N 33/553;
(Continued)

(56) References Cited

U.S. PATENT DOCUMENTS 3,668,148 A 6/1972 Van Beek et al.
4,123,389 A 10/1978 Pieters et al.
(Continued)

FOREIGN PATENT DOCUMENTS

CN 1939587 A 4/2007
JP H08243395 A 9/1996
(Continued)

OTHER PUBLICATIONS

Hu et al., Anal. Chem. Feb. 6, 2018 vol. 90 No. 3 pp. 2326-2332. (Year: 2018).*
(Continued)

*Primary Examiner* — Jana A Hines
(74) *Attorney, Agent, or Firm* — Michael Best & Friedrich LLP

(57) ABSTRACT

Described is a biosensor for detection of analytes and methods of using the same for detecting bacterial infection in a subject. The biosensor comprises an array of gold nanoparticles, biotinylated polyethylene glycol thiol, polyethylene glycol thiol, at least one neutravidin molecule, and at least one affinity reagent immobilized on a surface of the at least one neutravidin molecule. The affinity reagent may be an aptamer or a siderophore. The biosensors demonstrate (Continued)

extraordinary selectively and sensitivity for rapid detection of whole-cell bacteria.

18 Claims, 28 Drawing Sheets

Specification includes a Sequence Listing.

(51) Int. Cl.
 *G01N 21/65* (2006.01)
 *G01N 33/569* (2006.01)
(52) U.S. Cl.
 CPC .... *G01N 33/56911* (2013.01); *C12N 2310/16* (2013.01); *G01N 2333/21* (2013.01); *G01N 2333/22* (2013.01); *G01N 2800/26* (2013.01)
(58) Field of Classification Search
 CPC ......... G01N 33/56911; G01N 2333/21; G01N 2333/22; G01N 2800/26; C12Q 1/6806; C12N 15/115; C12N 2310/16; B82Y 30/00
 See application file for complete search history.

(56) References Cited

U.S. PATENT DOCUMENTS

| | | | |
|---|---|---|---|
| 4,632,916 A | 12/1986 | Bither, Jr. | |
| 5,358,631 A | 10/1994 | Miller et al. | |
| 5,463,096 A | 10/1995 | Lok | |
| 5,928,983 A | 7/1999 | Culross | |
| 5,977,192 A | 11/1999 | Howsmom et al. | |
| 6,413,449 B1 | 7/2002 | Wieland et al. | |
| 6,964,757 B2 | 11/2005 | Cortright et al. | |
| 7,578,986 B2 | 8/2009 | Hampden-Smith et al. | |
| 7,618,612 B2 | 11/2009 | Cortright et al. | |
| 7,906,559 B2 | 3/2011 | Olah et al. | |
| 8,137,942 B2 * | 3/2012 | Roitman .......... | G01N 33/54393 435/6.12 |
| 9,346,748 B2 | 5/2016 | Wada et al. | |
| 2005/0112056 A1 | 5/2005 | Hampden-Smith et al. | |
| 2006/0099483 A1 | 5/2006 | Min et al. | |
| 2016/0319322 A1 * | 11/2016 | Miller .............. | G01N 33/54387 |

FOREIGN PATENT DOCUMENTS

| | | | |
|---|---|---|---|
| KR | 101218660 B1 | 1/2013 | |
| WO | WO1986006063 A1 | 10/1986 | |
| WO | WO1999002265 A1 | 1/1999 | |
| WO | WO2008157673 A1 | 12/2008 | |
| WO | WO-2018017021 A2 * | 1/2018 | ............. G01N 21/01 |

OTHER PUBLICATIONS

Scott et al. (Bioconjug Chem. Oct. 14, 2016;28(1):203-211) Epub. Oct. 14, 2016) (Year: 2016).*
Gedi et al., (Sensors 2014, 14(10), 18302-18327). (Year: 2014).*
Oh, S.Y., et al., (Sci Rep 7, 10130. Aug. 31, 2017) (Year: 2017).*
Wencewicz et al., (J Med Chem. May 23, 2013;56(10):4044-52). (Year: 2013).*
Abadeer et al., "Interactions of Bacterial Lipopolysaccharides with Gold Nanorod Surfaces Investigated by Refractometric Sensing", ACS Appl. Mater. Interfaces, 2015, 7(44), pp. 24915-24925.
Ahmed et al., "Biosensors for Whole-Cell Bacterial Detections", Clinical Microbiology Reviews, vol. 27, No. 3, 2014, pp. 631-646.
Bai et al., "A SPR Aptasensor for Detection of Avian Influenza Virus H5N1", Sensors, vol. 12, 2012, pp. 12506-12518.
Baig et al., "Gold nanoparticle-based colorimetric sensing of dipicolinic acid from complex samples", Anal. Bioanal. Chem., 2018, 410(6), pp. 1805-1815.
Campuzano et al., "Bacterial Isolation by Lectin-Modified Microengines", Nano Lett., 2012, 12(1), pp. 396-401.
Chang et al., "Rapid single cell detection of *Staphylococcus aureus* by aptamer-conjugated gold nanoparticles", Sci. Rep., 2013, vol. 3, No. 1863, pp. 1-7.
Doorneweerd et al., "Selective Capture and Identification of Pathogenic Bacteria Using an Immobilized Siderophore", Langmuir, 2010, 26(19), pp. 15424-15429.
Edgar et al., "High-sensitivity bacterial detection using biotin-tagged phage and quantum-dot nanocomplexes", PNAS, 2006, 103(13), pp. 4841-4845.
Frolov et al., "Direct Observation of Aminoglycoside-RNA Binding by Localized Surface Plasmon Resonance Spectroscopy", Anal. Chem., 2013, 85(4), pp. 2200-2207.
Fu et al., "Limitation of a localized surface plasmon resonance sensor for *Salmonella* detection", Sens. Actuator B-Chem., 2009, 141(1), pp. 276-283.
Gao et al., "Screening Lectin-Binding Specificity of Bacterium by Lectin Microarray with Gold Nanoparticle Probes", Anal. Chem., 82(22), 2010, pp. 9240-9247.
Ghosh et al., "Targeted Antibiotic Delivery: Selective Siderophore Conjugation with Daptomycin Confers Potent Activity against Multidrug Resistant Acinetobacter baumannii Both in Vitro and in Vivo", J. Med. Chem., 2017, 60(11), pp. 4577-4583.
Haber et al., "Rapid real-time recirculating PCR using localized surface plasmon resonance (LSPR) and piezo-electric pumping", Lab Chip, 2017, 17(16), pp. 2821-2830.
Haes et al., "Preliminary studies and potential applications of localized surface plasmon resonance spectroscopy in medical diagnostics", Expert Rev. Mol. Diagn., 2004, 4(4), pp. 527-537.
Hider et al., "Chemistry and biology of siderophores", Nat. Prod. Rep., 2010, 27(5), pp. 637-657.
Hiller et al., "Biotin binding to avidin. Oligosaccharide side chain not required for ligand association", Biochem. J., 1987, 248(1), pp. 167-171.
Hiller et al., "Nonglycosylated avidin", Methods in Enzymology, Academic Press, 1990, pp. 68-70.
Hong et al., "Single-Stranded DNA Aptamers against Pathogens and Toxins: Identification and Biosensing Applications", BioMed Research International, 2015, 31 pages.
Hu et al., "Optical Biosensing of Bacteria and Bacterial Communities", J. Anal. Test., 2017, 1(1), p. 4.
Hu et al., "Whole-Cell Pseudomonas aeruginosa Localized Surface Plasmon Resonance Aptasensor", Anal. Chem., vol. 90, 2018, pp. 2326-2332.
Hulteen et al., "Nanosphere lithography: a materials general fabrication process for periodic particle array surfaces", J. Vac. Sci. Technol., 1995, 13, pp. 1553-1558.
Inomata et al., "Adsorption and detection of *Escherichia coli* using an Au substrate modified with a catecholate-type artificial siderophore-Fe3+ complex", Dalton Trans., 2013, 42(45), pp. 16043-16048.
Inomata et al., "Adsorption Behavior of Microbes on a QCM Chip Modified with an Artificial Siderophore-Fe3+ Complex", Langmuir, 2012, 28(2), pp. 1611-1617.
International Preliminary Report on Patentability for Application No. PCT/US18/66884 dated Jun. 8, 2021 (7 pages).
International Search Report and Written Opinion for Application No. PCT/US18/66884 dated Apr. 1, 2019 (10 pages).
Kim et al., "Label-free detection of a bacterial pathogen using an immobilized siderophore, deferoxamine", Lab Chip, 2012, 12(5), pp. 971-976.
Kim et al., "Plasmonic Properties of the Multispot Copper-Capped Nanoparticle Array Chip and Its Application to Optical Biosensors for Pathogen Detection of Multiplex DNAs", Anal. Chem., 2011, 83(16), pp. 6215-6222.
Liu et al., "A Synthetic Dual Drug Sideromycin Induces Gram-Negative Bacteria To Commit Suicide with a Gram-Positive Antibiotic", Med Chem, 2018, 61(9), pp. 3845-3854.
Mayer et al., "Localized Surface Plasmon Resonance Sensors", Chem. Rev., 2011, 111(6), pp. 3828-3857.
Miethke et al., "Siderophore-Based Iron Acquisition and Pathogen Control", Microbiol. Mol. Biol. Rev., 2007, 71(3), pp. 413-451.

(56) References Cited

OTHER PUBLICATIONS

Miller et al., "Design, Synthesis, and Study of a Mycobactin-Artemisinin Conjugate That Has Selective and Potent Activity against Tuberculosis and Malaria", J. Am. Chem. Soc., 2011, 133(7), pp. 2076-2079.

Olanrewaju et al., "Microfluidic Capillaric Circuit for Rapid and Facile Bacteria Detection", Anal. Chem., 2017, 89(12), pp. 6846-6853.

Onyestyak et al., "Carboxylic Acid Reduction over Silica Supported Cu, Ni, and Cu2In Catalysts", Acta Chim. Slov, vol. 61, 2014, pp. 819-826.

Onyestyak, "Ni/silica based bimetallic catalysts by solid state co-reduction of admixed metal oxides", Res Chem Intermed, vol. 41, 2015, pp. 9207-9215.

Onyestyak, "Non-previous Metal Catalysts for Acetic Acid Reduction", Periodica Polytechnica Chemical Engineering, vol. 61, No. 4, 2017, pp. 270-277.

Pahlow et al., "Rapid Identification of *Pseudomonas* spp. via Raman Spectroscopy Using Pyoverdine as Capture Probe", Anal. Chem., 2016, 88(3), pp. 1570-1577.

Pandey et al., "Chemical synthesis of staphyloferrin A and its application for *Staphylococcus aureus* detection", Org. Biomol. Chem., 2014, 12(11), pp. 1707-1710.

Pavlyuk et al., "Peptide-Based Fluorescent Biosensing for Rapid Detection of Fuel Biocontamination", Energy Fuels, 2017, 31(4), pp. 3747-3758.

Pramanik et al., "Unraveling the Interaction of Silver Nanoparticles with Mammalian and Bacterial DNA", J. Phys. Chem. B, 2016, 120(24), pp. 5313-5324.

Sandy et al., "Microbial Iron Acquisition: Marine and Terrestrial Siderophores", Chem. Rev., 2009, 109(10), pp. 4580-4595.

Shen et al., "Rapid and Selective Detection of Pathogenic Bacteria in Bloodstream Infections with Aptamer-Based Recognition", ACS Appl. Mater. Interfaces, 2016, 8(30), pp. 19371-19378.

Shiigi et al., "Nanoantennas as Biomarkers for Bacterial Detection", Anal. Chem., 2015, 87(7), pp. 4042-4046.

Shin et al., "Aptamer-Based Paper Strip Sensor for Detecting Vibrio fischeri", ACS Comb. Sci., 2018, 20(5), pp. 261-268.

Urmann et al., "Whole-cell detection of live lactobacillus acidophilus on aptamer-decorated porous silicon biosensors", Analyst, 2016, 141(18), pp. 5432-5440.

Wang et al., "Utility of aptamer-fluorescence in situ hybridization for rapid detection of Pseudomonas aeruginosa", Eur. J. Clin. Microbiol. Infect. Dis., 2011, 30(2), pp. 273-278.

Wayment et al., "Biotin-avidin binding kinetics measured by single-molecule imaging", Anal Chem, 2009, 81(1), pp. 336-342.

Wencewicz et al., "Biscatecholate-Monohydroxamate Mixed Ligand Siderophore-Carbacephalosporin Conjugates are Selective Sideromycin Antibiotics That Target Acinetobacter baumannii", J. Med. Chem., vol. 56, 2013, pp. 4044-4052.

Wencewicz et al., "Trihydroxamate Siderophore-Fluoroquinolone Conjugates Are Selective Sideromycin Antibiotics that Target *Staphylococcus aureus*", Bioconjugate Chem., 2013, 24(3), pp. 473-486.

Wilchek et al., "Introduction to avidin-biotin technology", Methods in Enzymology. Academic Press, 1990, pp. 5-13.

Willets et al., "Localized Surface Plasmon Resonance Spectroscopy and Sensing", Annu. Rev. Phys. Chem., 2007, 58(1), pp. 267-297.

Wolfenden et al., "Determination of Bacterial Viability by Selective Capture Using Surface-Bound Siderophores", Adv. Biol. Chem., 2012, 2, pp. 396-402.

Wu et al., "Quantum Dot-Ferrichrome Bioprobes for Recognition of Pseudomonas fluorescens", J. Phys. Chem. C, 2009, 113(21), 9169-9174.

Wu et al., "Trace Detection of Specific Viable Bacteria Using Tetracysteine-Tagged Bacteriophages", Anal. Chem., 2014, 86(1), pp. 907-912.

Yoo et al., "Aptamer-functionalized localized surface plasmon resonance sensor for the multiplexed detection of different bacterial species", Talanta, 2015, 132, pp. 112-117.

Zhang et al., "Janus Emulsions for the Detection of Bacteria", ACS Cent. Sci., 2017, 3(4), pp. 309-313.

Zhou et al., "Quantitative Label-Free Listeria Analysis Based On Aptamer Modified Nanoporous Sensor", ACS Sens., 2016, 1(8), pp. 965-969.

\* cited by examiner

SEQUENCE LISTING

<160> NUMBER OF SEQ ID NOS: 2

<210> SEQ ID NO 1
<211> LENGTH: 96
<212> TYPE: DNA
<213> ORGANISM: Artificial Sequence
<220> FEATURE:
<223> OTHER INFORMATION: Synthetic

<400> SEQUENCE: 1
ataccagctt attcaattcc cccgttgctt tcgcttttcc tttcgctttt gttcgtttcg    60
tccctgcttc ctttcttgag atagtaagtg caatct    96

<210> SEQ ID NO 2
<211> LENGTH: 96
<212> TYPE: DNA
<213> ORGANISM: Artificial Sequence
<220> FEATURE:
<223> OTHER INFORMATION: Synthetic

<400> SEQUENCE: 2
ataccagctt attcaattcc cccgttgctt tcgcttttcc tttcgctttt gttcgtttcg    60
tccctgcttc ctttcttgag atagtaagtg caatct    96

BIOSENSOR AND METHOD FOR DETECTION OF ANALYTES

CROSS-REFERENCE TO RELATED APPLICATION(S)

This application is a U.S. national stage entry of International Patent Application No. PCT/US2018/066884, filed on Dec. 20, 2018, which claims priority from U.S. Provisional Patent Application No. 62/774,542, filed on Dec. 3, 2018, the entire disclosures of each of which are herein incorporated by reference for all purposes.

STATEMENT OF GOVERNMENT INTEREST

This invention was made with government support under grant number AI113219 awarded by the National Institutes of Health. The government has certain rights in the invention.

TECHNICAL FIELD

The present disclosure relates to methods and devices for detection of analytes. The methods and devices disclosed herein may be used for detection of whole-cell bacteria.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 871 bytes ASCII (Text) file named "18-050-092012-9080-W001-SEQ-LIST-12-20-18.txt," created on Dec. 20, 2018.

BACKGROUND

The worldwide development of multidrug resistance in microbes not only threatens public health globally, but also carries a hefty economic burden through increasing health care costs and loss of productivity. At least three different classes of antibiotics, including carbapenems, last resort antibiotics, have failed to treat multidrug resistant bacterial infections. In 2017, the World Health Organization listed carbapenem-resistant strains of *Acinetobacter baumannii* and *Pseudomonas aeruginosa* as top priority pathogens. Gram-negative bacterial infections are particularly challenging to treat due to: (a) a thick, altered cell wall structure which significantly reduces the permeability of drugs and diminishes drug binding efficiency, (b) production of enzymes to destroy antibiotics, and (c) evolved efflux mechanisms to out-pump antibiotics. To combat the burgeoning global crisis of multidrug resistant microbes, two parallel efforts are urgently needed: new antibiotics which circumvent the evolutionary potential of microbes to evade destruction, and advanced diagnostic tools which can specifically and sensitively detect the presence of pathogenic strains of microbes, thereby avoiding the over-prescription of wide-spectrum antibiotics.

Current gold standard microbiology methods for bacterial detection require culturing bacteria in a strictly controlled laboratory environment and often take days for an accurate reading. Immunoassays, an alternative strategy, are rapid but suffer from relatively low sensitivity with a typical limit of detection (LOD) of $10^3$-$10^6$ cfu mL$^{-1}$ (cfu=colony-forming unit). Other approaches like polymerase chain reaction (PCR) and its derivatives afford fast and sensitive detection but require extensive sample preparation to extract DNA from bacteria as well as expensive reagents and instrumentation. As such, methods for bacterial detection which optimize detection speed, sensitivity, selectivity, and cost for bacterial diagnostics are needed.

SUMMARY

In one aspect, disclosed herein are biosensors for detection of analytes. The biosensors may be used for whole-cell bacterial detection. The biosensor may comprise an array of gold nanoparticles; biotinylated polyethylene glycol thiol in direct contact with one or more of the gold nanoparticles; polyethylene glycol thiol in direct contact with one or more of the gold nanoparticles; at least one neutravidin molecule immobilized on a surface of the biotinylated polyethylene glycol thiol; and at least one affinity reagent immobilized on a surface of the at least one neutravidin molecule. The affinity reagent may be a biotinylated aptamer. The affinity reagent may be a biotinylated siderophore. The disclosed biosensors may be used in a method of detecting bacterial infection in a subject. For example, the disclosed biosensors may be used in a method of detecting *Pseudomonas aeruginosa* infection or *Acinetobacter baumannii* infection in a subject.

Other aspects of the disclosure will become apparent by consideration of the detailed description and accompanying drawings.

BRIEF DESCRIPTIONS OF THE DRAWINGS

FIG. 1A is a schematic illustration of LSPR sensor chip (left) with a legend (right). FIG. 1B and FIG. 1C are representative SEM images of Au nanotriangle arrays before (FIG. 1B), and after (FIG. 1B) exposure of the sensor surface to *P. aeruginosa* strain PAO1. The cell shown was likely captured during cell division.

FIG. 2 is a graph showing representative LSPR extinction spectra of Au nanotriangle array (curve 1), the same array after Bt-PEG thiol/PEG thiol, neutravidin, and Bt-aptamer modification (curve 2), and after exposure of the modified surface to 10 cfu mL$^{-1}$ PAO1 (curve 3).

FIG. 3 is a series of box plots showing LSPR wavelength shift ($\Delta\lambda$ (nm)) as a function of bacterial concentration (cfu/mL). Each box plot represents a different bacterial concentration with 9-14 individual data points (solid diamonds are results of individual experiments). The central line of each box represents the $50^{th}$ percentile. The lower and upper boundary lines represent the $25^{th}$ and $75^{th}$ percentiles, respectively. The circle represents the mean of all data. The whisker extends to one standard deviation. Diagonal crosses (x) represent the $1^{st}$ and $99^{th}$ percentiles. Inset shows the linear range of the calibration curve, where error bar represents the standard deviation of all data points at a specific bacterial concentration. A linear fit of LSPR shift vs. log bacterial concentration gives y=6.0x+2.2 with $R^2$=0.99.

FIG. 4 is a series of box plots demonstrating LSPR wavelength shift ($\Delta\lambda$ (nm)) obtained from different bacteria employing the PAO1-specific aptamer. A bacterial load of $10^3$ cfu mL$^{-1}$ was tested in each case. Each box plot represents a different bacterial sample with 8-10 individual data points (solid diamonds are results of individual experiments). The central box line represents the $50^{th}$ percentile. The lower and upper boundary lines represent the $25^{th}$ and $75^{th}$ percentiles, respectively. The circle represents the mean of all data. The whisker extends to one standard deviation. Diagonal crosses (x) represent the $1^{st}$ and $99^{th}$ percentiles.

FIG. 5 is a graph showing LSPR wavelength stability of sensor chips stored in ambient conditions as a function of time. Groups 1, 2, and 3 represent Au nanotriangle array, Bt-PEG thiol/PEG thiol modified Au nanotriangle array, and Bt-PEG thiol/PEG thiol/neutravidin modified Au nanotriangle array, respectively. Three different sensor chips were used to test each condition.

Figure 7:
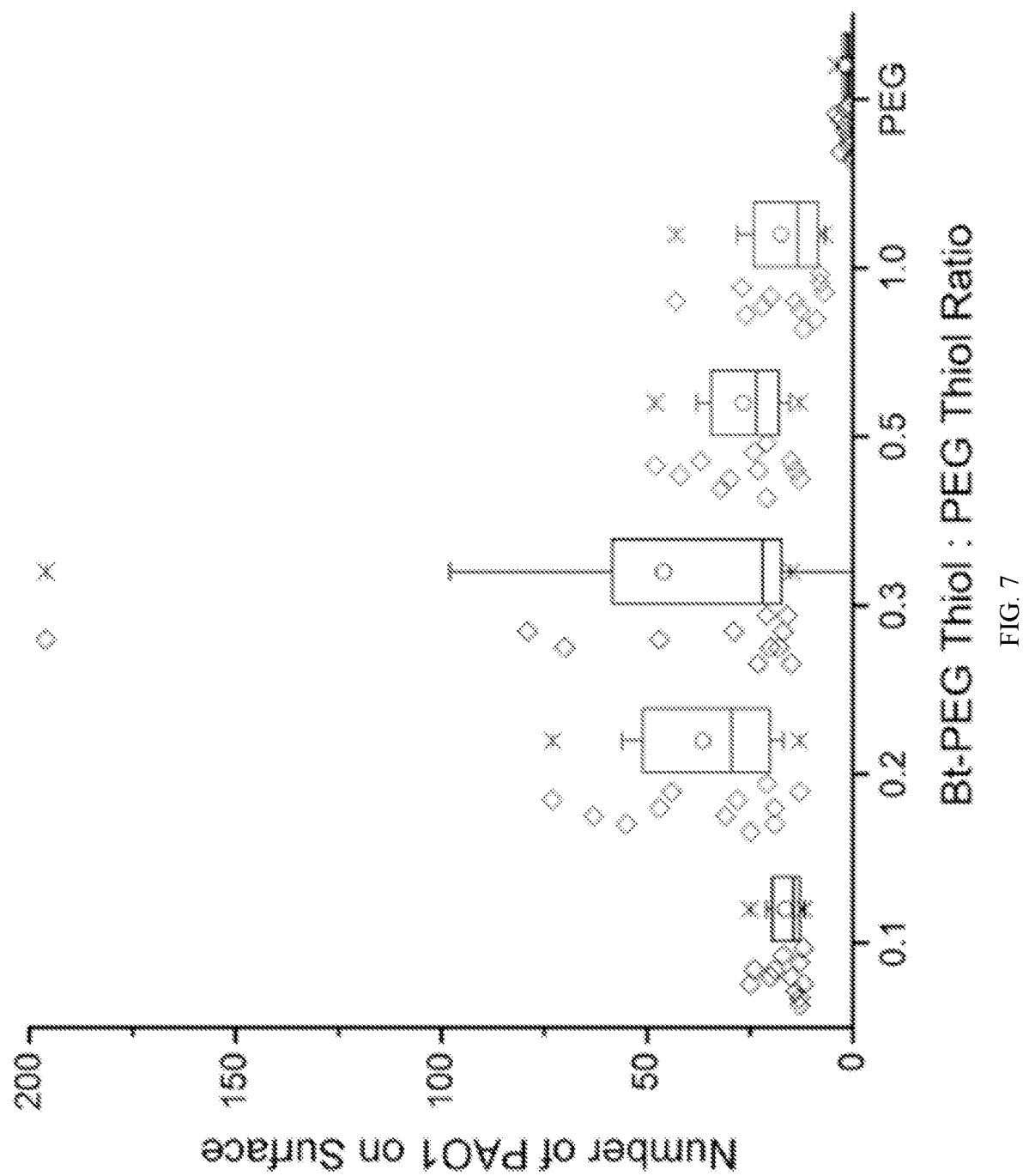

FIG. 7 is a graph showing the number of captured *P. aeruginosa* strain PAO1 cells as a function of Bt-PEG thiol:PEG thiol ratio. Each data point was collected by counting the number of bacteria in a 256 µm×256 µm area. Each color represents a different ratio of Bt-PEG thiol and PEG thiol on sensor surface with 12 individual data points (diamonds). The central box line represents $50^{th}$ percentile. The lower and upper boundary lines represent the $25^{th}$ and $75^{th}$ percentiles, respectively. The circle represents the mean of all data points. The whisker extends to one standard deviation. Diagonal crosses (x) represent the $1^{st}$ and $99^{th}$ percentiles.

Figure 8A:
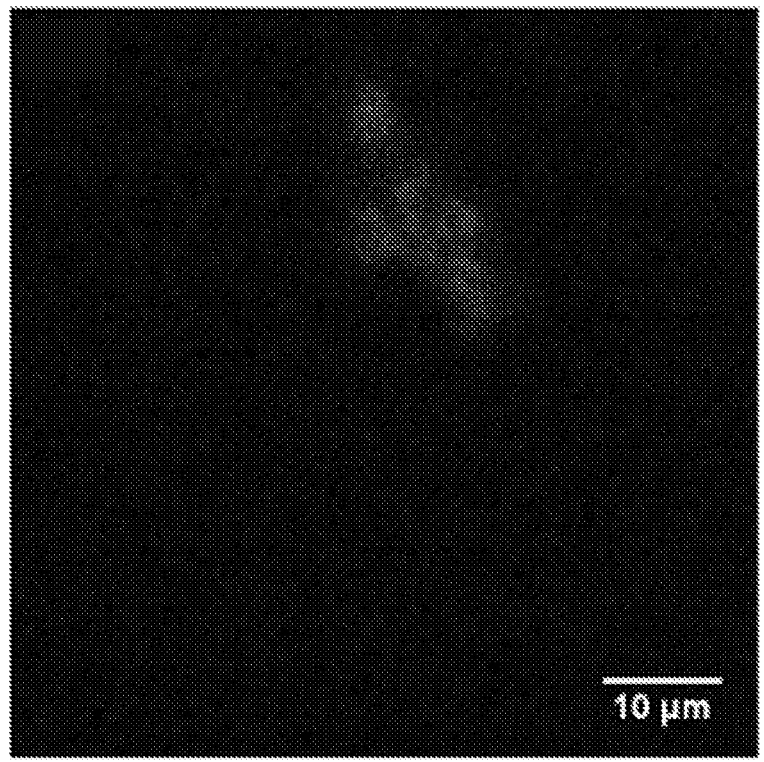
Figure 8B:
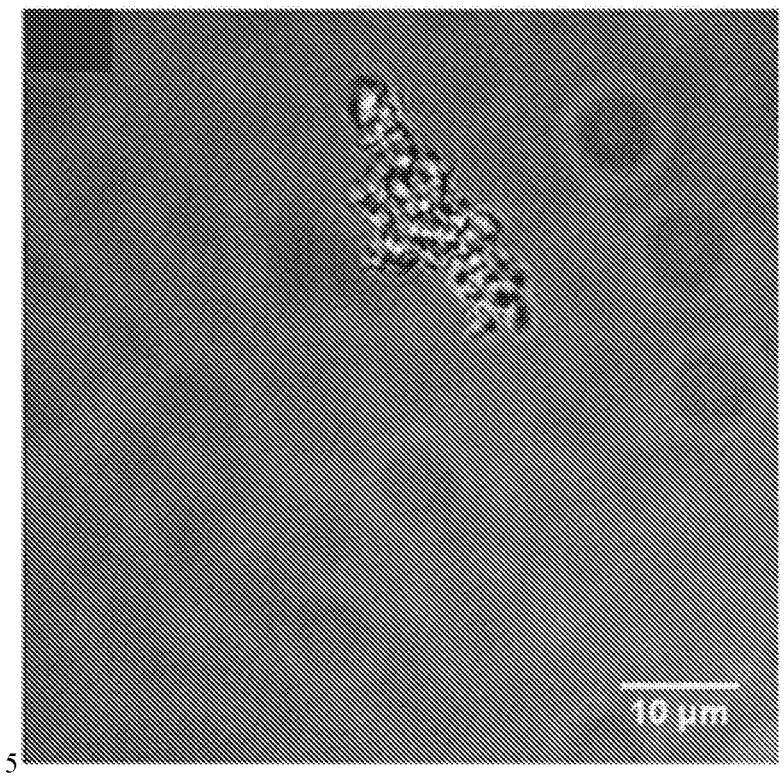

FIG. 8A and FIG. 8B are fluorescence confocal microscope images of fluorescently labeled aptamer bound to *P. aeruginosa* strain PAO1 cells in fluorescence (FIG. 8A) and a combination of fluorescence and transmission mode (FIG. 8B).

Figure 9:
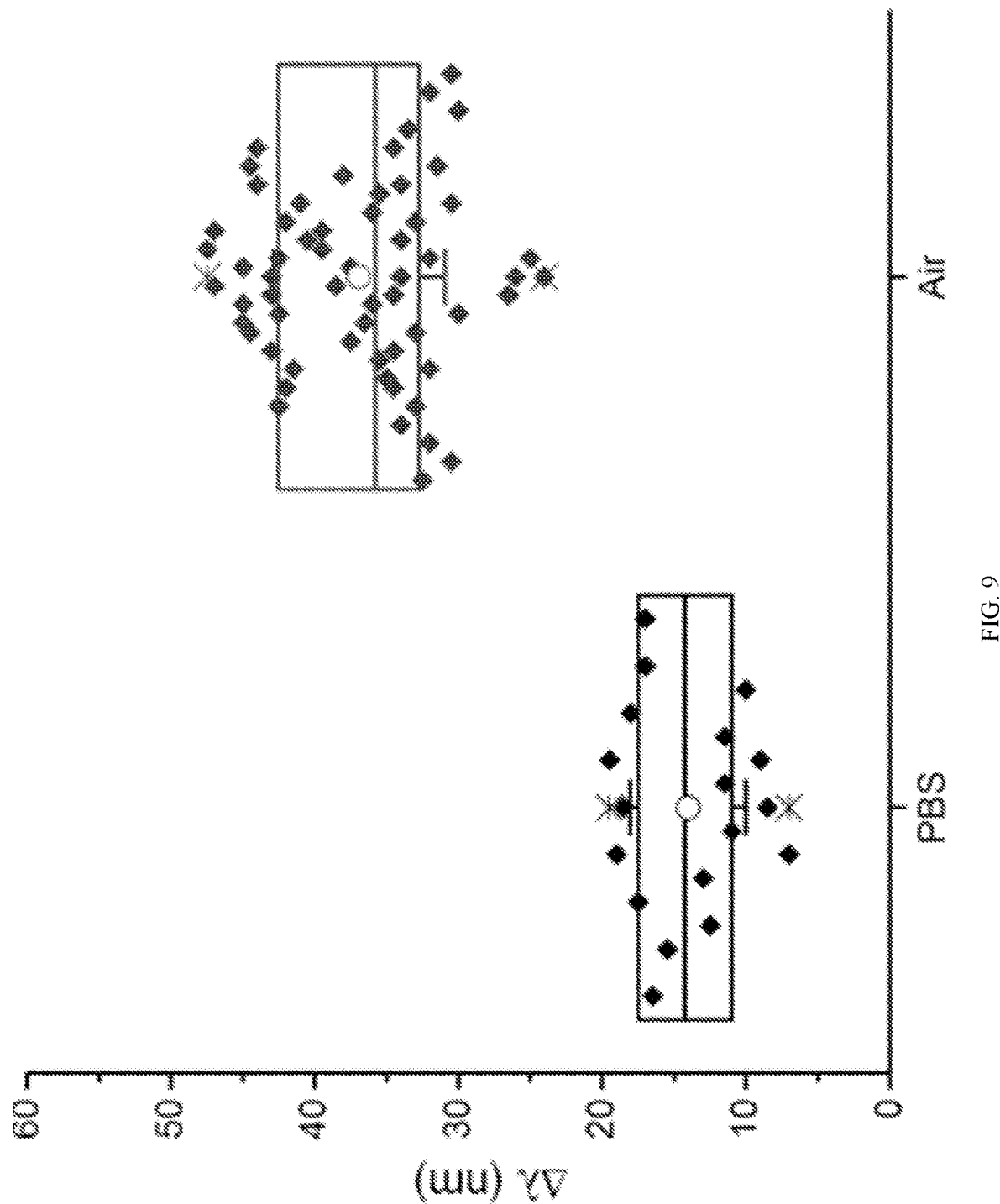

FIG. 9 is a series of box plots demonstrating the LSPR wavelength shift between a bare Au nanotriangle array and the same array after immobilization of Bt-PEG thiol/PEG thiol, neutravidin, Bt-aptamer measured in PBS solution and air. The solid diamonds represent individual data points. The central box line represents $50^{th}$ percentile. The lower and upper boundary lines represent the $25^{th}$ and $75^{th}$ percentiles, respectively. The circle represents the mean of all data points. The whisker extends to one standard deviation. Diagonal crosses (x) represent the $1^{st}$ and $99^{th}$ percentiles.

Figure 10:
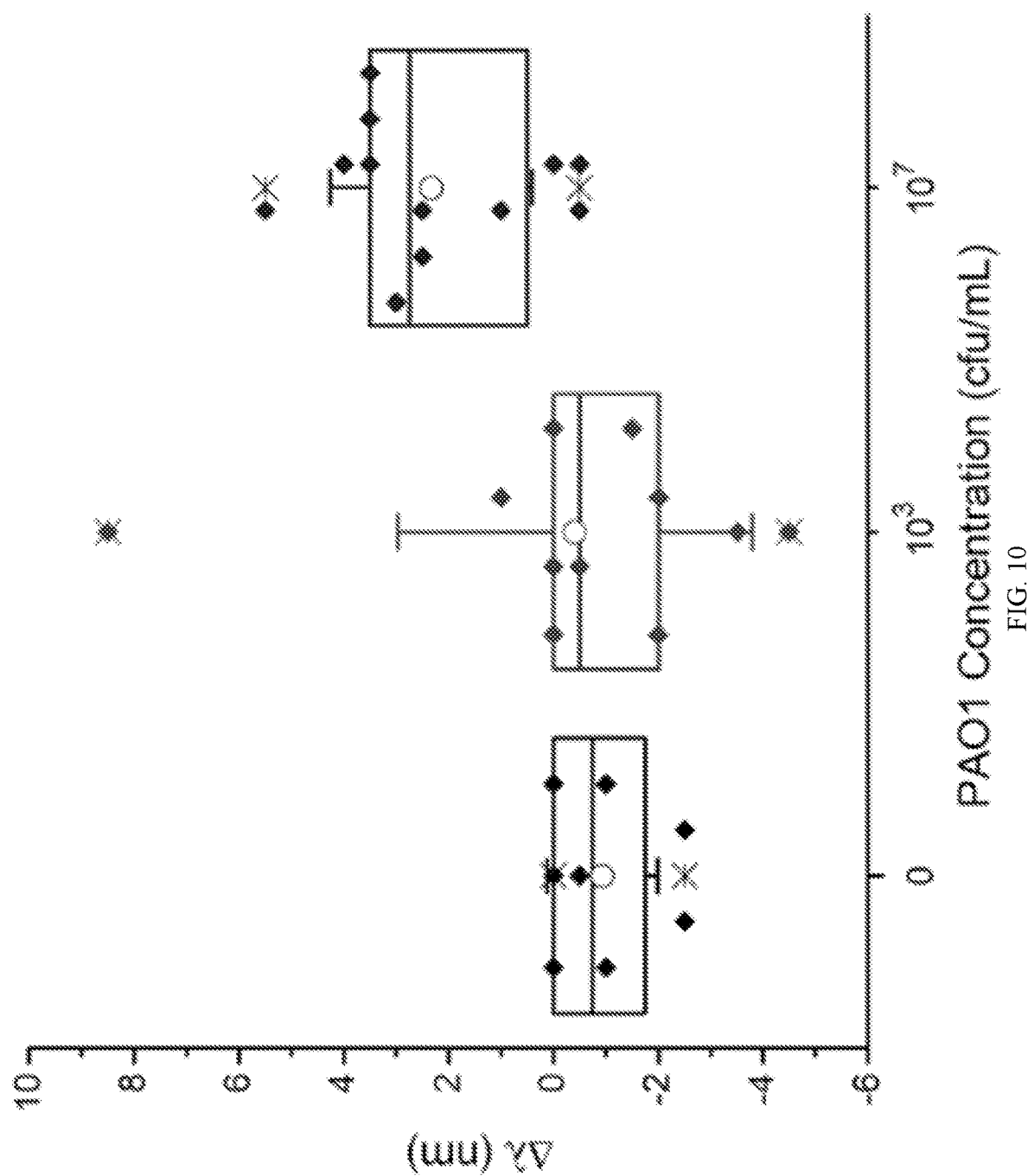

FIG. 10 is a series of box plots representing the LSPR wavelength shift as a function of PAO1 concentration measured in PBS solution. The solid diamonds represent individual data points. The central box line represents $50^{th}$ percentile. The lower and upper boundary lines represent the $25^{th}$ and $75^{th}$ percentiles, respectively. The circle represents the mean of all data points. The whisker extends to one standard deviation. Diagonal crosses (x) represent the $1^4$ and $99^{th}$ percentiles.

Figure 11:
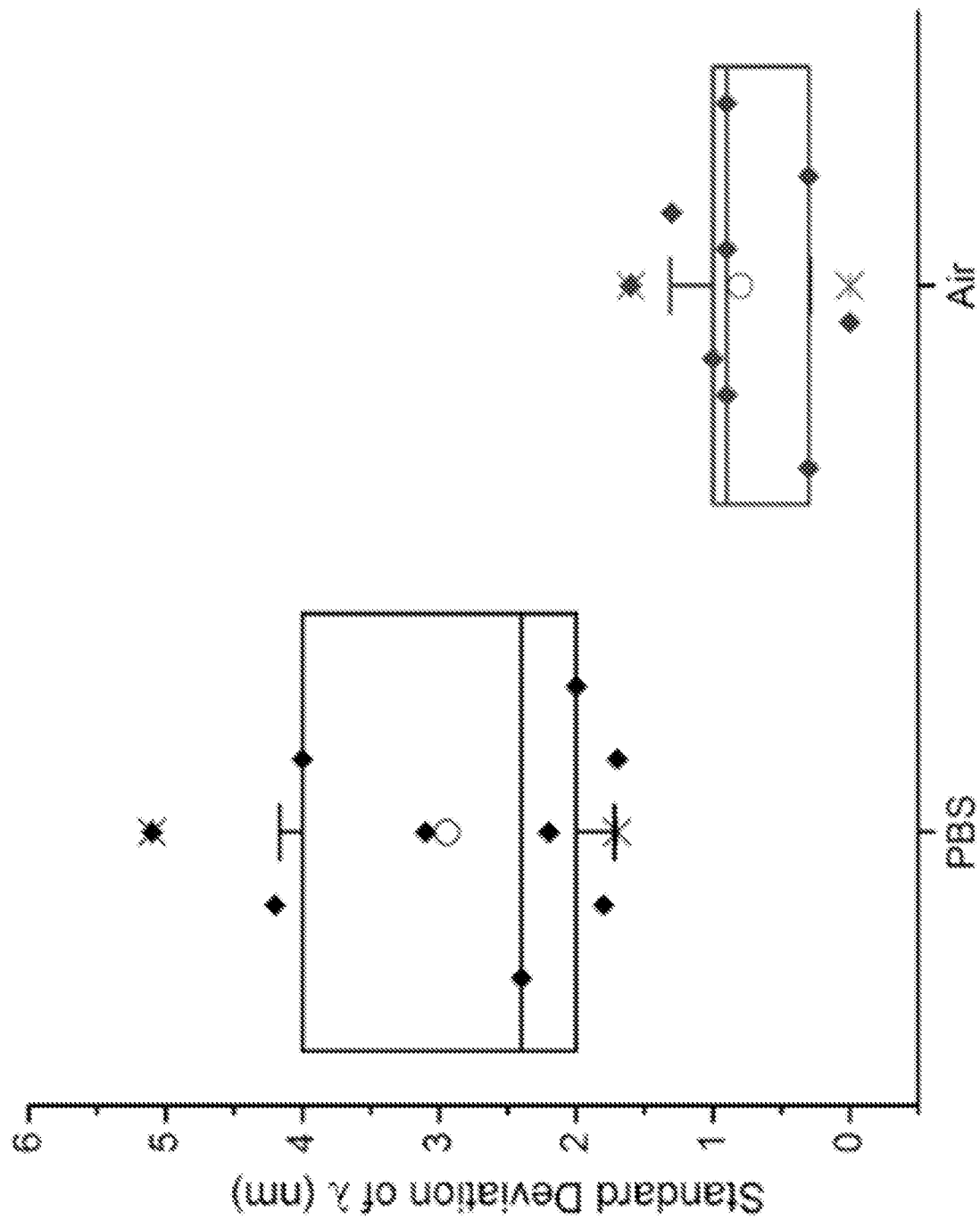

FIG. 11 is a series of box plots showing the standard deviation of LSPR wavelength measurements of Au nanotriangles carried out in PBS solution and air. The solid diamonds represent individual data points. Each data point represents the standard deviation of three consecutive measurements of each sensor chip. The central box line represents $50^{th}$ percentile. The lower and upper boundary lines represent the $25^{th}$ and $75^{th}$ percentiles, respectively. The circle represents the mean of all data points. The whisker extends to one standard deviation. Diagonal crosses (x) represent the $1^{st}$ and $99^{th}$ percentiles.

Figure 12A:
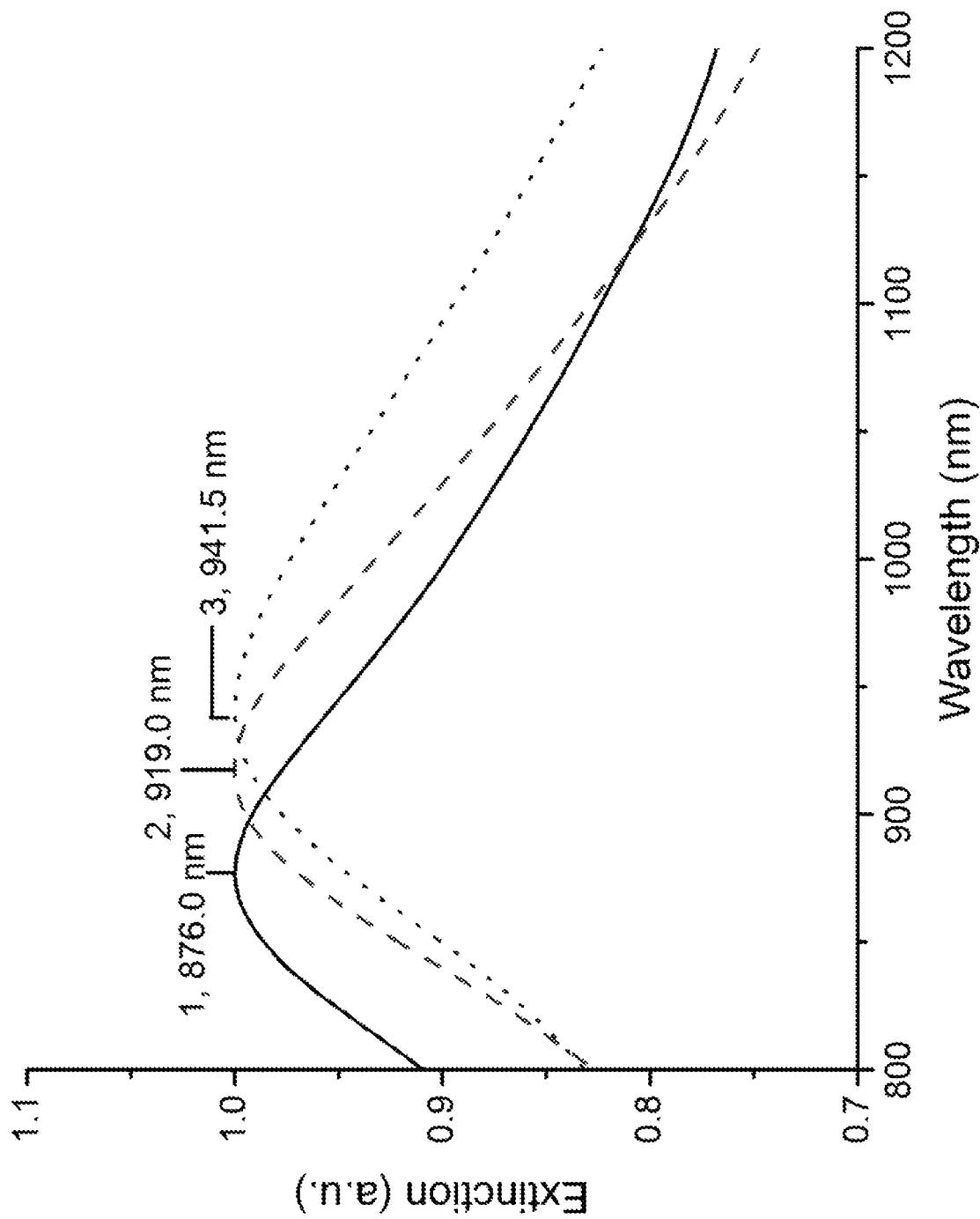
Figure 12B:
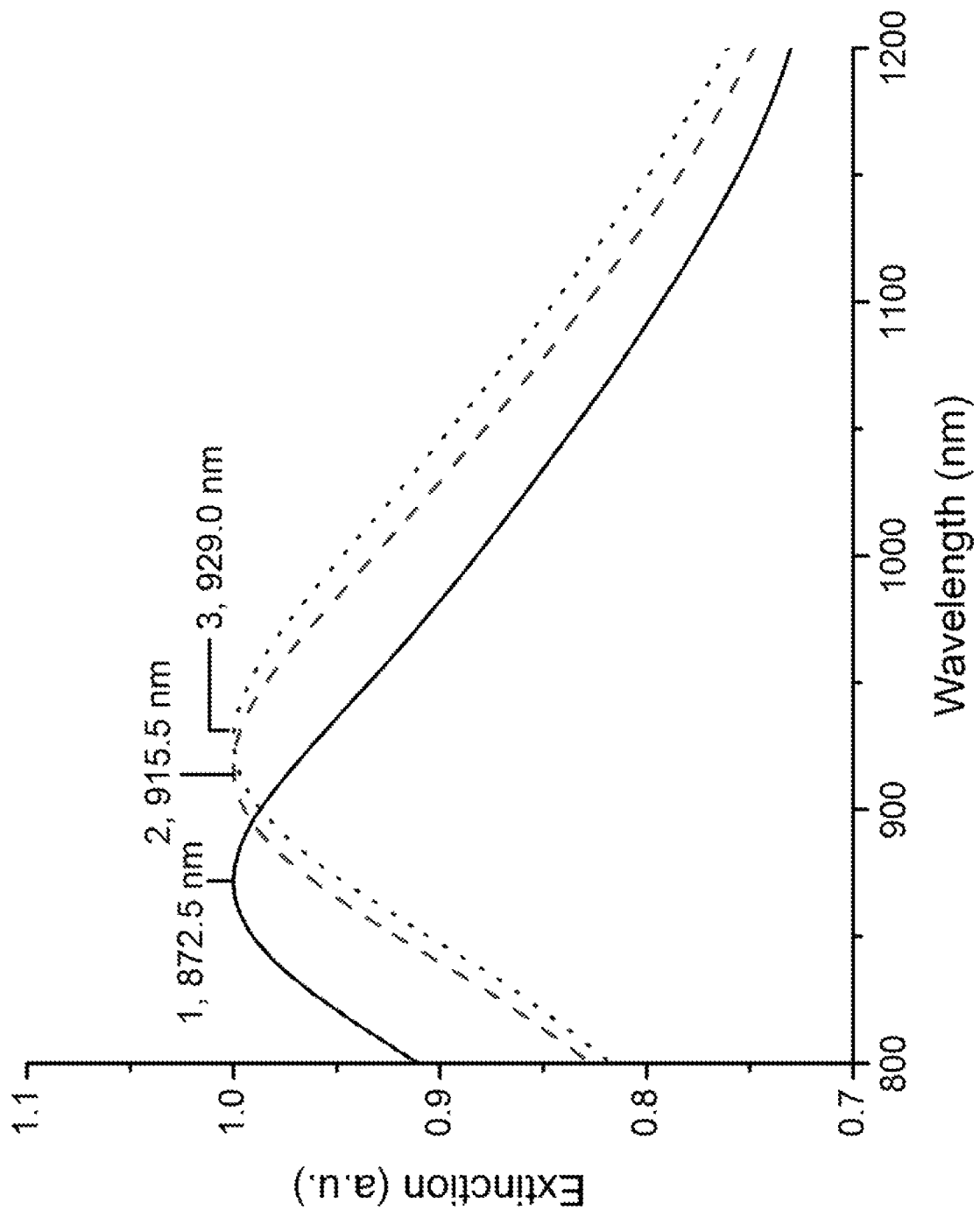
Figure 12C:
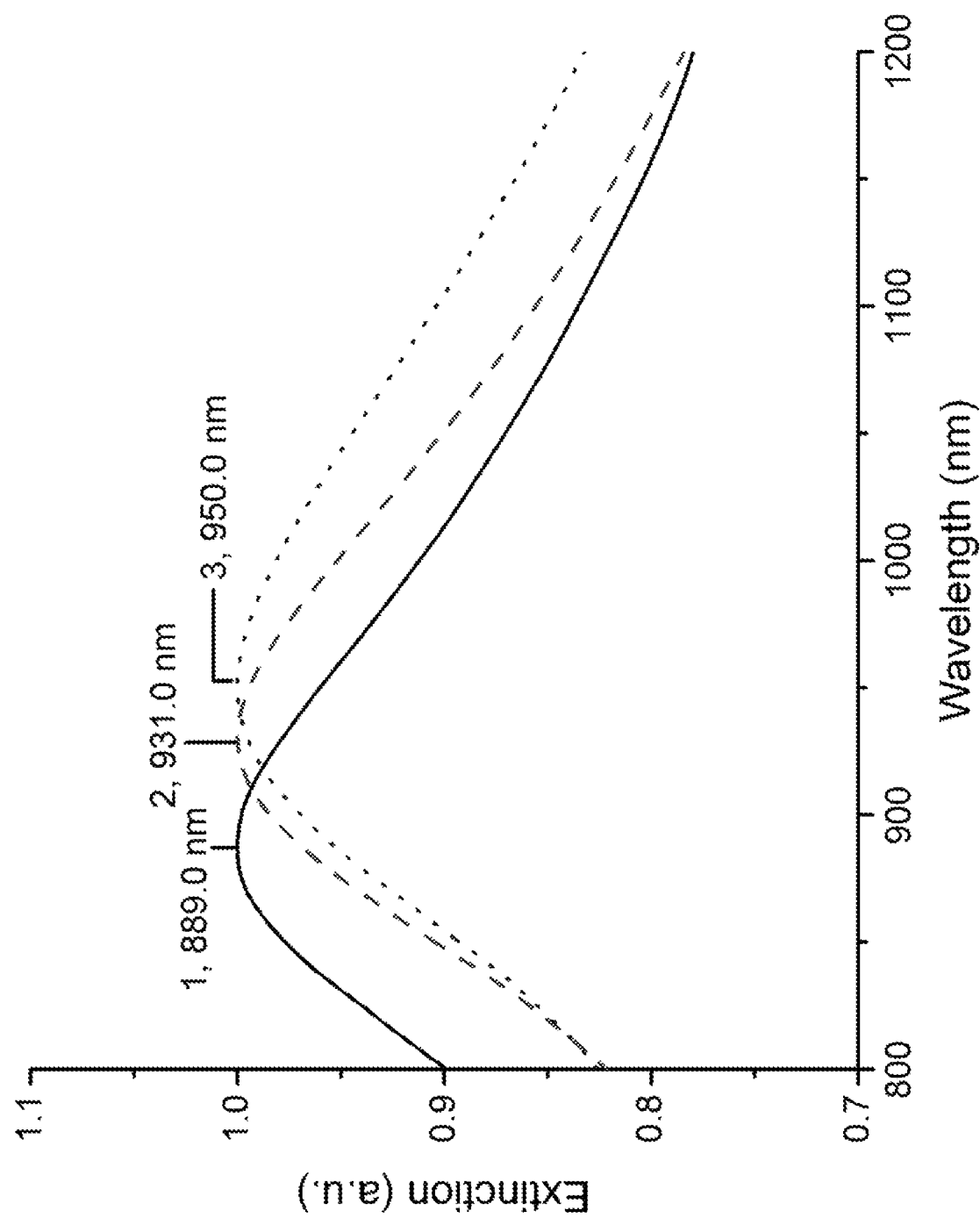

FIG. 12A, FIG. 12B, and FIG. 12C are graphs showing, respectively, representative LSPR spectra of three different sensor chips and their responses to surface modifications as well as bacterial attachment. LSPR extinction spectra of Au nanotriangle array (curve 1), Bt-PEG thiol/PEG thiol, neutravidin, and Bt-aptamer modified sensor surface (curve 2), and modified surface after exposure to $10^3$ cfu mL$^{-1}$ PAO1 (curve 3).

Figure 13A:
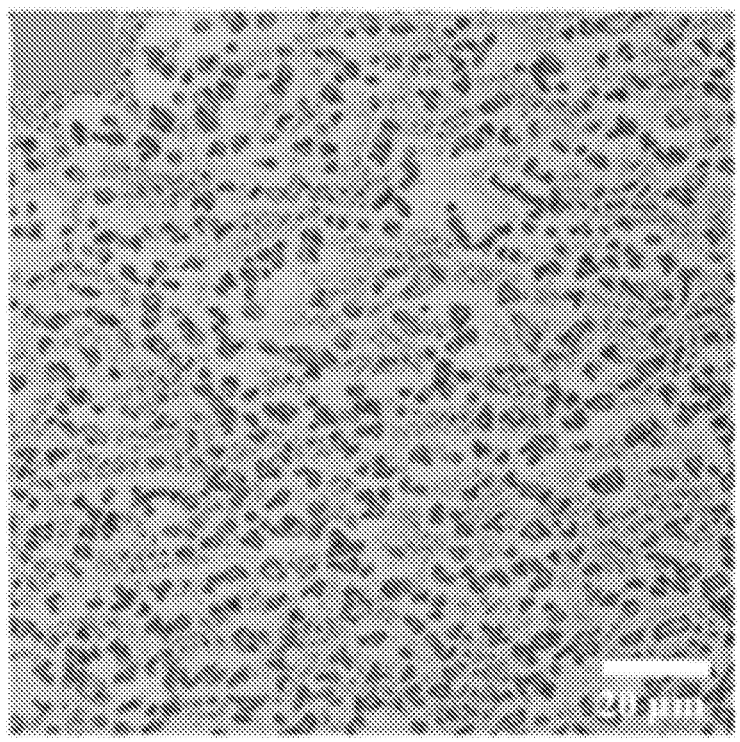
Figure 13B:
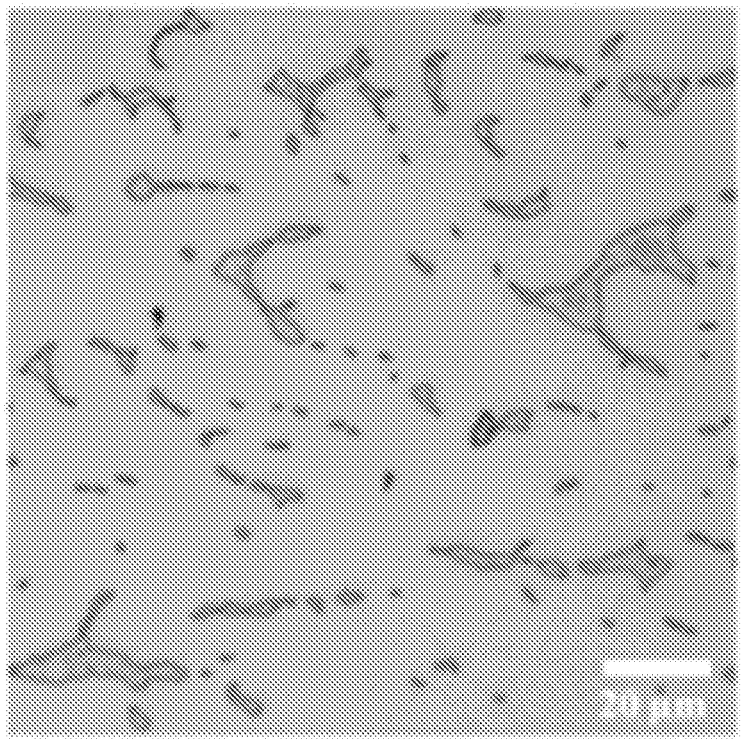
Figure 13C:
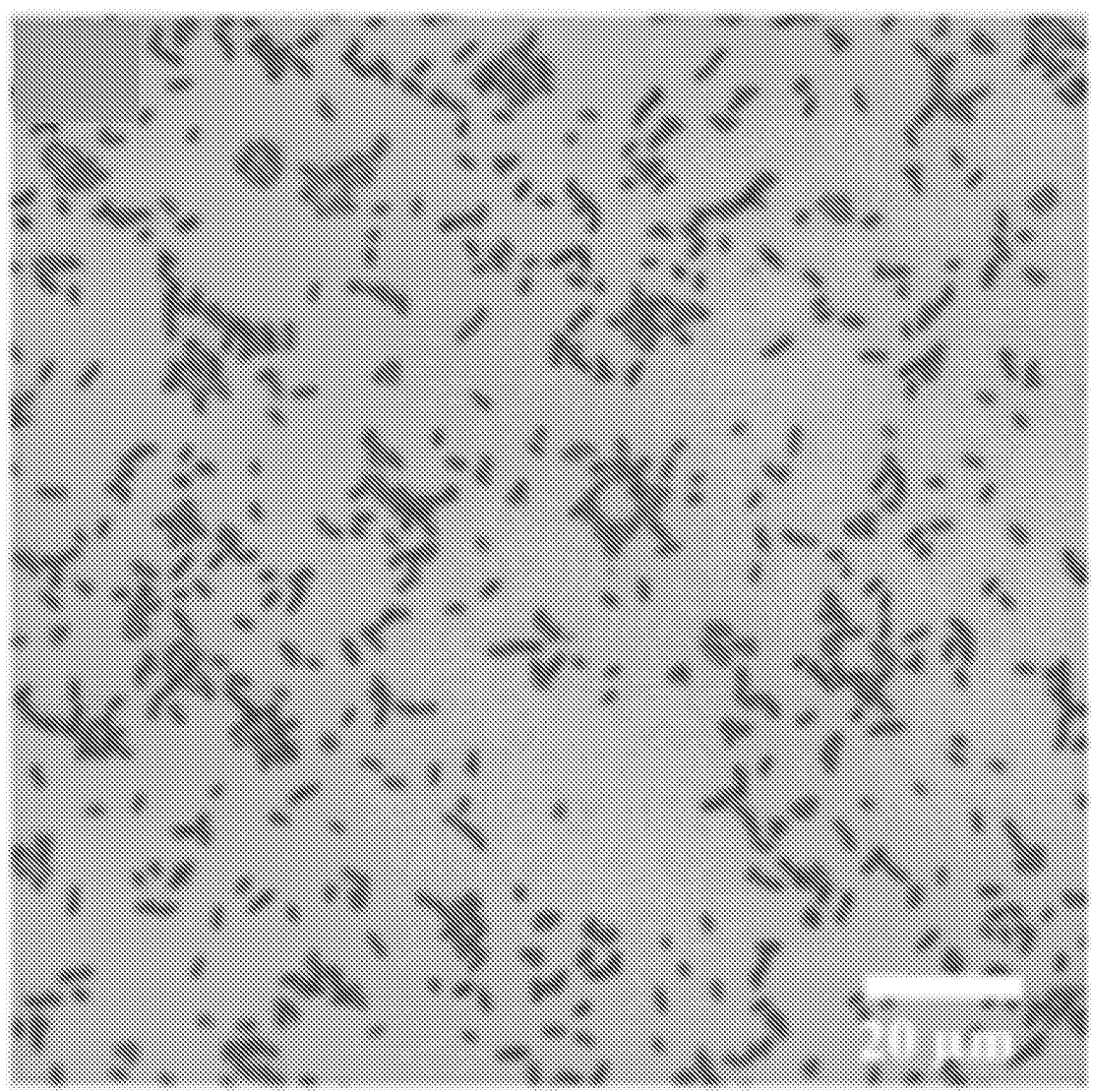

FIG. 13A, FIG. 13B, and FIG. 13C are optical microscope images of *P. aeruginosa* strain PAO1 cells on gold thin films used to assess rinsing protocols. (FIG. 13A) Sensor surface containing *P. aeruginosa* cells washed with 20% PBS buffer for 5 min; (FIG. 13B) Sensor surface containing fixed *P. aeruginosa* cells washed three times with undiluted PBS buffer for 5 min each and washed with water for 5 min; (FIG. 13C) same as FIG. 13B but water rinsed for 30 s. All sensor chips were gently dried for 5 min using $N_2$ gas after the washing steps.

Figure 14:
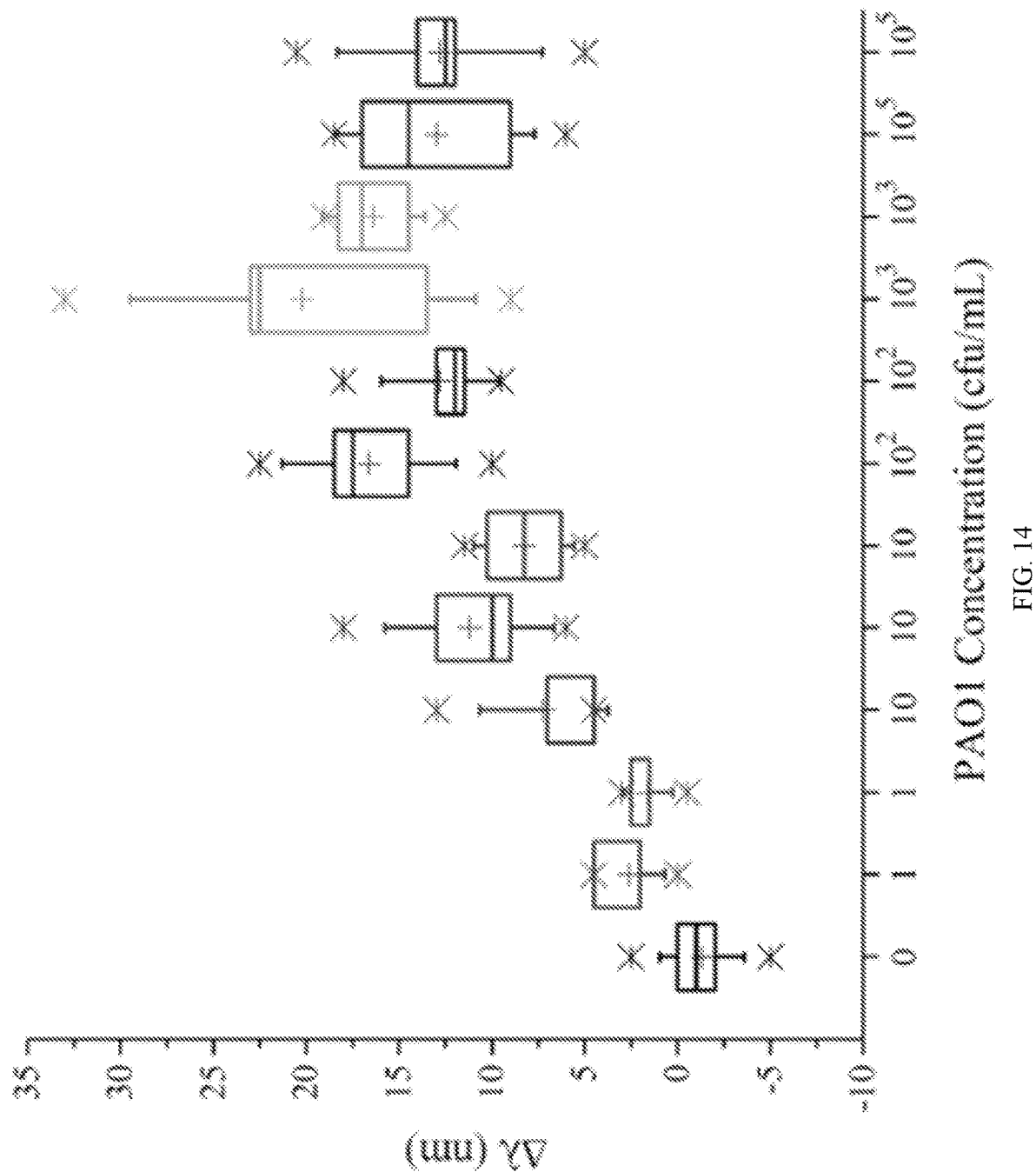

FIG. 14 is a series of box plots representing inter- and intrabatch variations of sensor chips. LSPR wavelength shift is a function of bacterial concentration. Each nox plot represents a different bacterial concentration with 9-14 individual data points. The central box line represents $50^{th}$ percentile. The lower and upper boundary lines represent the $25^{th}$ and $75^{th}$ percentiles, respectively. The plus sign represents the mean of all data points. The whisker extends to one standard deviation. Diagonal crosses (x) represent the $1^{st}$ and $99^{th}$ percentiles. Interbatch variation is judged by comparing the means of different boxes of the same color, while intrabatch variation is measured by the height of the box.

Figure 15:
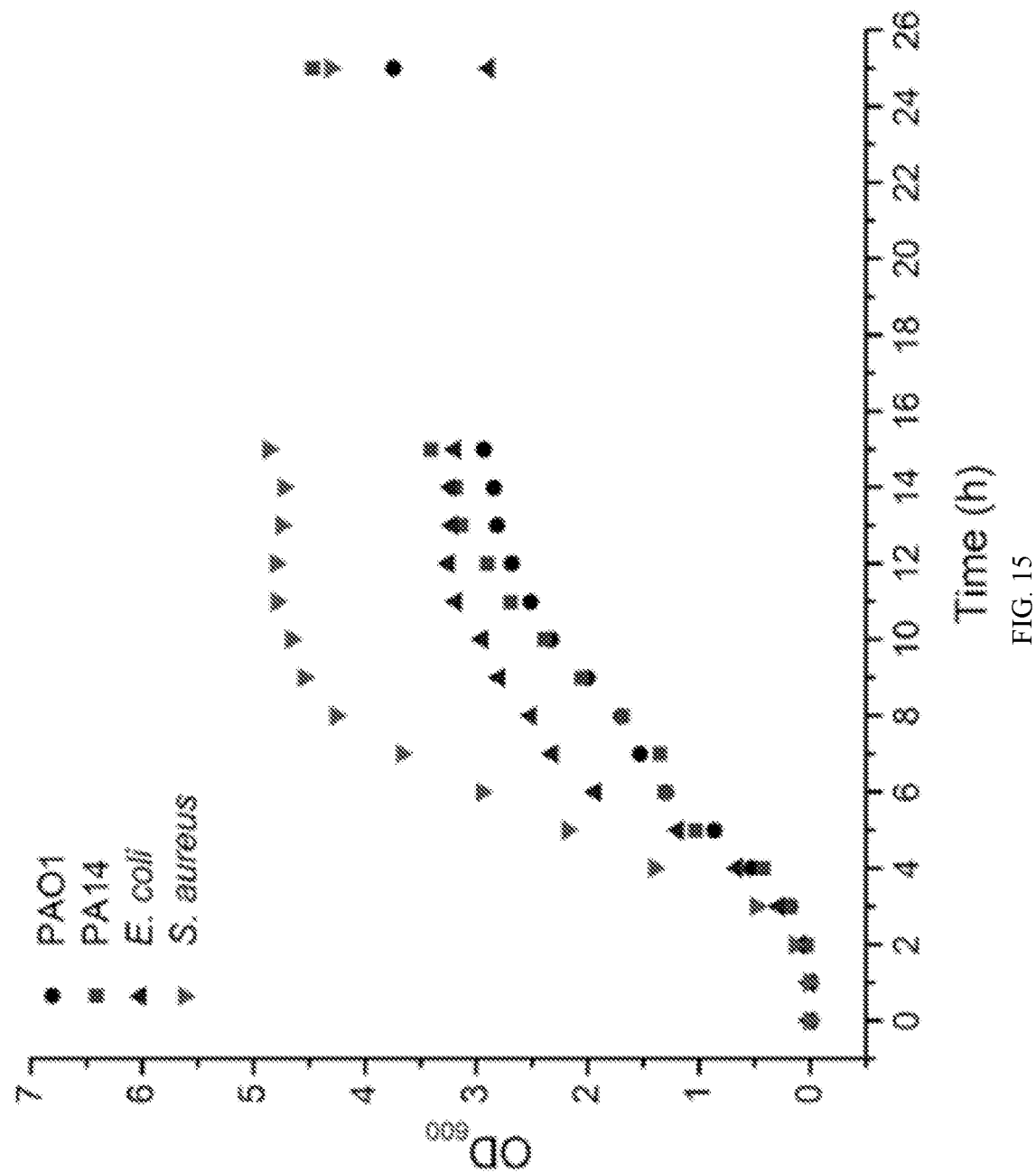

FIG. 15 is a graph showing growth curves of PAO1, PA14, *E. coli*, and *S. aureus*.

Figure 16:
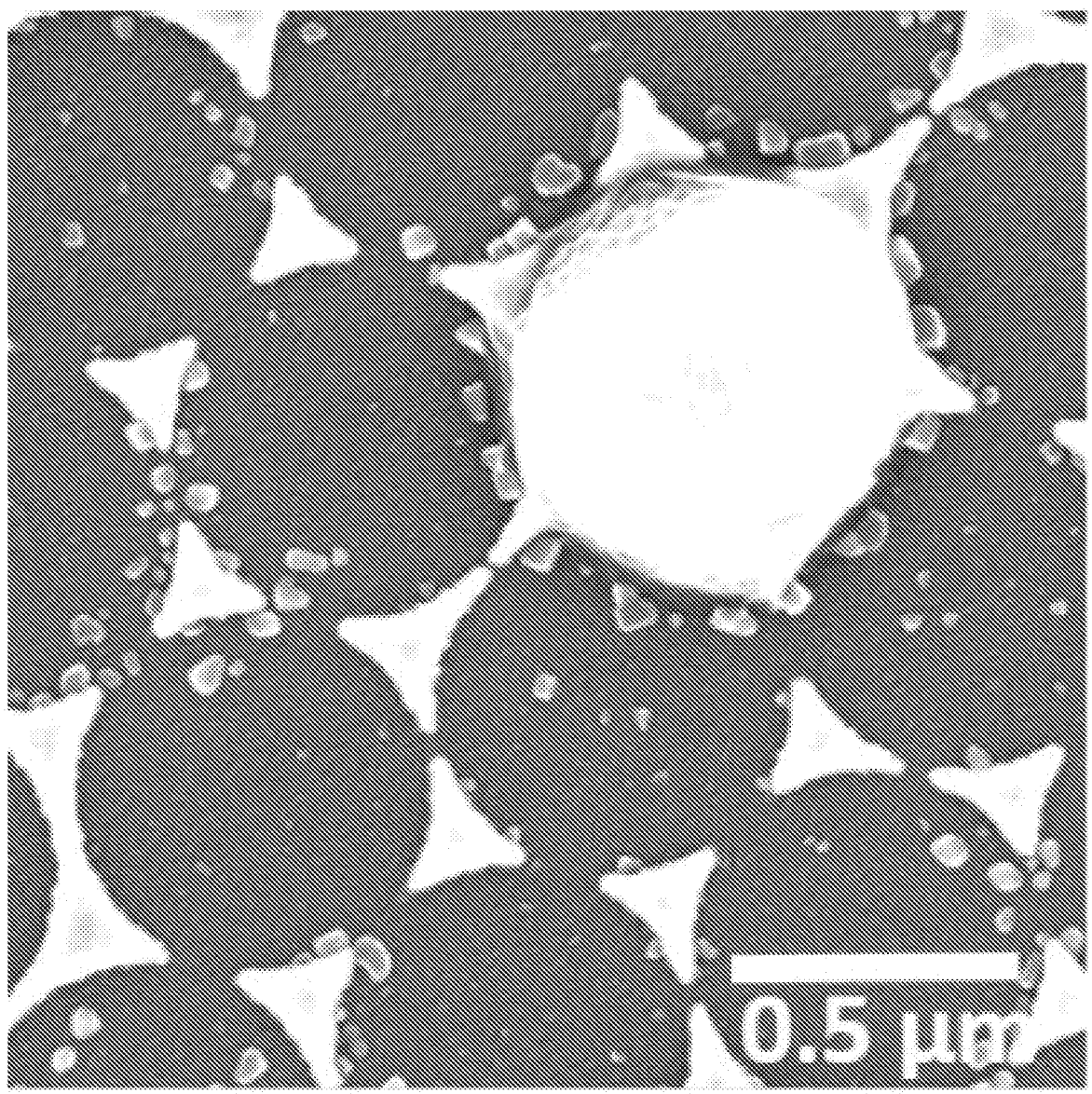

FIG. 16 is SEM image of a *S. aureus* cell on Bt-PEG thiol/PEG thiol, neutravidin, and Bt-aptamer modified sensor surface.

Figure 17A:
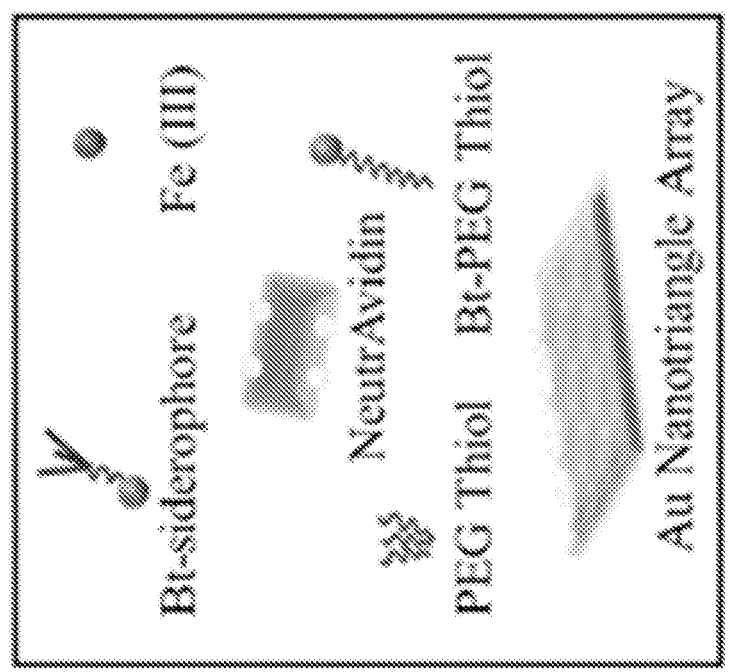
Figure 17A:
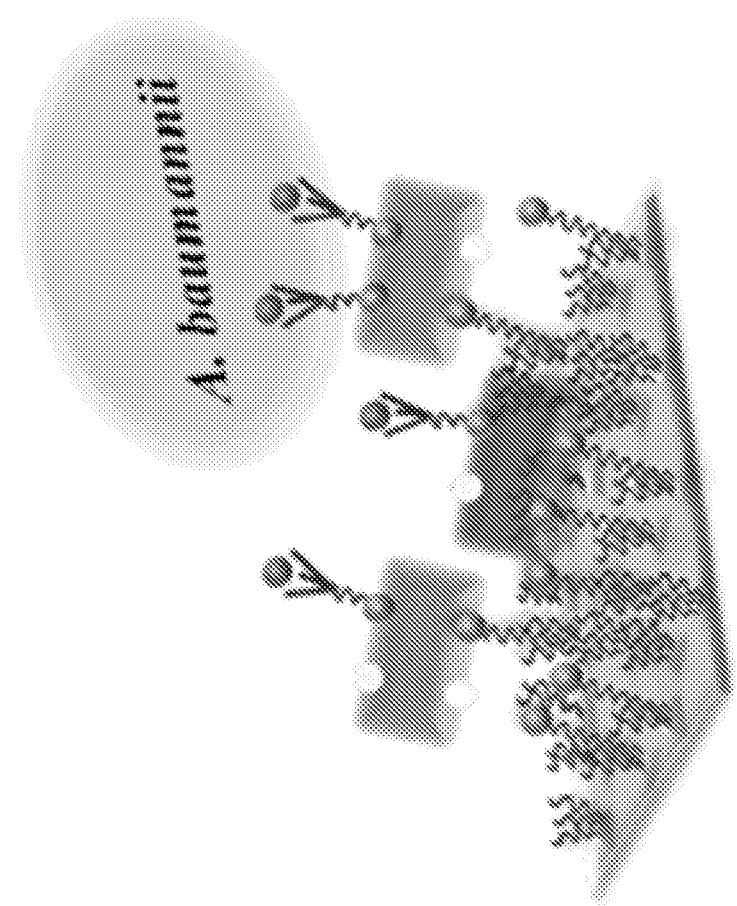
Figure 17B:
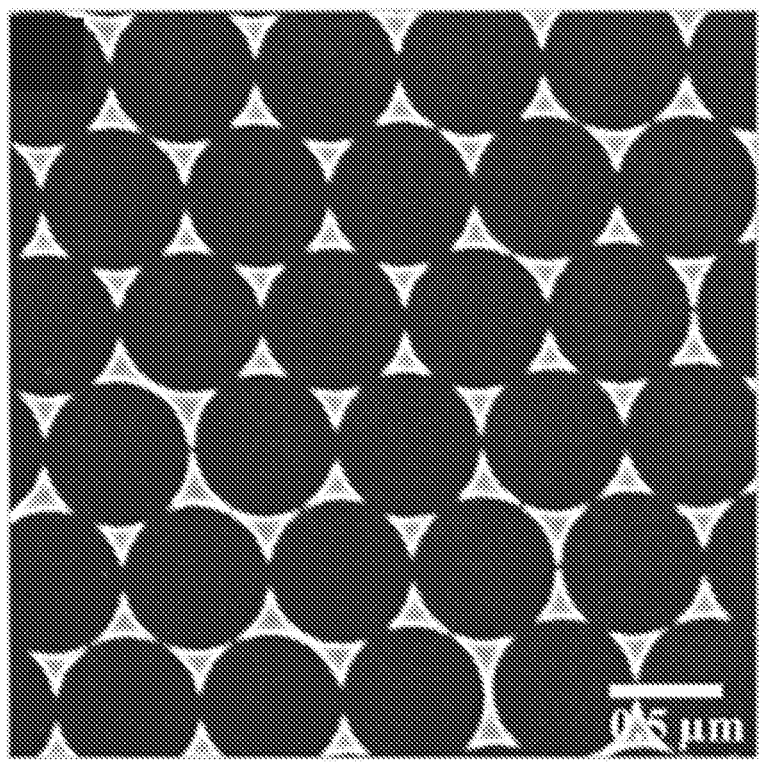
Figure 17C:
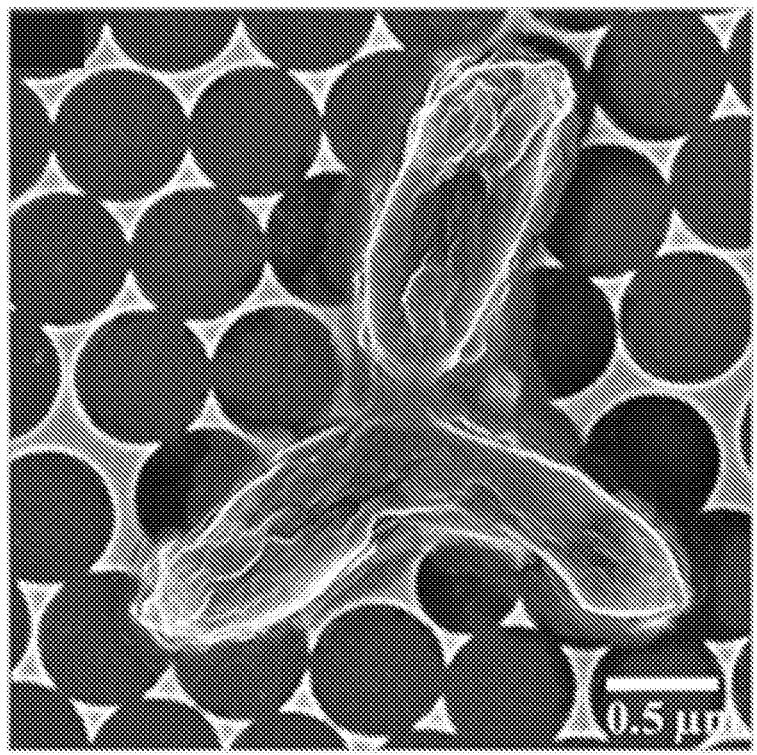

FIG. 17A is a schematic illustration of a siderophore LSPR sensor chip design (left) with a legend (right). FIGS. 17B and 17C are representative SEM images of a bare sensor chip (FIG. 17B) and a sensor chip with captured *A. baumannii* cells (FIG. 17C).

Figure 18:
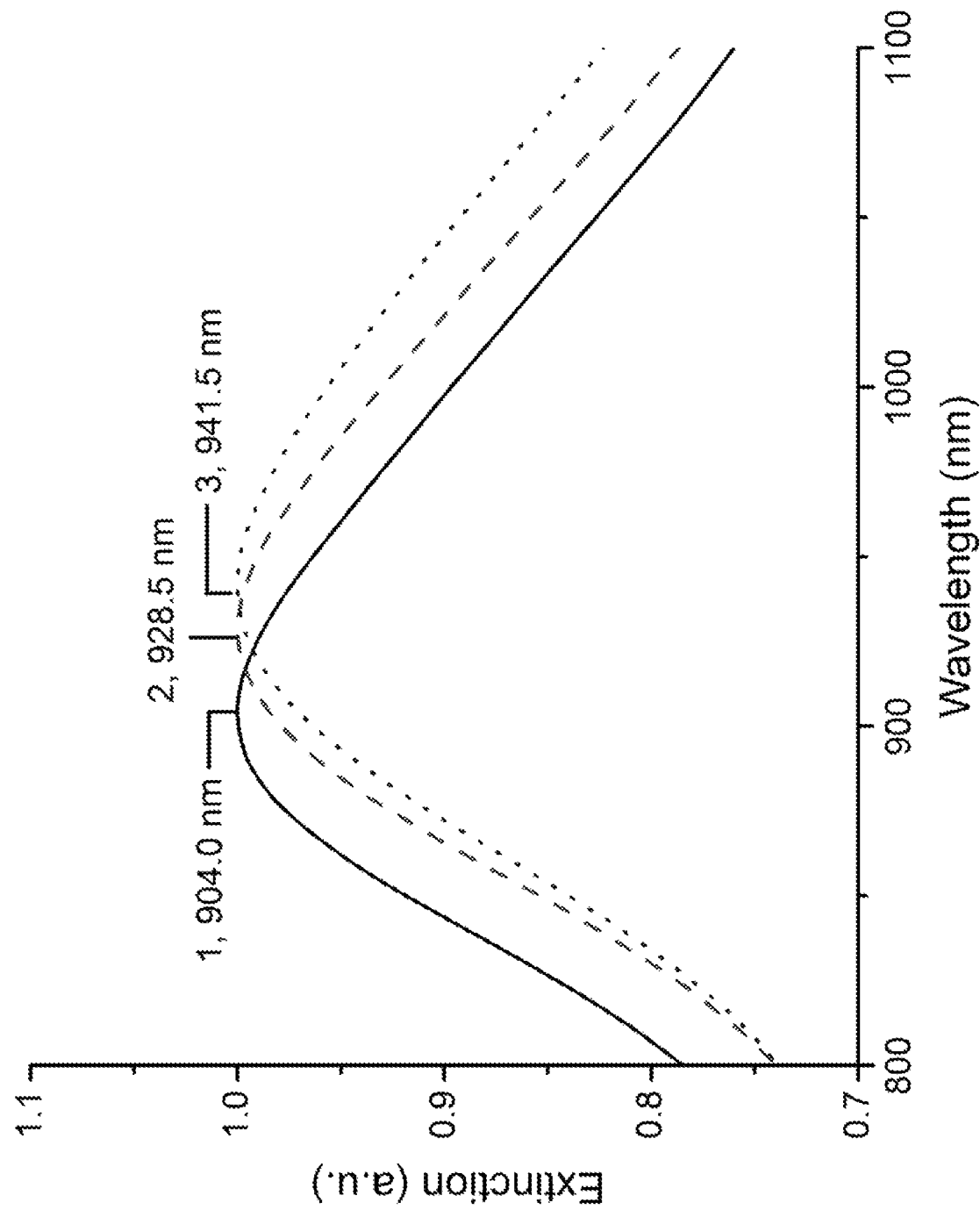

FIG. 18 is a graph showing representative LSPR extinction spectra of a nanoscale Au trigonal prism array (curve 1), the same array modified with Bt-PEG thiol/PEG thiol, NeutrAvidin, Bt-siderophore, and Fe(acac)$_3$ (curve 2), and after subsequent exposure to 4×10$^6$ cfu mL$^{-1}$ *A. baumannii* in 10 mM sodium phosphate solution (curve 3).

Figure 19:
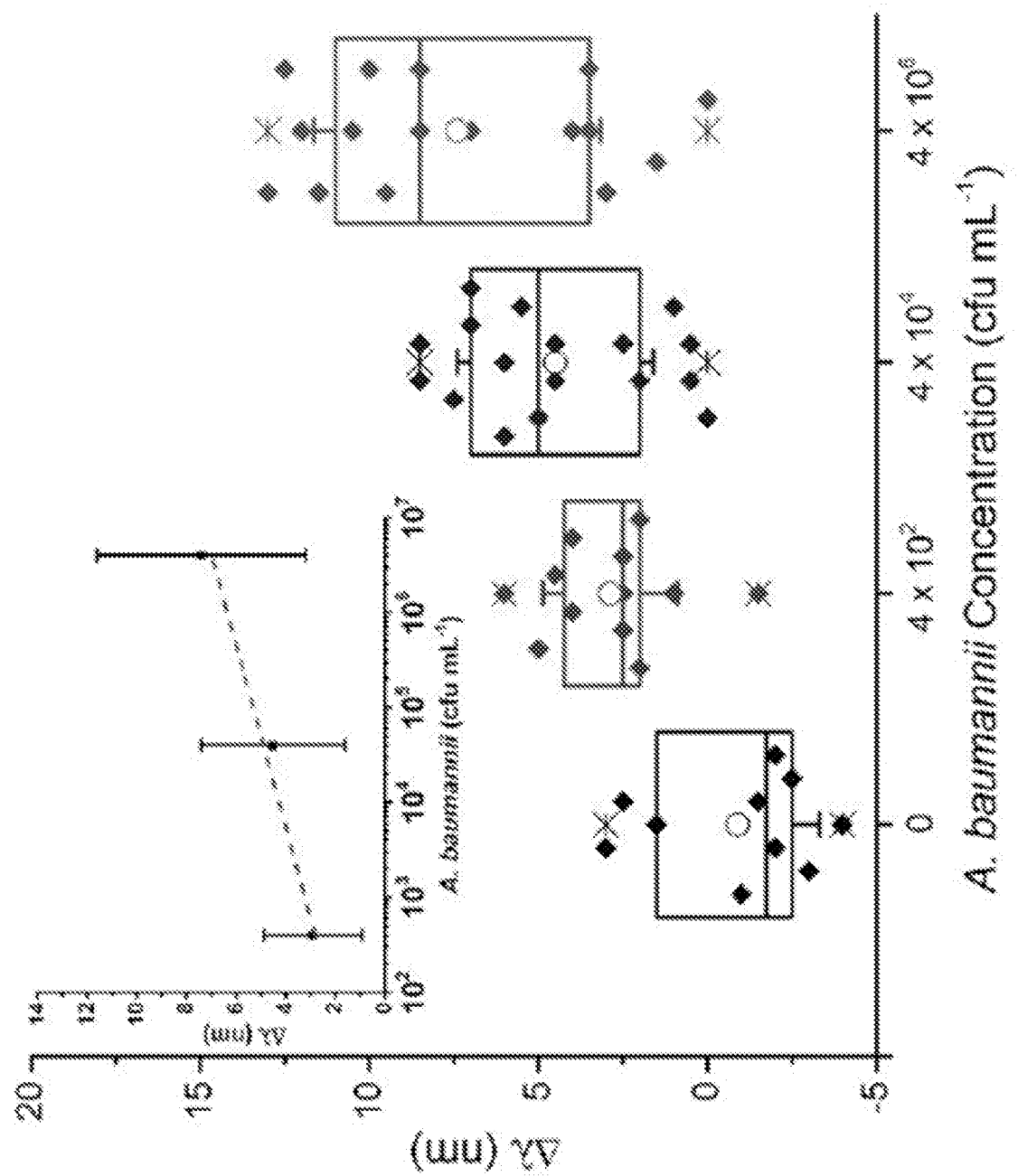

FIG. 19 is a series of box plots demonstrating LSPR wavelength shift (Δλ (nm)) as a function of *A. baumannii* concentration (cfu/mL). *A. baumannii* was suspended in 10 mM sodium phosphate solution. Each box plot represents a different bacterial concentration with 10-17 individual data points (solid diamonds are results of individual experiments). The circle represents the mean of all data. The whiskers extend to ±one standard deviation. The lower, central, and upper box lines represent $25^{th}$, $50^{th}$, and $75^{th}$ percentile, respectively. Diagonal crosses (x) represent the $1^{st}$ and $99^{th}$ percentiles. Insert shows a linear fit of LSPR wavelength shift vs. log bacterial concentration, where the error bars represent the standard deviation of all data at a specific bacterial concentration.

Figure 20:
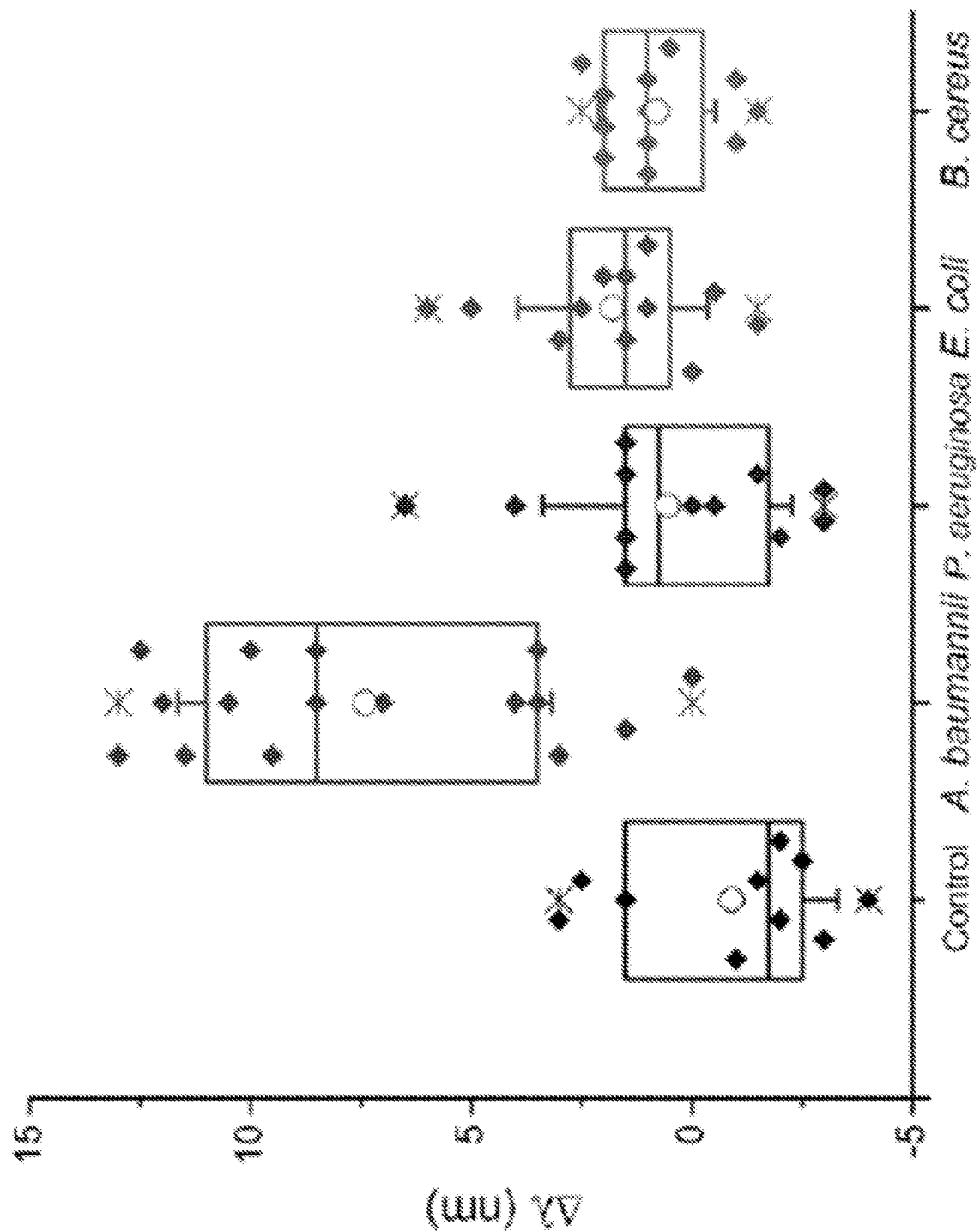

FIG. 20 is a series of box Plots showing LSPR wavelength shift corresponding to different bacteria binding to an *A. baumannii*-specific siderophore. A bacterial load of 10$^7$ cfu mL$^{-1}$ in 10 mM sodium phosphate solution was tested in each case. Each box plot represents a control or a different bacterial sample with 10-16 individual data points (solid diamonds are results of individual experiments). The circle represents the mean of all data points. The whisker extends to ±one standard deviation. The lower, central, and upper box lines represent $25^{th}$, $50^{th}$, and $75^{th}$ percentile, respectively. Diagonal crosses (x) represent the $1^{st}$ and $99^{th}$ percentiles.

Figure 21:
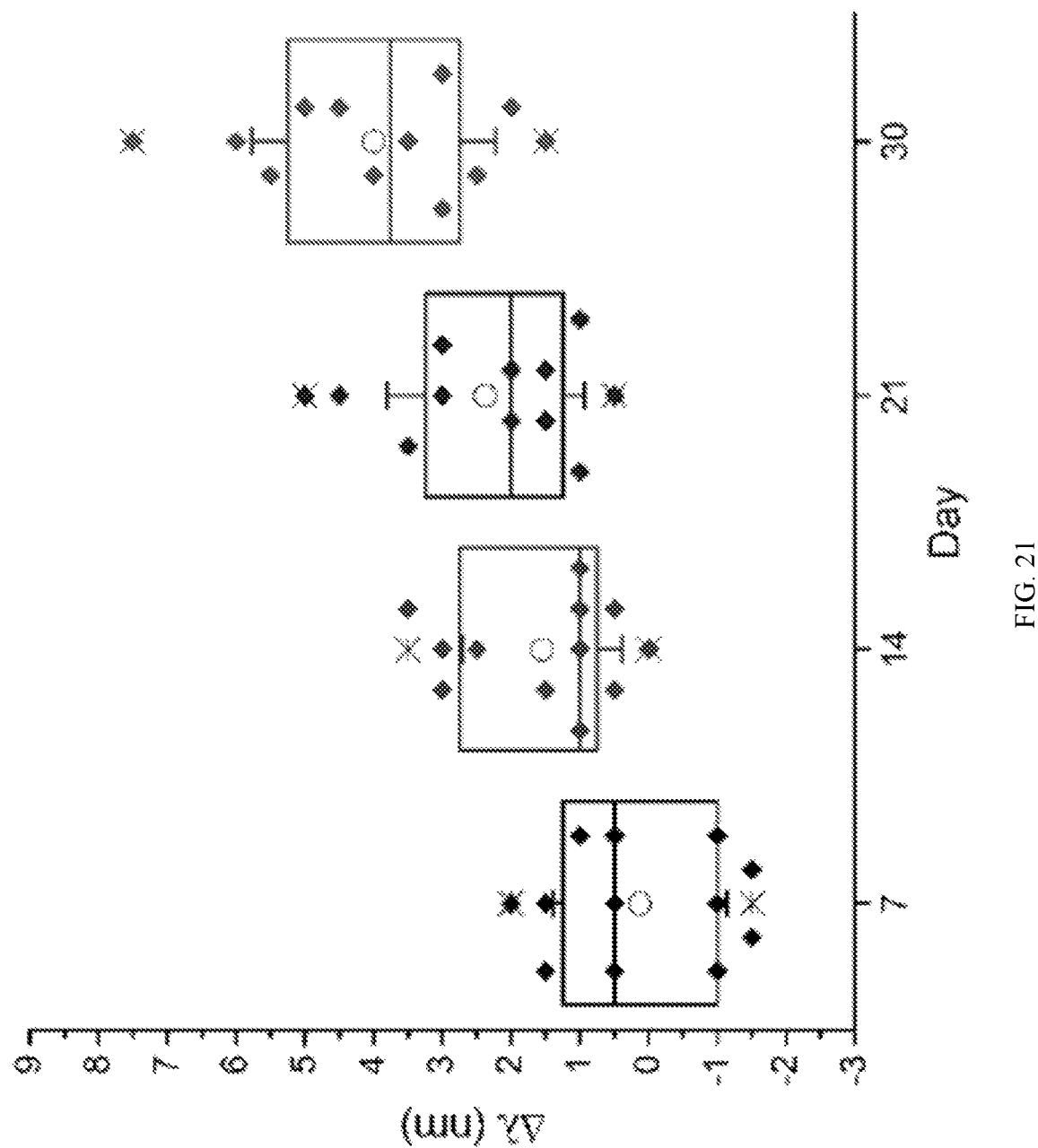

FIG. 21 is a series of box plots showing the stability of modified sensor chips in ambient conditions as monitored using LSPR wavelength shift as a function of time. Each box plot represents the aging process of 12 individual Au nanotriangle arrays modified with Bt-PEG thiol/PEG thiol, NeutrAvidin, Bt-siderophore, and $Fe(acac)_3$. The circle represents the mean of all data points. The whisker extends to ±one standard deviation. The lower, central, and upper box lines represent $25^{th}$, $50^{th}$, and $75^{th}$ percentile, respectively. Diagonal crosses (x) represent the $1^{st}$ and $99^{th}$ percentiles.

FIG. 22 is a graph showing LC-MS characterization of biotinylated siderophore in buffer. A UV chromatogram of the LC separated biotinylated siderophore is shown in the black trace. A number of components were found and the peaks were fit to Gaussians (peaks 1 to 5, colored traces) to estimate relative abundances of the components, which are tabulated in the Inset.

FIG. 23 is a series of box plots showing the LSPR wavelength shift after bacterial binding onto various sensor surfaces. *A. baumannii* ($4\times10^6$ cfu $mL^{-1}$) was used in all experiments. Each box plot represents a different surface modification with 12-16 individual data points (solid diamonds are results of individual experiments). The circle represents the mean of all data points. The whisker extends to one standard deviation in each direction. The lower, central, and upper box lines represent $25^{th}$, $50^{th}$, and $75^{th}$ percentiles, respectively. Diagonal crosses (x) represent the $1^{st}$ and $99^{th}$ percentiles.

DETAILED DESCRIPTION

Disclosed herein are biosensors and methods for detection of analytes in a sample. For example, the biosensors and methods may be used for whole-cell bacterial detection. The biosensors disclosed herein are characterized by rapid detection, extraordinary sensitivity, clinically relevant dynamic range, selectivity over detection of other bacteria, and/or excellent shelf life when stored in ambient conditions.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

*Acinetobacter baumannii* and *A. baumannii* are used interchangeably herein. *A. baumannii* is a typically short, almost round, rod-shaped Gram-negative bacterium. It can be an opportunistic pathogen in humans, affecting people with compromised immune systems. Some possible types of *A. baumannii* infections include Pneumonia, bloodstream infections, meningitis, wound and surgical site infections, and urinary tract infections. Symptoms of *A. baumannii* infections include fevers and chills, rash, confusion and/or altered mental states, pain or burning sensations when urinating, strong urge to urinate frequently, sensitivity to bright light, nausea (with or without vomiting), muscle and chest pains, breathing problems, and cough (with or without yellow, green, or bloody mucus). In some cases, *A. baumannii* may present no infection or symptoms, as with colonizing an open wound or tracheostomy site.

"Affinity" and "binding affinity" as used interchangeably herein refer to the tendency or strength of binding between molecules. For example, affinity may refer to the tendency of strength of binding of avidin, streptavidin, or neutravidin to biotin. As another example, affinity may refer to the tendency of binding of an aptamer to its target bacterium. The binding affinity may be represented by the equilibrium dissociation constant ($K_D$), the dissociation rate ($k_d$), or the association rate ($k_a$).

"Aptamer" as used herein refers to an oligonucleotide or peptide molecule that can bind to pre-selected targets with high affinity and specificity. The pre-selected target may be any desired bacteria, including *Pseudomonas aeruginosa*. Aptamers may assume a variety of shapes due to their propensity to form helices and single-stranded loops. An oligonucleotide or nucleic acid aptamer can be a single-stranded DNA or RNA (ssDNA or ssRNA) molecule. A peptide aptamer can include a short variable peptide domain, attached at both ends to a protein scaffold.

"Gram positive" is a taxonomic feature referring to bacteria which take up standard crystal violet primary Gram-staining dye. Gram staining is a process that differentiates bacteria by the chemical and physical properties of their cell walls by detecting peptidoglycan, which is present in the cell walls of Gram-positive bacteria. Gram-positive bacteria may have more extensive peptidoglycan crosslinking in their cell walls than Gram-negative bacteria.

"Gram-negative" is a taxonomic feature referring to bacteria which do not take up standard crystal violet primary Gram-staining dye. Peptidoglycan is typically present in a small layer in the cell walls of Gram-negative bacteria. This small layer is easily dissolved with certain organic solvents such as, for example, ethanol or acetone, thus preventing the cell from retaining the violet primary stain. Gram-negative cells may be characterized by their cell envelopes, which are composed of a thin peptidoglycan cell wall sandwiched between an inner cytoplasmic cell membrane and a bacterial outer membrane. The ability of bacteria to retain or resist staining generally reflects the structure of the cell wall, and it has been suggested that Gram-positive bacteria have more extensive peptidoglycan crosslinking and than their Gram-negative counterparts.

*Pseudomonas aeruginosa* and *P. aeruginosa* are used interchangeably herein. *Pseudomonas aeruginosa* is a common Gram-negative, rod-shaped bacterium that can cause disease in plants and animals. *P. aeruginosa* typically infects the airway, urinary tract, burns, and wounds, and also causes other blood infections. *P. aeruginosa* has many strains, including strain PAO1, PA7, UCBPP-PA14 (PA14), and *Pseudomonas aeruginosa* strain 2192. Some strains of *P. aeruginosa* have developed multi-drug resistance.

"Sample", "biological sample", or "test sample" as used interchangeably herein can mean any sample in which the presence and/or level of a target bacteria is to be detected. Samples may include a biological sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Siderophore" as used herein refers to a molecule that binds and transports iron. A siderophore may be a natural siderophore secreted by microorgansims such as bacteria or fungi. A siderophore may be a synthetic siderophore.

"Subject" and "patient" are used interchangeably herein. The subject may be a human or a non-human animal. The subject may be a vertebrate. The subject may be a mammal. The mammal may be a primate or a non-primate. The mammal can be a primate such as a human; a non-primate such as, for example, dog, cat, horse, cow, pig, mouse, rat, camel, llama, goat, rabbit, sheep, hamster, and guinea pig; or non-human primate such as, for example, monkey, chimpanzee, gorilla, orangutan, and gibbon. The subject may be male. The subject may be female. In some embodiments, the subject is human. The subject or patient may be undergoing other forms of treatment.

2. Biosensors for Detection of Analytes

Disclosed herein are biosensors for detection of analytes. The biosensors disclosed herein may be used for whole-cell bacterial detection.

The biosensor comprises an array of gold nanoparticles. The array of gold nanoparticles may be immobilized on the biosensor surface. The gold nanoparticles may be immobilized on the biosensor surface by any suitable technique known in the art, for example by nanosphere lithography (NSL). The array of gold nanoparticles may comprise any suitable shape of nanoparticle, including but not limited to triangles, spheres, rods, stars, cubes, octahedrons, plates, and prisms. For example, the array of gold nanoparticles may comprise gold nanotriangles.

The gold nanoparticles may be of any suitable size useful for analyte detection. For example, the gold nanoparticles may have an in-plane width of about 10 nm to about 500 nm. The gold nanoparticles may have an in-plane width of about 10 nm to about 500 nm, about 25 nm to about 450 nm, about 50 nm to about 400 nm, about 75 nm to about 350 nm, about 100 nm to about 300 nm, about 125 nm to about 250 nm, or about 150 nm to about 200 nm. For example, the gold nanoparticles may have an in-plane width of about 180 nm, about 190 nm, about 200 nm, about 210 nm, about 220 nm, or about 230 nm. The gold nanoparticles may have an out-of-plane height of about 20 nm to about 60 nm. For example, the gold nanoparticles may have an out-of-plane height of about 20 nm, about 30 nm, about 40 nm, about 40 nm, or about 60 nm.

The biosensor may comprise gold nanoparticles aligned in any suitable array for analyte detection. For example, the biosensor may comprise a hexagonal array of gold nanoparticles. The gold nanoparticles in the array may be spaced at any suitable interparticle distance to useful for whole-cell bacterial detection. For example, the gold nanoparticles may be spaced at an interparticle distance of about 50 nm to about 300 nm. For example, the gold nanoparticles may be spaced at an interparticle distance of about 50 nm to about 300 nm, about 75 nm to about 250 nm, about 100 nm to about 200 nm, or about 125 nm to about 150 nm. For example, the gold nanoparticles may be spaced at an interparticle distance of about 100 nm, about 110 nm, about 120 nm, about 130 nm, or about 140 nm.

The biosensor further comprises biotinylated polyethylene glycol thiol in direct contact with one or more of the gold nanoparticles. The biosensor further comprises polyethylene glycol thiol in direct contact with one or more of the gold nanoparticles. The biosensor may comprise a ratio of biotinylated polyethylene glycol thiol to polyethylene glycol thiol of about 1:10 to about 1:1 by volume. For example, the biosensor may comprise a ratio of biotinylated polyethylene glycol thiol to polyethylene glycol thiol of about 1:3 by volume.

The biosensor may further comprise a molecule with high affinity for biotin immobilized on a surface of the biotinylated polyethylene glycol thiol. For example, the biosensor may comprise at least one neutravidin molecule immobilized on a surface of the biotinylated polyethylene glycol thiol. As another example, the biosensor may comprise at least one avidin molecule immobilized on a surface of the biotinylated polyethylene glycol thiol. In some embodiments, the biosensor may comprise at least one streptavidin molecule immobilized on a surface of the biotinylated polyethylene glycol thiol.

The biosensor may further comprise at least one affinity reagent immobilized on a surface of the at least one molecule with high affinity for biotin. The affinity reagent may be any suitable affinity reagent that selectively binds to the desired analyte in a sample. The analyte may be a bacterium, fungus, virus, and the like. For example, the affinity reagent may be any suitable affinity reagent that selectively binds to a bacterial cell in a sample. The bacterial cell may be a whole bacterial cell.

In some embodiments, the affinity reagent is an aptamer. The aptamer may be biotinylated. For example, the biosensor may further comprise a biotinylated aptamer immobilized on a surface of the at least one molecule with high affinity for biotin. For example, the biosensor may comprise at least one biotinylated aptamer immobilized on a surface of the neutravidin molecule. The biotinylated aptamer may be designed or selected to bind to any desired target analyte. For example, the biotinylated aptamer may be designed or selected to bind to any desired target bacteria. In some embodiments, the biotinylated aptamer may be designed or selected to bind to whole cell bacteria. For example, the biotinylated aptamer may be designed or selected to bind to Gram-positive bacteria. As another example, the biotinylated aptamer may be designed or selected to bind to Gram-negative bacteria. In some embodiments, the biotinylated aptamer may be selected to bind to *Pseudomonas aeruginosa*. The biotinylated aptamer may selectively bind *Pseudomonas aeruginosa*. For example, the biotinylated aptamer may bind *Pseudomonas aeruginosa* without appreciable binding to other bacterial strains. The biotinylated aptamer may bind *Pseudomonas aeruginosa* without appreciable binding to other Gram-negative bacteria. For example, the biotinylated aptamer may bind *Pseudomonas aeruginosa* without appreciable binding to *E. coli*. The biotinylated aptamer may bind *Pseudomonas aeruginosa* without appreciable binding to Gram-positive bacteria. For example, the biotinylated aptamer may bind *Pseudomonas aeruginosa* without appreciable binding to *S. aureus*. The biotinylated aptamer may selectively bind *Pseudomonas aeruginosa* strain PAO1. For example, the biotinylated aptamer may selectively bind *Pseudomonas aeruginosa* strain PAO1 without appreciable binding to other *Pseudomonas aeruginosa* strains, such as PA14. In some embodiments, the biotinylated aptamer may selectively bind *Pseudomonas aeruginosa* strain PAO1 without appreciable binding to *Pseudomonas aeruginosa* strain PA14, *E. coli*, or *S. aureus*.

In some embodiments, the biotinylated aptamer is encoded by a nucleotide sequence with at least 80% sequence identity with SEQ ID NO: 1. For example, the biotinylated aptamer may be encoded by a nucleotide sequence with at least 80% identity, at least 85% identity, at least 90% identity, at least 95% identity, at least 96% identity, at least 97% identity, at least 98% identity, or at least 99% identity with SEQ ID NO: 1. In some embodiments, the biotinylated aptamer is encoded by the nucleotide sequence of SEQ ID NO: 1.

In other embodiments, the affinity reagent may be a siderophore. The siderophore may be a natural siderophore or an artificial siderophore. In some embodiments, the siderophore is biotinylated. For example, the biosensor may comprise at least one biotinylated siderophore immobilized on a surface of the neutravidin molecule. The siderophore may be a hydroxamate siderophore. The siderophore may be a catecholate siderophore. The siderophore may be a biscatecholate-monohydroxamate mixed ligand siderophore. The biscatecholate-monohydroxamate mixed ligand siderophore may comprise three repeating polyethylene glycol units linked to a biotin molecule.

The siderophore may selectively bind any desired target analyte. For example, the siderophore may selectively bind any desired target bacteria. In some embodiments, the siderophore may selectively bind to whole cell bacteria. The siderophore may selectively bind *Acinetobacter baumannii*. For example, the biotinylated siderophore may bind *Acinetobacter baumannii* without appreciable binding to other bacterial strains. The biotinylated siderophore may bind *Acinetobacter baumannii* without appreciable binding to other Gram-negative bacteria. For example, the biotinylated siderophore may bind *Acinetobacter baumannii* without appreciable binding to *E. coli* or *Pseudomonas aeruginosa*. The biotinylated siderophore may bind *Acinetobacter baumannii* without appreciable binding to Gram-positive bacteria. For example, the biotinylated siderophore may bind *Acinetobacter baumannii* without appreciable binding to *B. cereus*. In some embodiments, the biotinylated aptamer may selectively bind *Acinetobacter baumannii* without appreciable binding to *Pseudomonas aeruginosa, E. coli*, and *B. cereus*.

The disclosed biosensors demonstrate surprisingly high stability. The disclosed biosensors may be stable in ambient conditions for at least 2 weeks. For example, the disclosed biosensors may be stable in ambient conditions for at least 2 weeks, at least 3 weeks, at least 4 weeks, at least 5 weeks, at least 6 weeks, at least 7 weeks, at least 8 weeks, at least 9 weeks, at least 10 weeks, at least 12 weeks, at least 4 months, at least 5 months, or at least 6 months. In some embodiments, the disclosed biosensors are stable in ambient conditions for at least 2 months. The disclosed biosensors also demonstrate high stability when stored in $N_2$ environment. When stored in $N_2$ environment, the disclosed biosensors may be stable for at least at least 2 weeks, at least 3 weeks, at least 4 weeks, at least 5 weeks, at least 6 weeks, at least 7 weeks, at least 8 weeks, at least 9 weeks, at least 10 weeks, at least 12 weeks, at least 4 months, at least 5 months, or at least 6 months. In some embodiments, the disclosed biosensors are stable in $N_2$ environment for at least 2 months.

The disclosed biosensors demonstrate surprisingly high sensitivity. The disclosed biosensors may be used to detect whole-cell bacteria wherein the concentration of bacteria in a sample is less than or equal to about $4 \times 10^6$ cfu/mL. For example, the disclosed biosensors may be used to detect whole-cell bacteria when the concentration of bacteria in a sample is about $4 \times 10^6$ cfu/mL, less than about $4 \times 10^6$ cfu/mL, less than about $4 \times 10^5$ cfu/mL, less than about $4 \times 10^4$ cfu/mL, less than about $4 \times 10^3$ cfu/mL, less than about 1000 cfu/mL, less than about 100 cfu/mL, or less than about 10 cfu/mL. In some embodiments, the disclosed biosensors may be used to detect a single bacterium in a sample, indicating extraordinary sensitivity for whole-cell bacterial detection.

3. Methods for Detecting Bacterial Infection

Further disclosed herein are methods for detecting bacterial infection in a subject. The method comprises obtaining a sample from the subject and contacting the sample with a biosensor disclosed herein.

The sample may be contacted with the disclosed biosensor under any suitable conditions for any suitable duration of time to achieve the desired binding of whole cell bacterial cells to the biosensor. In some embodiments, the sample may be contacted with the disclosed biosensor at about 37° C. for about 1 hour. The sample may be contacted with the biosensor under controlled humidity conditions.

After being contacted with the sample for the desired duration of time, the biosensor may be washed in any suitable buffer to remove bacterial cells that did not bind to the biosensor. When dried, salt crystals on sensor surfaces, can contribute to an apparent LSPR wavelength shift, thus confounding the bacterial-derived signal. In addition, lysis of bacteria could give rise to LSPR signals not correlated with the number of bacteria present in the sample. Thus, it is preferable to wash the biosensor under conditions sufficiently stringent to minimize salt crystal formation, yet gentle enough to leave surface-captured bacteria intact. For example, the biosensor may be washed three times with undiluted PBS for 5 minutes each wash. After washing in PBS, the biosensor may be immersed in water. For example, the biosensor may be washed three times for 5 minutes each with undiluted PBS, followed by water immersion for 30 seconds. The biosensor may be dried prior to characterization of LSPR spectra. For example, the biosensor may be dried with $N_2$ gas for 5 minutes prior to characterization of LSPR spectra.

The method further comprises detecting localized surface plasmon resonance (LSPR) of the sample and a control sample. The method further comprises comparing the wavelength shift of the maximum extinction of the LSPR of the sample to a LSPR wavelength shift in a control sample. Detecting the wavelength of the maximum extinction of the LSPR of the sample and/or that of the control sample may be performed using any suitable method under any suitable conditions known in the art. In some embodiments, UV-visible extinction spectroscopy may be used to detect the wavelength of the maximum extinction of the LSPR of the sample and/or that of the control sample. In some embodiments, UV-visible extinction spectrum measurements may be performed under controlled humidity conditions as the disclosed biosensor chips may be sensitive to humidity and temperature. In some embodiments, UV-visible extinction spectrum measurements may be performed in air. In other embodiments, UV-visible extinction spectrum measurements may be performed in suitable buffer, such as PBS.

Detecting bacterial infection using the disclosed biosensors involves measuring the wavelength shift ($\Delta\lambda$) before and after capture of the analyte, such as a whole bacterial cell, which subsequently causes a change in the dielectric environment, as reflected in the refractive index (n), surrounding the nanoparticles. This relationship can be expressed phenomenologically as $\Delta\lambda=m\Delta n[1-\exp(-2d/l_d)]$ where m is the refractive index sensitivity, $\Delta n$ is the change in refractive index induced by an adsorbate, d is the effective thickness of the adsorbate layer, and $l_d$ is the characteristic decay length for the evanescent electromagnetic field.

In accordance with the disclosed methods of detecting bacterial infection in a subject, a shift in the wavelength of maximum extinction of the localized surface plasmon resonance (LSPR) of the sample relative to the shift in the wavelength of maximum extinction of the LSPR of the control sample indicates a bacterial infection in the subject. In some embodiments, a concentration of bacteria of less than or equal to about $4\times10^6$ cfu/mL produces a positive shift in the wavelength of maximum extinction of the LSPR of the sample, indicating bacterial infection in the subject. For example, a concentration of bacteria of about $4\times10^6$ cfu/mL, less than about $4\times10^6$ cfu/mL, less than about $4\times10^5$ cfu/mL, less than about $4\times10^4$ cfu/mL, less than about $4\times10^3$ cfu/mL, less than about 1000 cfu/mL, less than about 100 cfu/mL, or less than about 10 cfu/mL may produce a positive shift in the wavelength of maximum extinction of the LSPR of the sample, indicating bacterial infection in the subject. In some embodiments, the disclosed biosensors may be used to detect bacterial infection in a subject when less than 100 bacterial cells are present in the sample. For example, the disclosed biosensors may be used to detect bacterial infection in a subject when less than 100, less than about 90, less than about 80, less than about 70, less than about 60, less than about 50, less than about 40, less than about 30, less than about 20, less than about 10, or less than about 5 bacterial cells are present in the sample. In some embodiments, the disclosed biosensors may be used to detect bacterial infection in a subject when a single bacterium is present in the sample, demonstrating the extraordinary sensitivity of the disclosed biosensors.

The disclosed method may detect bacterial infection in the subject in less than 24 hours. For example, the disclosed method may detect bacterial infection in the subject in less than 24 hours, less than about 12 hours, less than about 6 hours, less than about 5 hours, less than about 4 hours, or less than about 3 hours. In some embodiments, the method may detect bacterial infection in the subject in approximately 3 hours.

The disclosed method may detect Gram-positive bacterial infection in the subject. Gram-positive bacteria include, for example, *Actinomyces* spp. (*A. israelii*); *Aerococcus* spp.; *Bacillus* spp. (*B. anthracis*); *Bacterionema* spp.; *Bifidobacterium* spp.; *Clostridium* spp. (*C. botulinum, C. difficile, C. perfringens, C. tetani*); *Corynebacterium* spp. (*C. diphtherias*); *Corprococcus* spp.; *Deinobacter* spp.; *Deinococcus* spp.; *Enterococcus* spp. (*E. faecalis, E. faecium*); *Erysipelothrix* spp.; *Eubacterium* spp.; *Gemella* spp.; *Lactobacillus* spp.; *Lactococcus* spp.; *Leuconostoc* spp.; *Listeria* spp. (*L. monocytogenes*); *Marinococcus* spp.; *Melissococcus* spp.; *Methanobacterium* spp.; *Micrococcus* spp.; *Mycobacterium* spp. (*M. avium, M. leprae, M. lepromatosis, M. tuberculosis, M. ulcerans*); *Micropolyspora* spp.; *Nocardia* spp. (*N. asteroides*); *Pediococcus* spp.; *Peptococcus* spp.; *Peptostreptococcus* spp.; *Planococcus* spp.; *Propionibacterium* spp.; *Rothia* spp.; *Ruminococcus* spp.; *Saccharococcus* spp.; *Salinococcus* spp.; *Carcina* spp.; *Staphylococcus* spp. (*S. aureus, S. epidermidis, S. saprophyticus*); *Stomatococcus* spp.; *Streptococcus* spp. (*S. agalactiae, S. pneumoniae, S. pyogenes, S. viridans*); *Streptomyces* spp.; *Trichococcus* spp.; and *Vagococcus* spp. The subject may be infected with or at risk of infection from any combination of Gram-positive bacteria.

The disclosed method may detect Gram-negative bacterial infection in the subject. Gram-negative bacteria include, for example, *Acinetobacter* spp. (*A. baumannii*); *Bacterioides* spp. (*B. fragilis*); *Bordetella* spp. (*B. pertussis*); *Borrelia* spp. (*B. burgdorferi, B. garinii, B. afzelii*); *Brucella* spp. (*B. abortus, B. canis, B. melitensis, B. suis*); *Burkholderia* spp. (*B. mallei, B. pseudomallei*); *Calymmatobacterium* spp.; *Campylobacter* spp. (*C. fetus, C. jejuni*); *Chlamydia* spp. (*C. trachomatis, C. pneumoniae, C. psittaci*); *Chlamydophila* spp. (*C. pneumoniae*); *Citrobacter* spp.; *Coxiella* spp. (*C. burnetti*); *Edwardsiella* spp.; *Enterobacter* spp.; *Ehrlichia* spp. (*E. canis, E. chaffeensis*); *Escherichia* spp. (*E. coli*); *Francisella* spp. (*F. tularensis*); *Gardnerella* spp.; *Haemophilus* spp. (*H. influenzae*); *Helicobacter* spp. (*H. pylori*); *Klebsiella* spp. (*K. pneumoniae*); *Legionella* spp. (*L. pneumophila*); *Leptospira* spp. (*L. interrogans*); *Moraxella* spp. (*M. catarrhalis*); *Mycoplasma* spp. (*M. pneumoniae*); *Neisseria* spp. (*N. gonorrhoeae, N. meningitidis*); *Pasteurella* spp.; *Proteus* spp.; *Providencia* app.; *Pseudomonas* spp. (*P. aeruginosa, P. mallei*); *Rickettsia* spp. (*R. akari, R. prowazekii, R. rickettsia*); *Salmonella* spp. (*S. enterica, S. enterica enteritidis, S. enterica hadar, S. enterica* Heidelberg, *S. enterica infantis, S. enterica paratyphi, S. enterica typhi, S. enterica typhimurium*); *Serratia* spp.; *Shigella* spp. (*S. dysenteriae, S. sonnei*); *Spirillaceae* spp. (*S. minus*); *Streptobacillus* spp. (*S. moniliformis*); *Treponema* spp. (*T. pallidum*); *Vibrio* spp. (*V. cholerae*); and *Yersinia* spp. (*Y. enterocolitica, Y. pestis, Y. pseudotuberculosis*). The subject may be infected with or at risk of infection from any combination of Gram-negative bacteria.

In some embodiments, the disclosed method may detect *Pseudomonas aeruginosa* infection in the subject. In some embodiments, the disclosed method may detect infection with *Pseudomonas aeruginosa* strain PAO1 in the subject. In other embodiments, the disclosed method may detect *Acinetobacter baumannii* infection in the subject.

The biosensors and methods of the invention will be better understood by reference to the following examples, which are intended as an illustration of and not a limitation upon the scope of the invention.

4. Examples

The following Examples are offered as illustrative as a partial scope and particular embodiments of the disclosure and are not meant to be limiting of the scope of the disclosure.

Example 1

Experimental Procedures—Aptamer Based Biosensor

Materials: Biotin PEG thiol (MW 1000 Da) was purchased from Nanocs. PEG thiol (MW 550 Da) was purchased from Creative PEGWorks. Neutravidin (NA) and tris(2-carboxyethyl)phosphine hydrochloride (TCEP) were purchased from Thermo Fisher Scientific. Polystyrene beads (0.6 μm mean particle size), sulfuric acid (95.0-98.0%), hydrogen peroxide (30% w/w in $H_2O$), and ethyl alcohol (200 proof) were purchased from Sigma-Aldrich. Paraformaldehyde (16% w/v aqueous solution, methanol free), Dulbecco's Phosphate Buffered Saline (1×, without calcium and magnesium), and micro cover glass (No. 1, 18 mm×18 mm) were purchased from VWR. Lysogeny broth and granulated agar were purchased from BD Difco. Biotinylated aptamer (Bt-aptamer, 5' [Bt] ATACCAGCTTATTCAATTCCCCCGTTGCTTTCGCTTTTCCTTTCGCTTTTGTT CGTTTC GTCCCTGCTTCCTTTCTTGAGA-TAGTAAGTGCAATCT3') (SEQ ID NO:1) and fluorescently labeled biotinylated aptamer (6FAM-aptamer-Bt, 5' [6-carboxyfluorescein-ATACCAGCTTATTCAAT-TCCCCCGTTGCTTTCGCTTTTCCTTTCGCTTTTGTT CGTTTC GTCCCTGCTTCCTTTCTTGAGA-TAGTAAGTGCAATCT-[Bt]3') (SEQ ID NO: 2) were synthesized by Sigma-Aldrich. Deionized (DI) water used in all experiments was prepared using a Milli-Q Gradient water purification system with a resistivity of 18.2 MΩ·cm at 25° C. (Millipore).

Bacterial Cell Culture, Fixation, and Counting. *P. aeruginosa* strains PAO1 and PA14, *Escherichia coli* DH5α, and *Staphylococcus aureus* RN4220 used in these experiments were obtained from J. Shrout's laboratory (University of Notre Dame). All bacteria were streaked from freezer stocks and grown on lysogeny broth (LB) agar plates in a 37° C. incubator for 20 h. Cell cultures were first grown in a glass tube containing 6 mL of LB media for 9 h in a 37° C. incubator with shaking set at 240 rpm. Nine-hour bacterial samples (30 μL) were removed and serially diluted three times. All four serial dilutions were incubated at a 37° C. incubator for 14 h with shaking set at 240 rpm. All bacteria were harvested in their exponential growth phase. The cell culture was then washed twice using phosphate buffered saline (PBS) solution, and its optical density at 600 nm ($OD_{600}$) was adjusted to 0.80. A serial dilution was carried out to achieve various bacterial concentrations. To inactivate bacterial cells, 0.7 mL of bacterial solution was added into a microcentrifuge tube containing 0.7 mL of 6% paraformaldehyde solution, prepared by diluting 16% paraformaldehyde solution in PBS. As a control, 0.7 mL of PBS solution was added to a microcentrifuge tube containing 0.7 mL of 6% paraformaldehyde solution. Both tubes were heated at 62.5° C. water bath for 1 h to inactivate bacteria in solution. All samples were cooled to room temperature prior to use. All bacterial cell densities were confirmed using standard microbiology plating and counting methods. Specifically, the $OD_{600}$ of bacterial solution was adjusted to 0.80 upon harvesting cell culture. Each bacterial solution was diluted 6 orders of magnitude in LB media, and 100 μL of diluted bacterial solution was added onto a LB agar plate. The bacterial solution was spread evenly on a LB agar plate using a metal spreader, which was dipped in ethanol and flamed before and after each use. The bacteria containing LB agar plates were then incubated overnight at 37° C., and the colonies were counted the next day. Bacterial cell density was obtained by averaging the counts from nine LB agar plates (three plates were prepared in one experiment, and the same experiment was repeated three times on different days).

Sensor Fabrication. LSPR sensor chips were fabricated using NSL. Briefly, glass slides were soaked in piranha solution (Caution: piranha, 3:1 sulfuric acid/hydrogen peroxide, is a strong oxidizer and should be used with extreme caution!) overnight and rinsed with water. Polystyrene (PS) beads were gently spread as a monolayer at an air-water interface. The PS bead monolayer was transferred by first immersing a clean glass slide through the monolayer at an oblique angle, then translating the slide laterally to transfer PS beads onto the glass surface. The PS bead coated glass slides were dried at 60° C. prior to electron beam evaporation (UNIVEX 450B, Oerlikon) of Cr (1 nm) and Au (50 nm). The slides were then sonicated in chloroform to remove the PS beads, rinsed with water, dried with $N_2$ gas, and stored under $N_2$ environment. Each Au nanotriangle patterned glass slide (76.2 mm×25.4 mm) was diced into six pieces (10.16 mm×15.24 mm) using a dicing saw (Disco DAD3240) equipped with a diamond blade (Thermocarbon).

Sensor Surface Modification. A 1:3 (v:v) mixture of 1 mM Bt-PEG thiol:1 mM PEG thiol was self-assembled onto the sensor surface with mild shaking for 16 h. Then, 0.2 mL of neutravidin solution (1 mg/mL) was added with shaking for 1 h. Bt-aptamer solution (0.2 mL per tube) was heated in a 95° C. water bath for 30 min, cooled to room temperature, and then incubated with the neutravidin-modified sensor chips for 1 h with mild shaking under controlled humidity conditions. Sensor chips were gently rinsed with water and dried with $N_2$ gas after each step.

Bacterial Detection. In a typical experiment, one chip was exposed to 0.2 mL of control solution, and five chips were exposed to 0.2 mL of inactivated bacterial solution under controlled humidity conditions. Control and bacterial samples were incubated at 37° C. for 1 h. Each chip was then washed three times in PBS solution for 5 min per wash, followed by water wash for 30 s. All sensor chips were dried with $N_2$ gas setup for 5 min prior to characterization.

Characterization. LSPR spectra were acquired on a UV-visible/NIR spectrometer (Jasco V-670) equipped with a 60 mm integrating sphere (Jasco ISN-723). Each spectrum was averaged over three spectral accumulations collected from 400-1400 at 0.5 nm interval, and all extinction spectra were normalized. The probe beam size was ca. 8 mm×9 mm. For LSPR measurements in liquid, ~50 μL of PBS solution was added onto the sensor surface, and a coverslip was added to confine the liquid prior to measurement. Scanning electron microscope images of Au nanotriangle arrays with and without bacteria were collected using a field-emission scanning electron microscope (FEI Magellan 400) at 5.00 kV.

Prior to imaging, a thin layer of iridium (2.5 nm) was sputtered on the substrate to avoid surface charging.

Example 2

Sensor Fabrication and Sensor Surface Modification—Aptamer Based Biosensor

Figure 1A:
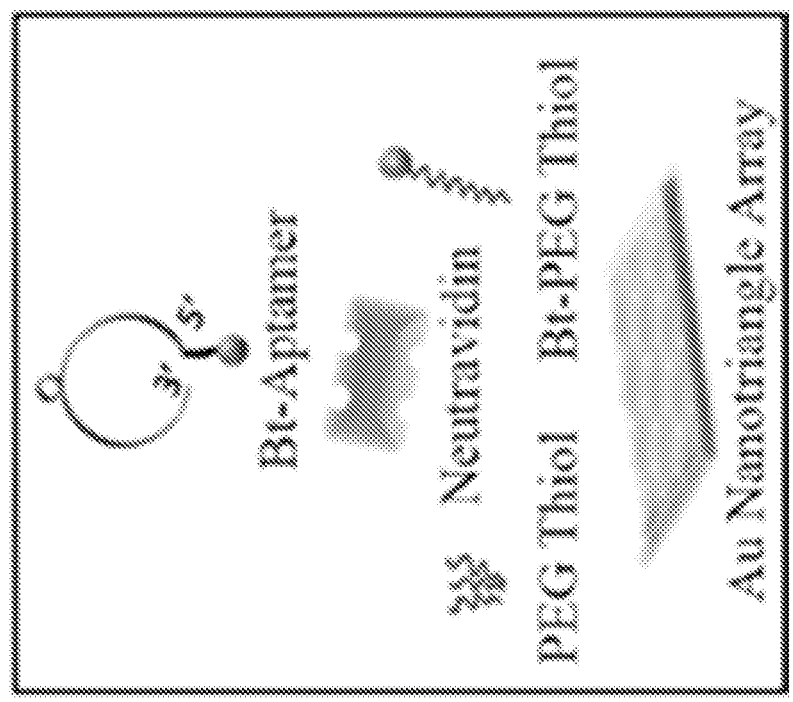
Figure 1A:
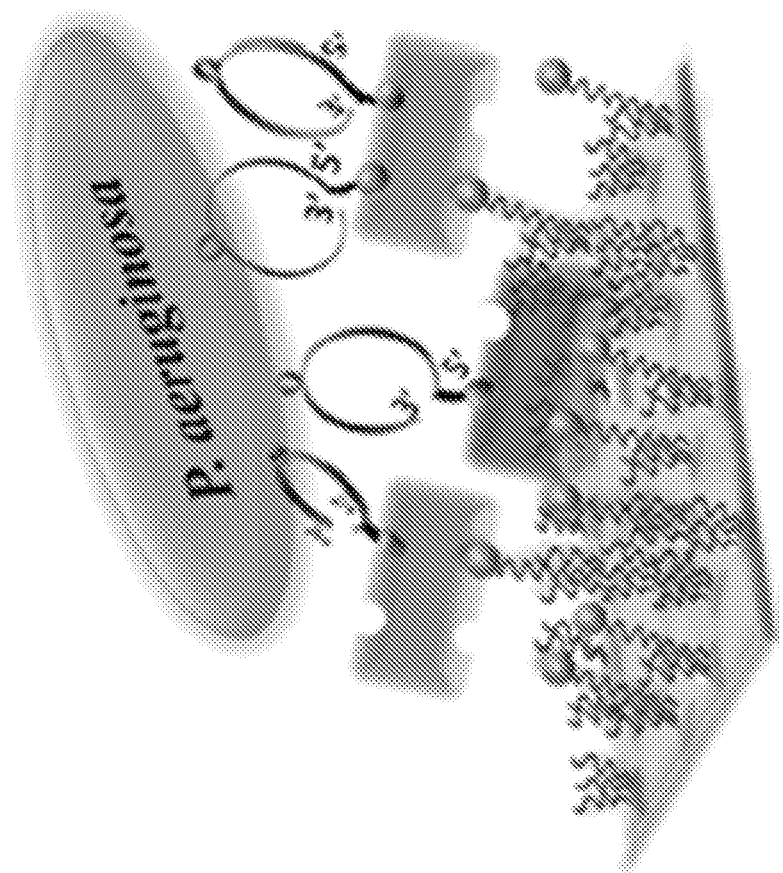
Figure 1B:
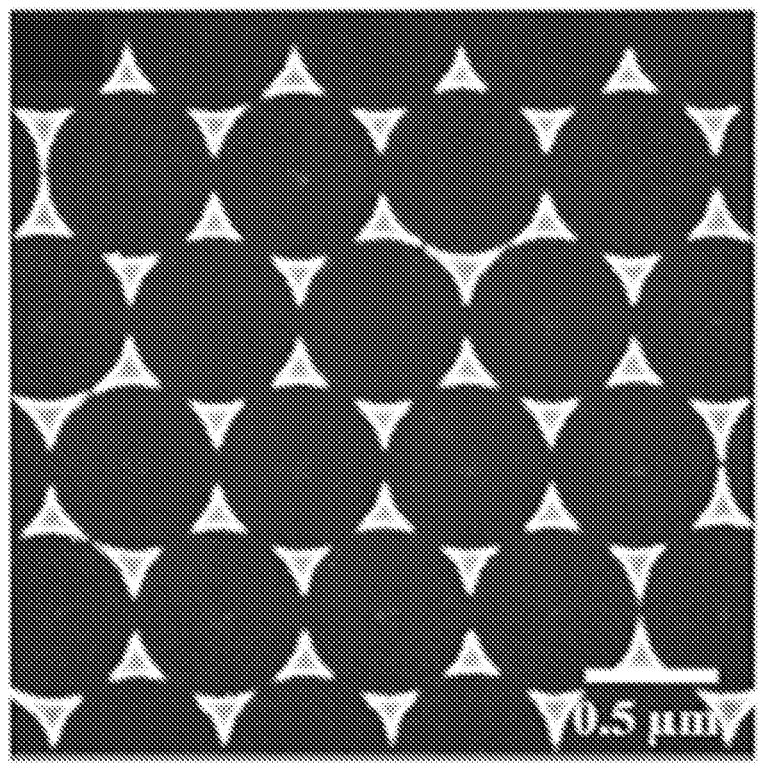
Figure 6A:
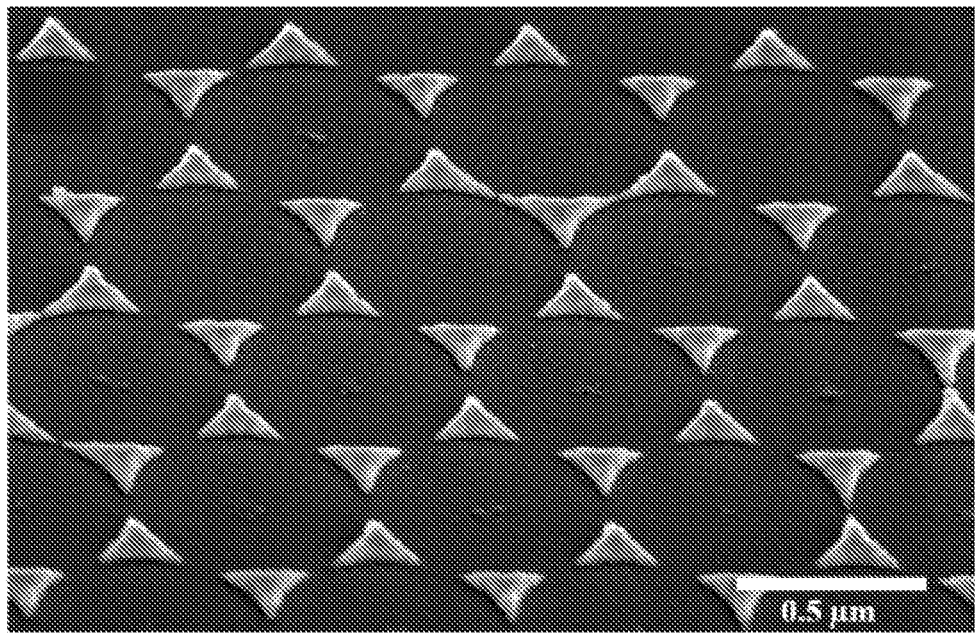
FIG. 6A is a plan view SEM image of the tilted nanotriangle LSPR array.
Figure 6B:
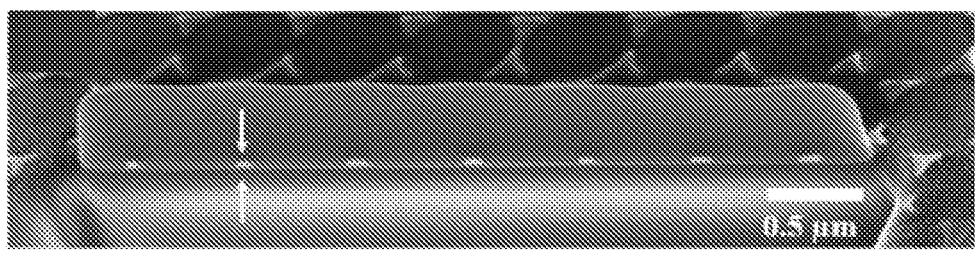
FIG. 6B is a cross-sectional SEM image of the same array showing the height of the triangular Au nanoparticles (white arrows).

A schematic illustration of a Au nanotriangle array, its layer-by-layer surface construction, and the bacterial detection scheme are shown in FIG. 1A. NSL was used to fabricate Au nanotriangle arrays on glass, as shown in FIG. 1B. Au nanotriangles with in-plane width of 210.5±9.1 nm, out-of-plane height of 47.6±0.4 nm, interparticle distance of 121.3±7.7 nm, and a truncated tetrahedral shape were obtained. SEM images of tilted and dissected Au nanotriangle arrays are shown in FIG. 6A and FIG. 6B, respectively.

Figure 1C:
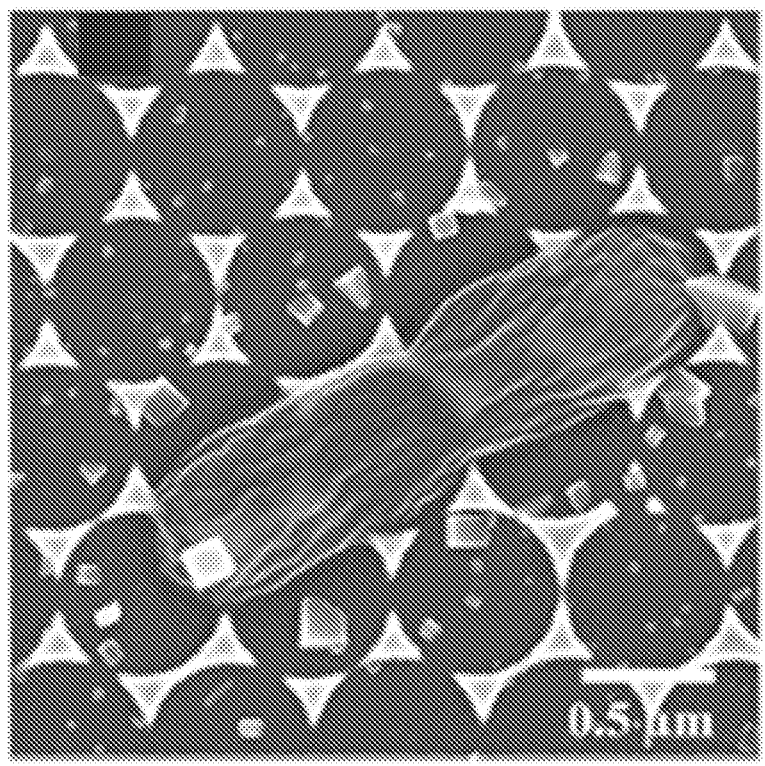

Au nanotriangle arrays were modified by self-assembly of (1:3) Bt-PEG thiol: PEG thiol directly onto the Au surface of the nanotriangles. Tetrameric neutravidin (NA) was then linked to the surface bound biotin through its strong non-covalent interaction ($K_a \sim 10^{13}$ $M^{-1}$). PEG thiol was specifically chosen to repel nonspecifically adsorbed molecules and bacteria. The molecular weight difference between Bt-PEG thiol (MW 1000 Da) and PEG thiol (MW 500 Da) results in different chain lengths, facilitating the longer chain Bt-PEG thiol in its function to capture NA. The 1:3 (v:v) ratio (Bt-PEG thiol:PEG thiol) was selected, after careful optimization experiments, shown in FIG. 7, to maximize PAO1 binding onto the surface while minimizing steric hindrance between affinity reagents. Subsequently, biotinylated aptamer (Bt-aptamer) was introduced to the neutravidin-modified sensor surface in order to provide a capture agent for *P. aeruginosa*. This aptamer sequence was previously selected against fixed *P. aeruginosa* ($K_d$=17.27±5.00 nM) using whole-cell SELEX. The sensor surface was then exposed to inactivated bacteria, which were pulled down from solution by the surface-immobilized aptamers. The maximum amount of neutravidin and aptamer immobilized on the sensor surface was estimated to be $8.5 \times 10^{12}$ $cm^{-2}$ and $1.7 \times 10^{13}$ $cm^{-2}$, respectively. A representative SEM image of a captured *P. aeruginosa* cell is shown in FIG. 1C. The binding of aptamer and *P. aeruginosa* cells was verified using confocal fluorescence microscopy. A fluorescence image and an overlaid image of fluorescence and transmission of 6FAM-labeled aptamer bound to *P. aeruginosa* are shown in FIG. 8A and FIG. 8B, respectively.

Example 3

Characterization of LSPR Measurements in Buffer and Air—Aptamer Based Biosensor

UV-visible extinction spectroscopy has been used to characterize LSPR resonances of Au nanoparticles both in solution and on surfaces and has been used to study molecular interactions at surfaces based upon LSPR wavelength shifts upon binding. It is well established that the refractive index of the surrounding environment affects the wavelength of the LSPR. To ascertain the optimal conditions for the aptamer-based assays, the sensitives of LSPR measurements in liquid (buffer) and air were compared by measuring the LSPR wavelength shift ($\Delta\lambda$) at several points in the assembly and capture process in both PBS and air. Measurements after immobilization of Bt-PEG thiol/PEG thiol, neutravidin, and Bt-aptamer onto the Au nanotriangle array, shown in FIG. 9, produced larger LSPR shifts in air than in PBS.

Furthermore, in the bacterial pull-down experiment, bacteria could not be detected at low PAO1 concentrations ($10^3$ cfu $mL^{-1}$) in PBS, a small LSPR wavelength shift being detected only at $10^7$ cfu $mL^{-1}$, FIG. 10 and Table 1. These results can be understood based on the larger refractive index difference between air (n~1.0) and bacterial cell (n~1.4) compared to replacement of buffer (n~1.35) with the same bacterium. The presence of bacteria on the sensor surface was verified by SEM images (data not shown). In addition, the variability of LSPR measurements made in PBS, FIG. 11 and Table 2, was significantly higher than those made in air. Thus, given the statistically significant differences in both sensitivity and experimental precision, all LSPR measurements were carried out in air.

TABLE 1

Student's t-test comparing LSPR wavelength shift in PBS as a function of PAO1 concentration.

| t - values[a] | Control vs. PAO1 ($1.0 \times 10^3$ cfu $mL^{-1}$) | Control vs. PAO1 ($1.0 \times 10^7$ cfu $mL^{-1}$) |
|---|---|---|
| $t_{expt}$ | 0.4 | 4.4 |
| $t_{0.999}$ $_{v=17(18)}$ | 3.97 | 3.92 |

[a] v = 17 for $10^3$ cfu $mL^{-1}$; v = 18 for $10^7$ cfu $mL^{-1}$

TABLE 2

F-test results for LSPR measurements performed in PBS and air.

| F - values | PBS vs. Air |
|---|---|
| $F_{expt}$ | 5.7 |
| $F_{0.95}$ 8.8 | 3.44 |

Example 4

Characterization of *P. aeruginosa*-Derived LSPR Shifts—Aptamer Based Biosensor

Figure 2:
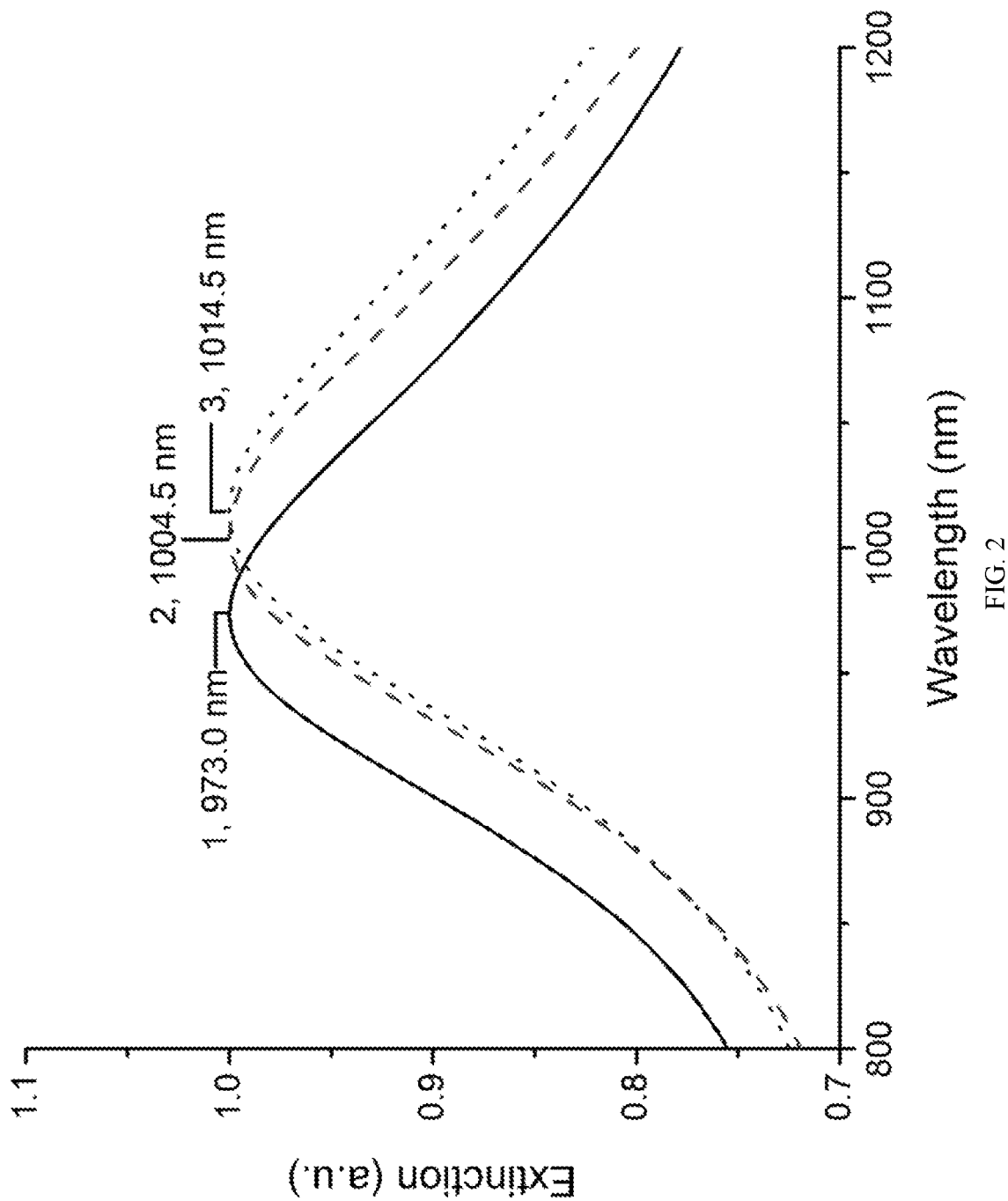

Here, bacterial pull-down was monitored by careful measurements of the UV-visible extinction spectrum. Care was taken to perform the measurements under controlled humidity conditions because the LSPR sensor chips are potentially sensitive to humidity and temperature. FIG. 2 shows representative extinction spectra of a bare Au nanotriangle array (curve 1), a Bt-PEG thiol/PEG thiol (1:3), neutravidin, and Bt-aptamer modified Au nanotriangle array (curve 2), and the same array after exposure to a solution containing 10 cfu $mL^{-1}$ *P. aeruginosa* (curve 3). Originally, the extinction maximum of the bare Au nanotriangle array was measured at 973.0 nm. Upon surface modification, the LSPR extinction maximum shifted to 1004.5 nm, i.e., $\Delta\lambda$=31.5 nm, indicating successful surface modification. Once bacteria were captured on the sensor surface, the LSPR peak red-shifted again to 1014.5 nm, an additional $\Delta\lambda$=10 nm. Although the specific shifts varied from sample to sample, the general pattern of successive red-shifts upon exposure, first to capture motif, then to target bacteria, was uniformly observed, FIGS. 12A-C.

When exposing the sensor surface to bacteria, it is important to simultaneously minimize salt crystal formation and avoid lysis of surface bound bacteria. When dried, salt crystals on sensor surfaces, FIG. 13A, can contribute to an apparent LSPR wavelength shift, thus confounding the bacterial-derived signal. In addition, lysis of bacteria, FIG.

13B, could give rise to LSPR signals not correlated with the number of bacteria present in the sample. Thus, substantial effort was devoted to identifying conditions sufficiently stringent to minimize salt crystal formation, yet gentle enough to leave surface-captured bacteria intact. On the basis of extensive optimization experiments, the following protocol was identified. After 1 h incubation with bacteria, sensor chips were washed three times with PBS for 5 min each to remove unbound bacteria, followed by water immersion for 30 s. All sensor chips were gently dried using $N_2$ gas for 5 min after the washing steps. This combination proved to be a good compromise capable of removing the majority of salts without causing bacterial lysis, FIG. 13C.

Example 5

Sensitivity Evaluation—Aptamer Based Biosensor

The sensitivity of sensor chips was evaluated by exposing them to various concentrations of *P. aeruginosa* and monitoring the LSPR wavelength shift ($\Delta\lambda$). Before evaluating sensitivity, it is important to understand the various contributions to sample-to-sample variability, which were compared using interbatch and intrabatch variability. Each batch consisted of a microscope slide diced into six small pieces: one chip as a control and the other five chips for testing separate bacterial samples. Each bacterial concentration was studied with 9-14 replicates. The interbatch variation was tested using two (or three in the case of 10 cfu mL$^{-1}$) microscope slides fabricated in different batches but exposed to the same bacterial concentration. The interbatch variation was analyzed using the difference of means, which ranged from 0.2-4.0 nm (FIG. 14). The small variation indicates that sensor chip fabrication process is reproducible, bacterial preparation protocol is reliable, and batch-to-batch variation is minimal. Intrabatch variation ranged from 1.3-5.5 nm, in statistical agreement with the interbatch measurements, as expected. However, the intrabatch variation was found to increase with increasing bacterial load. Because the number of binding sites grossly exceeds the bacterial load, bacterial binding on the sensor surface is a rare event, which can be described by a Poisson distribution, for which the variance and mean are equal.

Figure 3:
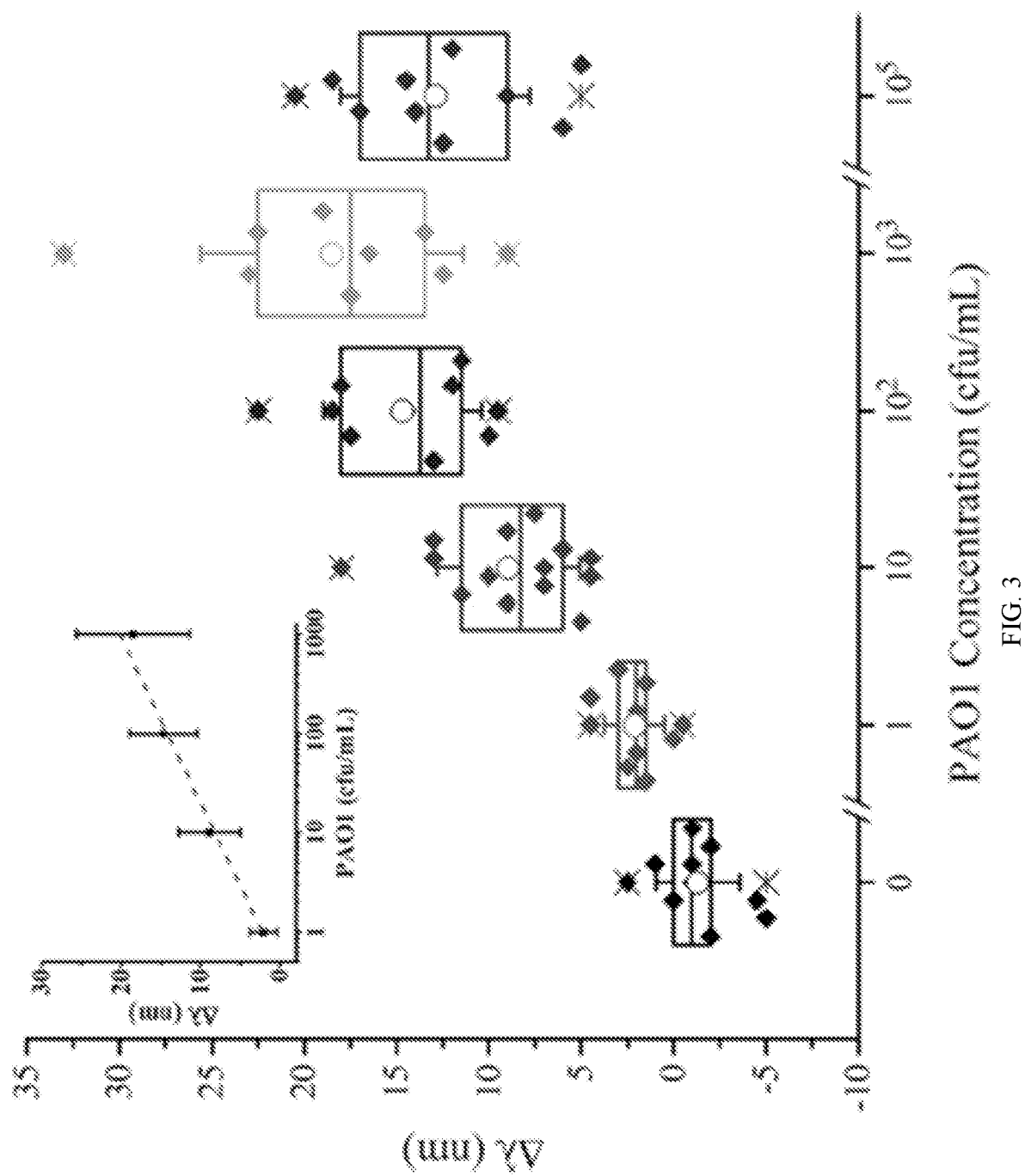

FIG. 3 shows the magnitude of LSPR wavelength shift ($\Delta\lambda$) as a function of bacterial concentration from 0 to $10^5$ cfu mL$^{-1}$. In contrast to other surface-based LSPR bacterial sensing studies, a correlation between the magnitude of the LSPR wavelength shift and log bacterial concentration was observed with a limit of detection (LOD) of 10 cfu mL$^{-1}$ *P. aeruginosa*, a level at which the expectation loading at the sensor surface is (n)=1 bacterium. Control experiments (0 cfu mL$^{-1}$) showed no statistically significant response compared to the unexposed pull-down surface, with a wavelength shift $\Delta\lambda=-1.3\pm2.3$ nm. Experiments performed at the ultralow surface bacterial loading ((n)=0.1) of 1 cfu mL$^{-1}$ resulted in a wavelength shift of $\Delta\lambda=2.1\pm1.7$ nm, not statistically distinguishable from the control, as expected.

Single bacterium experiments performed at 10 cfu mL$^{-1}$ gave rise to a wavelength shift of =8.9±3.9 nm, which is statistically different than the control and the 1 cfu mL$^{-1}$ result at the 99.9% confidence level. This exquisite sensitivity may originate from: (i) the inherent sensitivity of the LSPR sensor responding to small refractive index changes near the Au nanotriangle array surface, combined with the relatively thin capture layer which brings bacteria closer to the LSPR sensing volume, or (ii) a single bacterial cell on surface could distort local electric field around Au nanotriangles and provided an extraordinarily large signal. The LSPR wavelength shift saturated at concentrations higher than $10^3$ cfu mL$^{-1}$, although as suggested by the inset FIG. 3, bacterial samples in the 10-$10^3$ cfu mL$^{-1}$ can all be distinguished both from the control and the 1 cfu mL$^{-1}$ result at the 99.9% confidence level. Saturation of the LSPR signal at the relatively small loading of $10^3$ cfu mL$^{-1}$ is consistent with the extraordinary LOD observed and suggests mechanisms which enhance the LSPR response in the proximity of whole cell bacteria.

Example 6

Selectivity Evaluation—Aptamer Based Biosensor

Figure 4:
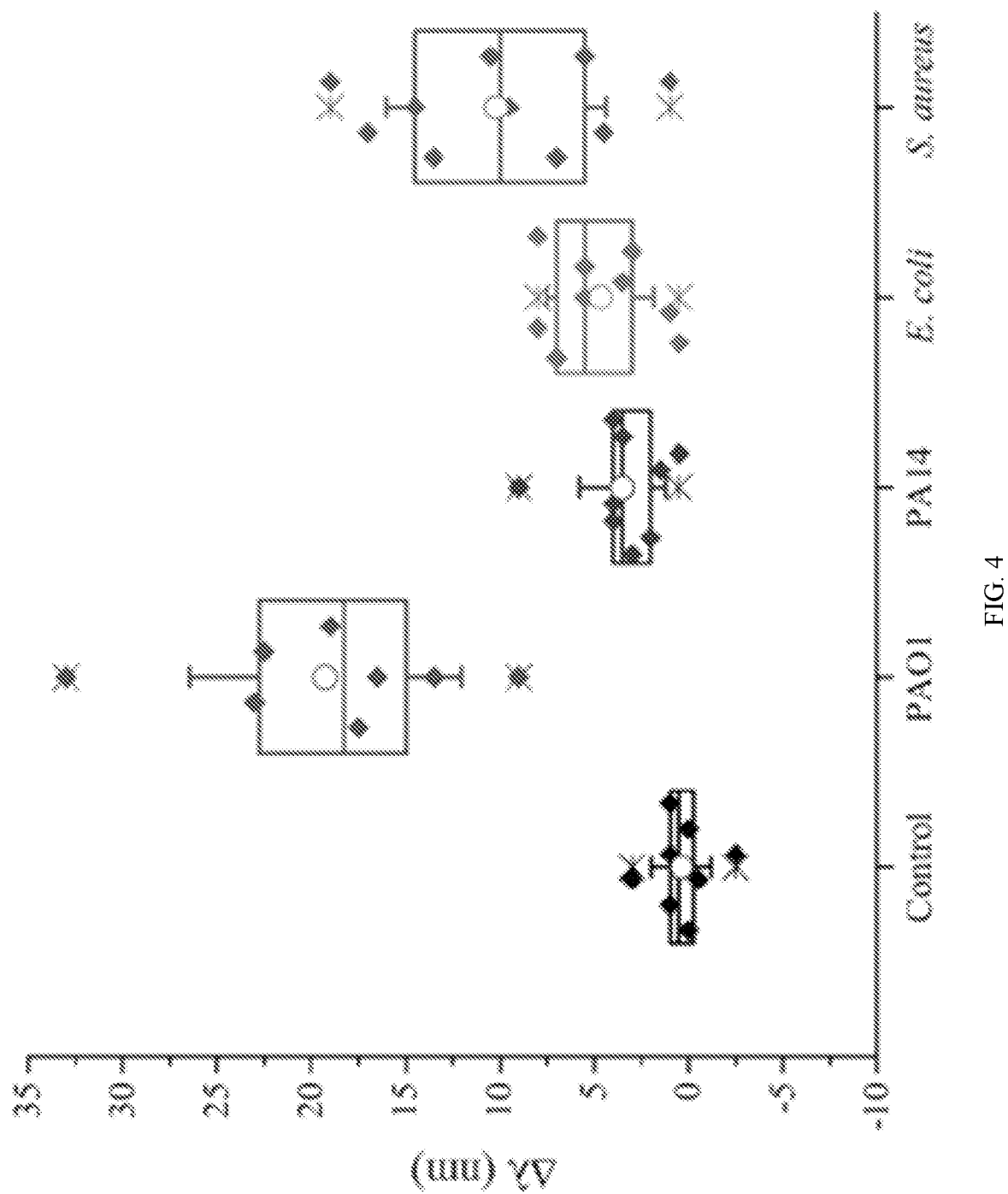

LSPR-based sensors are not inherently selective; their selectivity comes from the choice of affinity reagent, in the present case, an aptamer specially selected to recognize fixed *P. aeruginosa* cells. Very few *Pseudomonas*-specific aptamer sequences are available, and the aptamer used in this study was previously identified by selection against inactivated *P. aeruginosa* using whole-cell SELEX, although the molecular nature of the interaction between the aptamer and the *P. aeruginosa* cell envelope has not been delineated. The selectivity of the aptamer was tested with two different strains of *P. aeruginosa* (PAO1, PA14), *E. coli* DH5α, and *S. aureus* RN4220 using the LSPR-based sensing platform. All four bacteria were harvested in the exponential growth phase (FIG. 15). FIG. 4 shows that bacterial binding to sensor surfaces resulted in average LSPR wavelength shifts of 0.4±1.6, 19.3±7.2, 3.5±2.3, 4.7±2.8, and 10.2±5.8 nm for control, PAO1, PA14, *E. coli*, and *S. aureus*, respectively. The Student's t-test (Table 3) shows that there is a significant difference between PAO1 and control, PA14, and *E. coli* at the 99.9% confidence level, as well as a significant difference between PAO1 and *S. aureus* at the 99% confidence level. These results indicate that this aptamer has strong affinity to the PAO1 strain of *Pseudomonas* and negligible affinity to PA14 and *E. coli*, indicating that overall the aptamer is specific to recognizing *P. aeruginosa* strain PAO1. The specificity of the aptamer for PAO1 over *S. aureus* is somewhat lower. Noting that *S. aureus* exhibits different morphology than *Pseudomonas*, the wavelength-shift sensitivity to spherical *S. aureus*, viz. FIG. 16, may differ from the rod-shaped *Pseudomonas* and *E. coli*. In addition, some cross-reactivity may arise from *S. aureus* surface binding motifs that are inherently cross-reactive with the *Pseudomonas* aptamer. The selectivity of the sensor chip may be improved by: (1) using a modified SELEX process to identify an aptamer with higher specificity, and (2) changing the geometry of the nanotriangles to minimize sensitivity to spherical bacteria. In addition, the clinical and environmental potential of this LSPR sensing platform may be expanded by applying it to different samples, for example, environmental isolates and clinical samples at various stages of infection, e.g., planktonic vs. biofilm. Such samples will provide the impetus for screening new aptamers, from which a potential library can be developed.

TABLE 3

Student's t-test for aptamer selectivity

| t - values vs. PAO1[a] | Control | PA14 | *E. coli* | *S. aureus* |
|---|---|---|---|---|
| $t_{expt}$ | 7.3 | 6.6 | 5.6 | 3.0 |
| $t_{0.999(0.99)}$[v] | 4.14 | 4.02 | 4.07 | 2.92 |

[a]t-value for *S. aureus* at 99% level, others 99.9%; v = 14 (control); 16 (PA14 and *S. aureus*); 15 (*E. coli*)

Example 7

Stability Evaluation—Aptamer Based Biosensor

Figure 5:
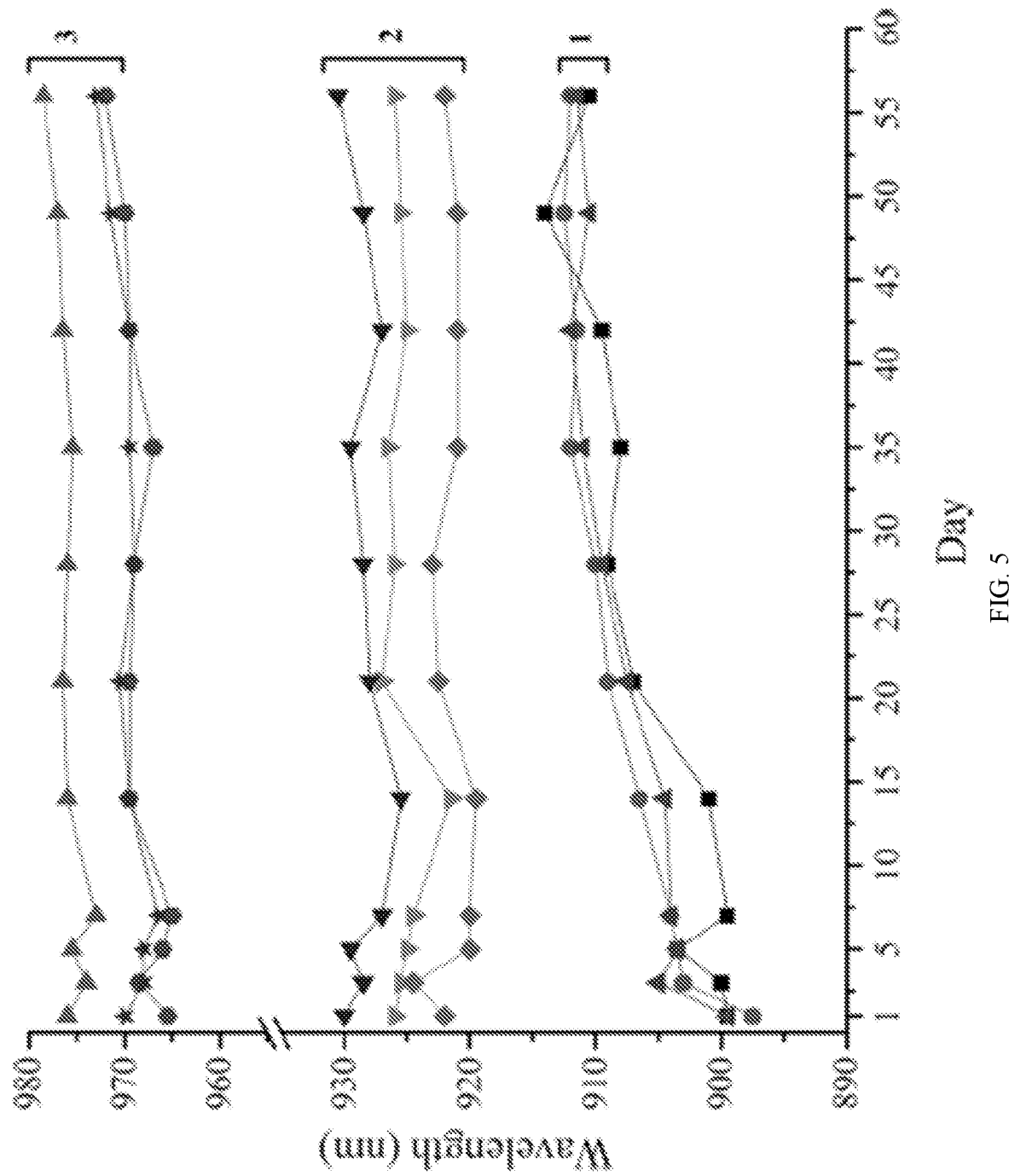

The stability of the sensor chip in ambient conditions is important to its potential use in the field and in point-of-care applications. An ideal sensor chip would be stable over a wide range of temperatures and humidities for a long period of time. In this study, the stability of unmodified, Bt-PEG thiol/PEG thiol (1:3), and Bt-PEG thiol/PEG thiol (1:3)/neutravidin modified sensor chips was monitored for 2 months in ambient conditions by following the shifts in the extinction maxima. FIG. 5 shows the temporal evolution of LSPR signals arising from unmodified Au nanotriangle arrays (group 1), arrays with Bt-PEG thiol/PEG thiol (1:3) (group 2), and arrays with subsequent modification of Bt-PEG thiol/PEG thiol (1:3) with neutravidin (group 3). Each set was tested using three different sensor chips. Comparing day 1 to day 56, the LSPR wavelength shifts observed for groups 1-3 were 12.5±1.8, 0.2±0.3, and 4.0±2.2 nm, respectively. Overall, sensor chips coated with Bt-PEG thiol/PEG thiol with or without neutravidin were significantly more stable than unmodified Au nanotriangles, and both were observed to be stable in ambient conditions for at least 2 months. Additionally, all sensor chips, including the unmodified surface, were stable for at least 2 months when stored in $N_2$ environment. The stability of these surface modified sensor chips in ambient conditions suggests the possibility of mass production and long-term storage of these sensor chips for field and clinical applications.

An LSPR sensing platform was developed for the detection of whole-cell microorganisms, using *P. aeruginosa* strain PAO1 as a model system. The sensor chip was designed to pull down whole-cell *P. aeruginosa* cells from solution via a surface confined aptamer. Capture of bacteria was monitored through the resulting red-shift in wavelength of the LSPR extinction maximum. This LSPR whole-cell microbial sensing platform is (a) rapid (~3 h), (b) highly sensitive, down to the level of a single bacterium, (c) selective against other strains of *Pseudomonas* and *E. coli*, and (d) stable in ambient conditions for >2 months. The general whole-cell LSPR sensing scheme demonstrated here could be translated to the detection of other microorganisms, including other bacteria as well as viruses, by switching affinity agents. This robust LSPR sensing platform has the potential to be used in clinical diagnostics and therapeutics, including in-the-field detection and point-of-care applications.

Example 8

Materials and Methods—Siderophore Based Biosensor

Materials: PEG thiol (MW 550 Da) was purchased from Creative PEGWorks. Biotin PEG thiol (MW 1000 Da) was purchased from Nanocs. NeutrAvidin Protein and formaldehyde (16% w/v aqueous solution, methanol-free) were purchased from Thermo Fisher Scientific. HOOK™ Biotin-PEG3-Amine was purchased from GBiosciences. Iron (III) acetylacetonate (Fe(acac)$_3$, 99.9% trace metals basis), 2,2'-bipyridyl, tris(2-carboxyethyl)phosphine hydrochloride powder, isobutyl chloroformate (ClCO$_2$i-Bu), tetrahydrofuran (THF), polystyrene beads (0.6 µm mean particle size), N-methylmorpholine, Mueller Hinton Broth, sodium phosphate monobasic monohydrate, sodium phosphate dibasic, ammonium phosphate dibasic, sulfuric acid (95.0 to 98.0%), hydrogen peroxide (30% w/w in H$_2$O), dimethyl sulfoxide (DMSO), and ethyl alcohol (200 proof) were all purchased from Sigma-Aldrich. Glass microscope slides (3×1") were purchased from Ted Pella. Micro cover glass (No. 1, 18 mm×18 mm) was purchased from VWR. Lysogeny broth and granulated agar were purchased from BD Difco. Deionized (DI) water was generated using a Milli-Q Gradient water purification system (Millipore, 18.2 MΩ·cm at 25° C.). Sterile 10 mM sodium phosphate buffer (pH 7.5) was used in all experiments. Tetrahydrofuran (THF) was freshly distilled over sodium before use. All other chemicals were used as received.

Siderophore Synthesis. All reactions were conducted under an atmosphere of dry argon unless otherwise stated. The mixed-ligand siderophore 1 (Schematic 1) was prepared. Specifically, to a cooled (0° C., ice-salt bath) solution of the penta-acetylated siderophore 1 (73 mg, 0.078 mmol) in anhydrous THF (1.5 mL) was added N-methylmorpholine (10.30 µL, 0.094 mmol, 1.2 equiv.) followed by isobutyl chloroformate (12.2 µL, 0.094 mmol, 1.2 equiv.). A white precipitate formed gradually after addition of the chloroformate (N-methylmorpholine hydrochloride salt). The reaction mixture was stirred at 0° C. and the progress of the isobutyl chloroformate ester formation was monitored by thin-layer chromatography (TLC) analysis. After 1 hour, TLC showed complete consumption of starting siderophore 1. The reaction mixture was filtered through a plug of cotton and rinsed with anhydrous THF (0.5 mL) to obtain a clear solution of the mixed anhydride of 1.

To conjugate PEG and biotin to the siderophore 1, the following procedures were carried out. In a separate round-bottom flask, biotin-PEG-amine (25 mg, 0.060 mmol, 0.77 equiv.) was added into a cooled (0° C., ice-salt bath) solution of sodium bicarbonate (15.7 mg, 0.187 mmol, 2.4 equiv.) in distilled DI water (2 mL). The mixed anhydride 1 was added to the resulting solution in a dropwise fashion over a period of 5 min. The reaction mixture was then stirred for 3 h at 0° C. (ice-salt bath). The coupling reaction progress, as indicated by the consumption of the biotin-PEG-amine, was monitored by reverse phase TLC and LC-MS analysis. The organic layer was separated, washed with brine, and concentrated to obtain the desired PEG-biotinylated siderophore as a mixture of products. The mixture was then purified by reverse phase chromatography (C18) using a gradient of CH$_3$CN/H$_2$O (20% to 70%) to obtain the desired biotinylated siderophore 2 (Schematic 1) as the major component. The minor components resulted from the loss of one (M-OAc), two (M-2OAc), three (M-3OAc) or four (M-4OAc) acetyl groups, and were also characterized by LC-MS analysis.

Preparation of 0.01 mg/mL Biotinylated Siderophore Solution. Biotinylated siderophore (Bt-siderophore) freezer stock (1 mg/mL) was prepared by dissolving 1.4 mg of synthesized Bt-siderophore into a mixture of 5% DMSO and 95% phosphate buffer saline solution to reach a final volume of 1.4 mL. Small aliquots of Bt-siderophore solution (0.01 mg/mL) were prepared by adding a 15 µL of Bt-siderophore (1 mg/mL) into a 74 µL of DMSO and a 1411 µL of 10 mM sodium phosphate solution. The small aliquots were mixed thoroughly and stored at −80° C. Each aliquot of Bt-siderophore solution (0.01 mg/mL) was slowly thawed at room temperature prior to use.

Preparation of Mueller-Hinton (MH) Iron Deficient Media. Mueller-Hinton (MH) media was prepared by dissolving 10.5 g of MH powder in 0.5 L of DI water. The MH media was autoclaved and cooled to room temperature. 2,2'-bipyridyl solution (1 mg/mL, 1 mL) was added into a 40 mL of cooled MH media. The MH media containing 2,2'-bipyridyl (MH iron deficient media) was stored at room temperature for at least 2 weeks prior to use, allowing 2,2'-bipyridyl to completely chelate environmental Fe (III) in solution and resulting in an iron deficient media.

Bacterial Cell Culture and Counting. *Acinetobacter baumannii* ATCC 17961 was obtained from Professor M. Miller's laboratory (University of Notre Dame). *Pseudomonas aeruginosa* strain PAO1, *Escherichia coli* DH5α, *Bacillus cereus*, and *Staphylococcus aureus* RN4220 were obtained from Professor J. Shrout's laboratory (University of Notre Dame). All bacteria were streaked from −80° C. freezer stocks and grown on lysogeny broth (LB) agar plates in a 37° C. incubator for 17 h. Liquid cell cultures were grown in MH iron deficient media. Specifically, cell cultures were first grown in a glass tube containing 6 mL of MH iron deficient media for 9 h in a 37° C. incubator with shaking at 240 rpm. Nine-hour bacterial cultures (30 μL) were removed and added to glass tubes containing 6 mL of MH iron deficient media. Diluted bacterial samples were grown at 37° C. for 12 h with shaking at 240 rpm prior to harvest. Cell cultures were washed twice using 10 mM sodium phosphate solution by centrifuging at 1000×G for 5 min each, and finally resuspended in sodium phosphate solution. The optical density of the resuspended cell culture was measured at 600 nm ($OD_{600}$) and adjusted to 0.80. Serial dilutions were then performed using 10 mM sodium phosphate buffer to achieve desired bacterial concentrations. Diluted bacterial samples were used immediately.

Standard microbiology plating and counting methods were used to correlate bacterial cell density (cfu $mL^{-1}$) to optical density ($OD_{600}$). Specifically, the optical density of all bacterial solution was adjusted to 0.80 after resuspending bacteria in a 10 mM sodium phosphate solution. *A. baumannii*, *P. aeruginosa*, and *E. coli* solutions were diluted 6 orders of magnitude in a 10 mM sodium phosphate solution, while *B. cereus* solution was diluted 5 orders of magnitude due to the difference in cell density according to our preliminary studies. Diluted bacterial solution (100 μL) was added onto an LB agar plate and spread using a metal spreader, which was sterilized by dipping in ethanol and flamed before and after each use. The bacterial containing LB agar plates were incubated at 37° C. overnight, and colonies were counted the next day. Final bacterial cell density was calculated by averaging the colony counts from 9 LB agar plates (3 plates were prepared in one experiment, and the same experiment was repeated 3 times on different days). At $OD_{600}$ of 0.80, there are $0.4 \times 10^9$, $1.1 \times 10^9$, $0.5 \times 10^9$, and $0.1 \times 10^9$ cfu $mL^{-1}$ of *A. baumannii*, *P. aeruginosa*, *E. coli*, and *B. cereus*, respectively.

LSPR Sensor Chip Fabrication. LSPR sensor chips were fabricated via NSL. Briefly, glass microscope slides were immersed in piranha solution (Cation: piranha, a strong oxidizer, contains sulfuric acid/hydrogen peroxide in a 3:1 v/v and should be handled with extreme caution!) overnight, rinsed, and stored in DI water. Polystyrene (PS) beads were first diluted in ethanol (1:2 v/v) and well mixed. A monolayer of diluted PS beads was spread at an air-water interface and transferred onto a clean microscope slide by emersion through the interface. PS bead-coated glass slides were dried at 60° C., and then coated with Cr (1 nm) and Au (50 nm) using an electron beam deposition (UNIVEX 450B, Oerlikon). Metal coated glass slides were sonicated in chloroform for 15 min to remove the PS beads, resulting in a hexagonal nanoscale array of Au trigonal prisms on glass, and then rinsed with DI water, dried with $N_2$ gas, and stored under $N_2$ environment. A dicing saw (Disco DAD3240) equipped with a diamond blade (Thermocarbon) was used to cut each Au-patterned glass slide (76.2 mm×25.4 mm) into six individual sensor chips (10.16 mm×15.24 mm). All sensor chips were subsequently sonicated in ethanol and DI water for 5 min each, rinsed with DI water, dried with $N_2$ gas, and stored under $N_2$ environment prior to use.

Sensor Surface Modification. Each sensor chip was modified with a mixture of Bt-PEG thiol (1 mM) and PEG thiol (1 mM) in a 1:3 v/v ratio for 16 h with mild shaking. A volume of 0.2 mL of NeutrAvidin (1 mg/mL), Bt-siderophore (0.01 mg/mL), and $Fe(acac)_3$ (1 mM) were subsequently incubated on the sensor surface for 0.5 h in a humidity-controlled environment with mild shaking. Sensor chips were rinsed with DI water and dried with $N_2$ gas after each surface modification step. $Fe(acac)_3$ solution was freshly prepared in 1% of DMSO and 9% of 10 mM ammonium phosphate dibasic solution (pH 8) prior to each experiment.

Bacterial Binding and Fixation. Bacterial binding experiments were carried out by adding 0.2 mL of bacterial solution at the desired concentration onto the siderophore-Fe (III) modified sensor chips. The bacterial solution used for all experiments contained bacteria in 10 mM sodium phosphate buffer. Control chips were exposed to 0.2 mL of 10 mM sodium phosphate solution. These sensor chips were incubated in a 37° C. incubator for 1 h in a humidity controlled environment, allowing bacteria to recognize and bind to surface-confined siderophore-Fe (III) complexes. To remove unbound bacterial cells, the solution on the sensor chips was gently decanted, and the sensor chips were then washed three times in 10 mM sodium phosphate (5 min per wash). To inactivate surface bound bacterial cells, 200 μL of 6% formaldehyde solution was added to the bacteria-containing sensor chips and incubated at 37° C. for 1 h in a humidity controlled environment. After 1 h cell fixation, the solution on the sensor chips was gently decanted, and the sensor chips were then washed in three times 10 mM sodium phosphate solution (5 min per wash), followed by a DI water wash for 30 s. Sensor chips containing bound inactivated bacteria were gently dried with $N_2$ gas for 5 min prior to characterization.

Characterization. A UV-visible-NIR spectrometer (Jasco V-670) with a 60 mm integrating sphere (Jasco ISN-723) was used to acquire LSPR spectra. Each spectrum was an average of three spectral accumulations from 600-1400 at 0.5 nm interval. All extinction spectra were normalized. The probe beam size was ca. 8 mm×9 mm. Scanning electron microscope images of a bare sensor chip (i.e., nanoscale Au trigonal prism arrays) and a modified sensor chip with captured *A. baumannii* cells were acquired using a field-emission scanning electron microscope (FEI Magellan 400) at 5.00 kV. To avoid surface charging, a thin layer of iridium (2.0 nm) was sputtered on the substrate prior to imaging.

Liquid chromatography-mass spectrometry (LC-MS) was used to characterize both the freshly synthesized biotinylated siderophore (Bt-siderophore) and the Bt-siderophore in a buffer solution. In general, a UPLC system, autosampler, and photodiode array detector (Dionex Ultimate 3000) were coupled to a quadrupole time-of-flight hybrid mass spectrometer (Bruker MicrOTOF-Q II). Analytes were separated using a Thermo Scientific Acclaim™ RSLC 120 C18 column (2.2 μm particle size, 120 Å pore size, 2.1 mm inner diameter, 100 mm length) with a mobile phase composed of either A=0.1% formic acid in water or B=0.1% formic acid in acetonitrile. The samples were eluted at 0.4 mL/min with a mobile phase gradient of (i) 90% A/10% B for 2 min, (ii) 0% A/100% B for 18 min, (iii) 90% A/10% B for 2 min. For the freshly synthesized Bt-siderophore, the eluted samples were ionized in positive ion mode using a Bruker electrospray ionization source (end plate offset voltage=−500 V, capillary voltage=2200 V, $N_2$ as a nebulizer at 5 bar and a dry gas at 10.0 L/min flow rate at 220° C.). Mass spectra were acquired over a mass range of 50-3000 Da. For the Bt-siderophore in buffer, the eluted samples were ionized in positive ion mode using a Bruker electrospray ionization source (end plate offset voltage=−500 V, capillary voltage=2400 V, $N_2$ as a nebulizer at 4 bar and a dry gas at 7.0 L/min flow rate at 180° C.). Mass spectra were acquired at 5000 scans/s over a mass range of 300-3000 Da. Hystar 3.2 software was used in both data analyses.

Thin layer chromatography of freshly synthesized biotinylated siderophore. Sorbent Technologies silica gel 60 (32-63 μm) was used for all silica gel column chromatography purifications. Reverse phase chromatographic purifications were performed on Teledyne Instruments' 30 gram RediSep Rf Gold® C18Aq reversed-phase columns (column volume: 26.4 mL, average particle size: 20-40 average pore size: 100 Å) at a flow rate of 35 mL/min. Thin layer chromatography (TLC) was performed with Al-backed Merck 60-F254 or Al-backed Merck RP-C18 F256 silica gel plates using a 254 nm lamp and aqueous $FeCl_3$ for visualization.

Example 9

Siderophore Synthesis and Characterization

The key molecular recognition motif, a biscatecholate-monohydroxamate mixed ligand siderophore with three polyethylene glycol (PEG) repeating units linked to a biotin (Bt) (Compound 2, Schematic 1) was synthesized as described above. Briefly, the penta acetyl-protected glutaryl siderophore 1 was converted to the corresponding chloroformate active ester by treatment with isobutyl chloroformate ($ClCO_2$i-Bu) in the presence of N-methylmorpholine (NMM) in THF at 0° C. The chloroformate ester formation was considered complete when TLC analysis showed complete consumption of the starting siderophore 1. The PEG-Bt-siderophore, 2, was obtained by coupling the mixed anhydride to the biotin-PEG-amine in aqueous bicarbonate, and purified using reverse phase chromatography C18 columns with a gradient of $CH_3CN/H_2O$. LC-MS analysis of the freshly synthesized biotinylated siderophore showed a major component and four minor components. The minor components resulted from the loss of one (M-OAc), two (M-2OAc), three (M-3OAc), and four (M-4OAc) acetyl groups. Just prior to bacterial binding experiments, the biotinylated siderophore in buffer was also characterized using LC-MS.

The LC-MS analysis of the freshly synthesized biotinylated siderophore showed that there were a major component and four minor components in the synthesized biotinylated siderophore 2 (Schematic 1). The major component, $[m+2H]^{2+}$ calculated for $C_{63}H_{91}N_9O_{21}S$, had a m/z value of 671.8110, which matched to its theoretical value (671.8098). The minor components resulted from the loss of one (M-OAc), two (M-2OAc), three (M-3OAc), and four (M-4OAc) acetyl groups. The experimental and theoretical m/z values of these minor components were: 650.8031 and 650.8045 for $[m+2H]^{2+}$ calculated for $C_{61}H_{89}N_9O_{20}S$ (M-OAc), 629.8050 and 629.7992 for $[m+2H]^{2+}$ calculated for $C_{59}H_{87}N_9O_{19}S$ (M-2OAc), 608.7950 and 608.7939 for $[m+2H]^{2+}$ calculated for $C_{57}H_{85}N_9O_{18}S$ (M-3OAc), as well as 587.7968 and 587.7887 for $[m+2H]^{2+}$ calculated for $C_{55}H_{83}N_9O_{17}S$ (M-4OAc). Additionally, LC-MS analysis of the biotinylated siderophore in buffer (FIG. 22) revealed five components: (1) siderophore-Fe (III) complex without biotin, (2) and (3) two unknown iron complexes, (4) siderophore with neither biotin nor Fe (III), and (5) biotinylated siderophore without acetate. The Fe (III) observed in this analysis was from the environment, e.g., buffer, since no iron was intentionally added to the sample. Among these five components, only the biotinylated siderophore (~58% abundance) without acetate functions as a competent affinity reagent.

Schematic 1. Synthesis of biotinylated siderophore (conjugate 2) by coupling of the mixed anhydride of siderophore 1 and biotin PEG3 amine.

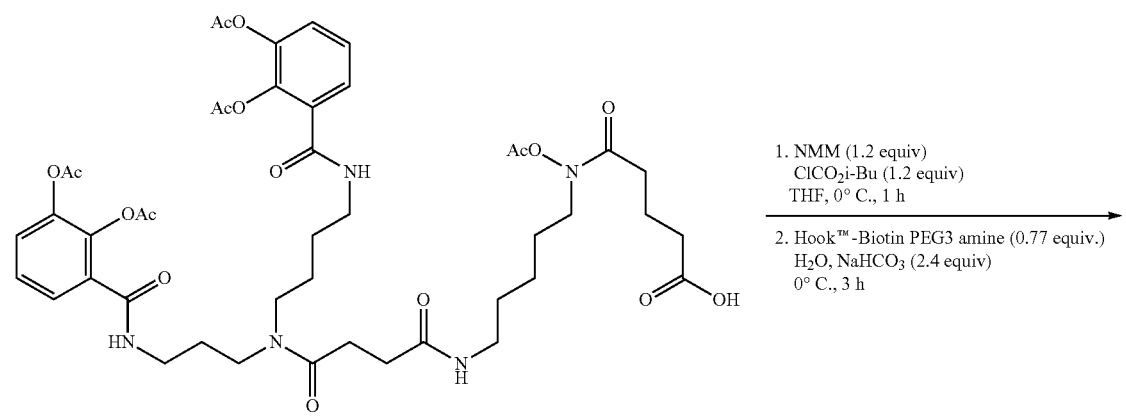

-continued

2

Sensor Chip Fabrication and Sensor Surface Modification. A schematic illustration of the siderophore-based whole-cell LSPR sensor chip is shown in FIG. 17A. The sensor chip, a microscope slide patterned with a hexagonal array of nanoscale Au trigonal prisms, was fabricated using NSL. A representative SEM image of a bare sensor chip is shown in FIG. 17B. Detailed dimensional analysis of a typical sensor chip revealed in-plane width, 210.5±9.1 nm, out-of-plane height, 47.6±0.4 nm, and tip-to-tip distance, 121.3±7.7 nm, of the trigonal prisms.

The sensor surface was first modified with a mixture of Bt-PEG thiol (1000 Da) and PEG thiol (550 Da) in a 1:3 v/v ratio via self-assembly. The PEG thiol, used to prevent nonspecific adsorption, has a shorter chain length than the Bt-PEG thiol used to anchor subsequent surface immobilized moieties. The 1:3 ratio was determined previously to produce maximum bacterial binding on the sensor surface. Tetrameric NeutrAvidin, with two biotin binding sites each on opposite sides of the protein, was subsequently immobilized onto the biotin modified sensor surface via the strong non-covalent biotin-NeutrAvidin linkage. Specifically, the affinity equilibrium constant, Ka, of NeutrAvidin for surface immobilized biotin is ~5.5×10$^{11}$M$^{-1}$. NeutrAvidin, a deglycosylated avidin, was chosen over avidin and streptavidin due to its similar biotin-binding affinity, more neutral isoelectric point (pI 6.3), as well as its lower tendency for nonspecific binding.

The Bt-siderophore, 2, was subsequently immobilized onto NeutrAvidin modified sensor surface as an affinity reagent to pull-down *A. baumannii*. The demonstrated selectivity and potency recommend this siderophore as a promising affinity reagent. In order to be recognized and utilized by bacteria, a siderophore has to chelate Fe (III) to form a siderophore-Fe (III) complex presumably in a 1:1 ratio. Thus, Fe(acac)$_3$ was subsequently introduced to the Bt-siderophore modified sensor surface as an additional iron source to saturate surface-bound siderophore. Bacteria-containing solutions were then exposed to the siderophore-Fe (III) modified sensor surface. A representative SEM image of surface captured *A. baumannii* cells is shown in FIG. 17C.

Example 10

Characterization of *A. baumannii*-Derived LSPR Wavelength Shift

LSPR spectroscopy was used to characterize surface modifications and bacterial binding. Representative NIR extinction spectra of a bare sensor chip (curve 1), a modified sensor chip (curve 2), and a sensor chip with captured bacteria (curve 3) are shown in FIG. 18. The bare sensor chip containing an array of nanoscale Au trigonal prisms exhibited an LSPR extinction maximum at 904.0 nm, which was red-shifted to 928.5 nm, i.e., $\Delta\lambda$=24.5 nm, after surface modification with Bt-PEG thiol/PEG thiol, NeutrAvidin, Bt-siderophore, and Fe(acac)$_3$. Once *A. baumannii* (4×10$^6$ cfu mL$^{-1}$) in 10 mM sodium phosphate solution was captured, the LSPR extinction maximum was further red-shifted to 941.5 nm, i.e., $\Delta\lambda$=13.0 nm. Despite differences in the initial LSPR extinction maximum among different unmodified sensor chips, red-shifts upon surface modification, as well as bacterial capture, were consistent across all experiments.

Figure 23:
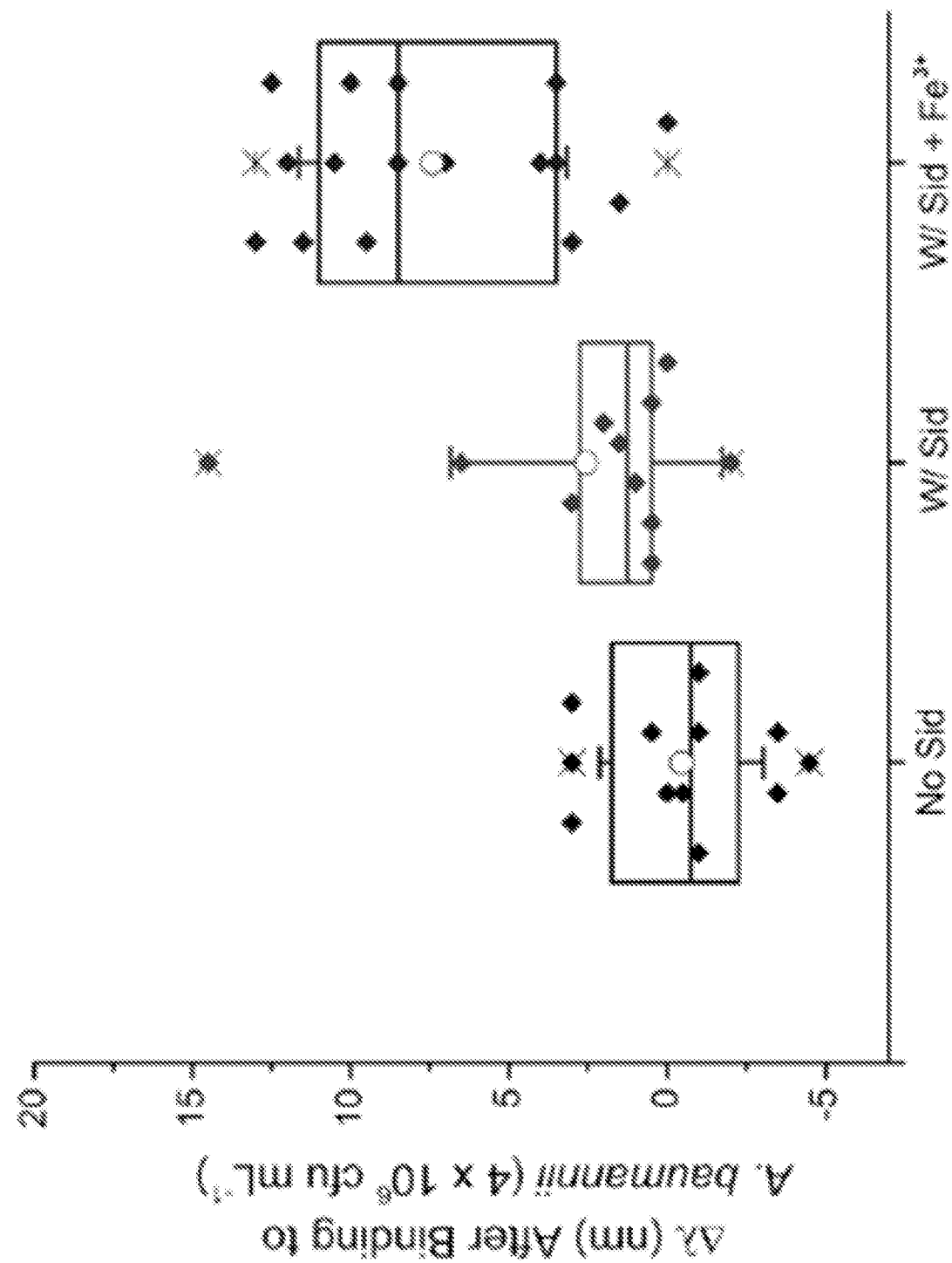

Control Experiments. Various control experiments were carried out to investigate the role of both Bt-siderophore and externally added Fe (III) source in *A. baumannii* binding experiments. FIG. 23 shows a mean LSPR wavelength shift ($\Delta\lambda$) of −0.5±2.6, 2.5±4.3, and 7.4±4.2 nm resulting from binding *A. baumannii* (4×10$^6$ cfu mL$^{-1}$) in 10 mM sodium phosphate solution at three different surface modification stages: after addition of Bt-PEG thiol/PEG thiol and NeutrAvidin (black), further modification with Bt-siderophore (red), and after exposure to Fe(acac)$_3$ (blue), respectively. Each of these conditions was tested using 13-17 individual sensor chips. Without Bt-siderophore and Fe (III), no *A. baumannii* binding signal was observed, indicating a negligible amount of non-specific interaction between bacteria and the NeutrAvidin modified sensor surface. Immobilizing the Bt-siderophore, but without additional Fe (III), again produced a minimal amount of bacterial binding signal. This observation suggests that even though surface confined Bt-siderophore may chelate trace amounts of adventitious environmental Fe (III) the resulting surface bound siderophore-Fe (III) complex is not sufficient to disrupt the measurement. Finally, a large *A. baumannii* binding signal was observed after supplying additional Fe (III) to the Bt-siderophore modified sensor surface in a 1:1 molar ratio. Interestingly, no additional binding resulted from a surface prepared with a 10-fold excess of Fe(acac)$_3$ (LC-MS data not shown). Thus, a 1:1 molar ratio of Bt-siderophore and Fe(acac)$_3$ was chosen for all following experiments.

Example 11

Sensitivity Evaluation—Siderophore Based Biosensor

Figure 22:
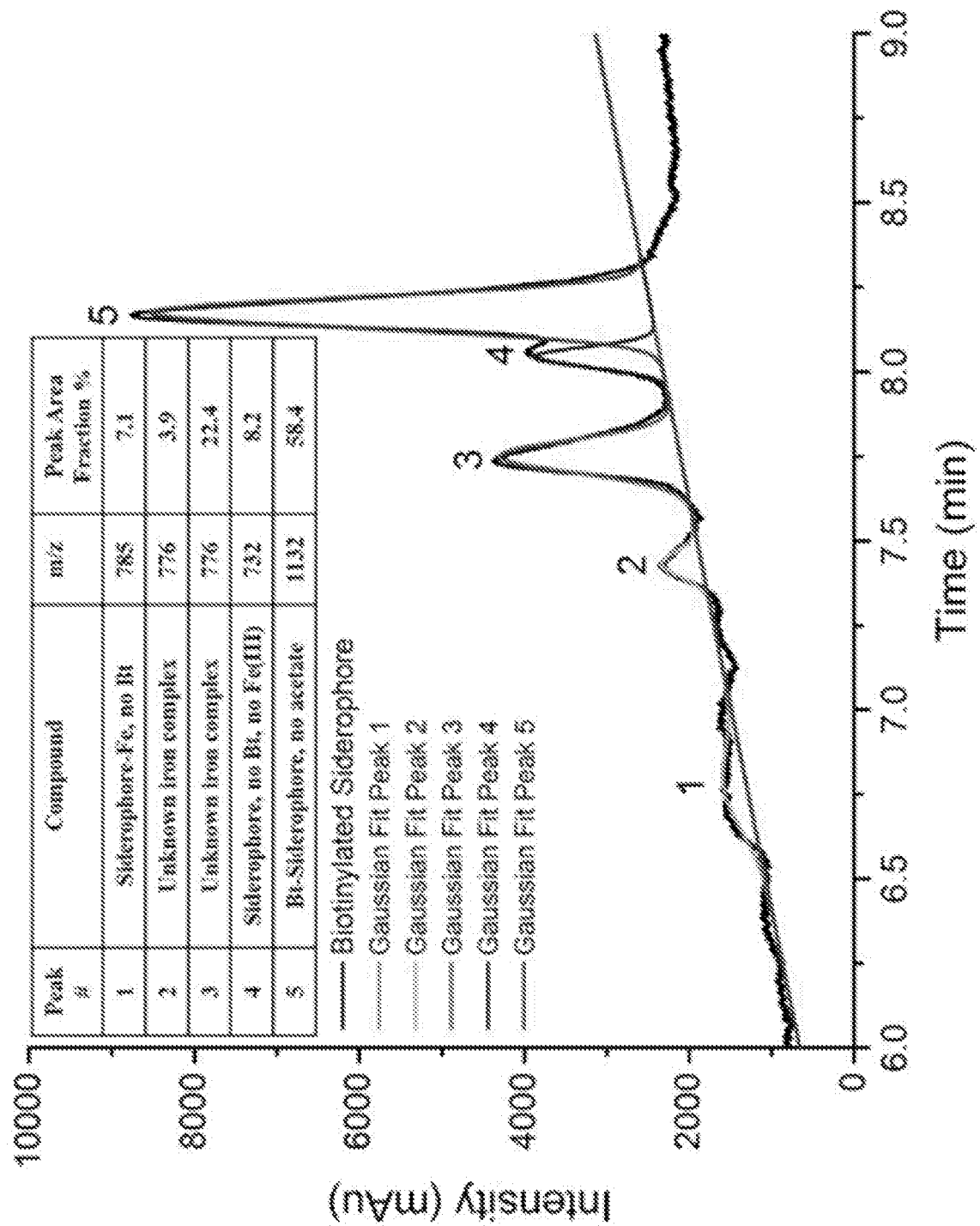

The sensitivity of the siderophore biosensor was investigated as a function of *A. baumannii* concentration ranging from $4\times10^2$ to $4\times10^6$ cfu mL$^{-1}$ in 10 mM sodium phosphate solution, with each bacterial concentration being tested using 10-17 individual sensor chips. The mean LSPR wavelength shift ($\Delta\lambda$) was measured to be 2.9±2.0 to 7.4±4.2 nm across this range, with the control sample showing −0.9±2.4 nm (FIG. 19). FIG. 19 inset shows that the siderophore biosensor exhibits a linear LSPR wavelength shift in log bacterial concentration. Using the Student's t-test, the difference between control (0 cfu mL$^{-1}$) and lowest test concentration ($4\times10^2$ cfu mL$^{-1}$) establishes that the two can be discriminated at the 99.9% confidence level, thereby setting the LOD at 400 cfu mL$^{-1}$, which is equivalent to the active sensor area being exposed to 80 *A. baumannii* cells. However, because the actual number of cells resident on the sensor chip surface at the LOD condition is not known, 80 cells is an upper bound. The batch-to-batch variation in the production of sensor chips was shown to be minimal in a previous study. However, there may be variations in the near-field distribution produced by the heterogeneity in the gold trigonal prism array. Thus, the measurement variability may arise from a combination of near-field and biological variation. The siderophore-based sensor characterized here exhibits a higher LOD (80 bacterial cells) than a similar LSPR biosensor for *P. aeruginosa* (LOD~1 cell) employing an aptamer molecular recognition agent described herein, which can plausibly be attributed to: (a) differing native affinities for the target; (b) differing availability of the transporter protein due to steric hindrance; (c) differing magnitude of the alteration in the near-surface refractive index profile, n(z); and/or impurities in the formulation, as indicated in the LC-MS analysis of the biotinylated siderophore (FIG. 22). Nevertheless, compared to other biosensors targeting *A. baumannii*, the LOD of 400 cfu mL$^{-1}$ compares quite favorably.

Example 12

Selectivity Evaluation—Siderophore Based Biosensor

Selective detection of the target analyte is a crucial figure of merit for biosensors. The selectivity of the siderophore biosensor was assessed against both Gram-negative (*Acinetobacter baumannii* ATCC 1796, *Pseudomonas aeruginosa* strain PAO1, *E. coli* DH5α) and Gram-positive bacteria (*Bacillus cereus*). All four bacteria were grown in an iron deficient media, and bacterial concentrations were adjusted to ~$10^7$ cfu mL$^{-1}$ in 10 mM sodium phosphate solution. Control experiments were carried out using 10 mM sodium phosphate solution without bacteria. *S. aureus*, another Gram-positive bacterium, was tested but is not included in this study due to its inability to grow in the iron deficient media. FIG. 20 shows the LSPR wavelength shift corresponding to different bacterial binding to the siderophore-Fe (III) modified sensor surface. Specifically, mean LSPR wavelength shifts of −0.9±2.4, 7.4±4.2, 0.5±2.8, 1.8±2.1, and 0.8±1.3 nm were observed from the control, and from *A. baumannii, P. aeruginosa, E. coli,* and *B. cereus*, respectively. The Student's t-test shows there is a significant difference in LSPR wavelength shift between *A. baumannii* and control (no bacteria), *P. aeruginosa, E. coli,* and *B. cereus* at the 99.9% confidence level. These results demonstrate that the Bt-siderophore has a high affinity for *A. baumannii* and a negligible affinity towards *P. aeruginosa, E. coli,* and *B. cereus*. The demonstrated selectivity of the Bt-siderophore offers an exciting opportunity to identify *A. baumannii* from a mixture of different bacteria and to expand the possibility of detecting *A. baumannii* infection in clinical settings. Table 4 shows a Student's t-test for siderophore selectivity.

TABLE 4

| Siderophore Selectivity | | | | |
|---|---|---|---|---|
|  | Control[b] | *P. aeruginosa* | *E. coli* | *B. cereus* |
| $t_{exp}$ (t-values calculated against *A. baumannii*[a]) | 5.63 | 4.85 | 4.19 | 5.21 |
| $t_{0.999}^v$ | 3.75 | 3.71 | 3.71 | 3.71 |

[a] t-value for all bacteria at a 99.9% confidence level; n = 16 (*A. baumannii*); 10 (control); 12 (*P. aeruginosa, E. coli,* and *B. cereus*).
[b] Control sample presents the siderophore surface recognition agent, but has not been exposed to bacteria.

Stability. Biosensor stability over a wide range of conditions (e.g., temperature, humidity) is important for applications, especially in resource limited settings. To test the stability of our siderophore biosensor, the siderophore-Fe (III) modified sensor chips were stored in ambient conditions and their LSPR wavelength shifts were monitored every week for a month. FIG. 21 shows the LSPR wavelength difference between day 0 and day x, where x=7, 14, 21, and 30. The observed mean LSPR wavelength shifts from 12 individual sensor chips were 0.1±1.3, 1.5±1.2, 2.4±1.4, and 4.0±1.8 nm after 7, 14, 21, and 30 days, respectively. The shifts at 7 and 14 days are not statistically significant relative to the control, indicating that siderophore-Fe (III) modified sensor chips are stable in ambient conditions for up to 2 weeks. The small, but monotonic, shift in extinction maximum likely arises from changes in composition and/or structure of the Au trigonal prisms, e.g. due to surface contamination.

Versatility. The utility of the whole-cell LSPR sensing approach was extended in this study using the novel siderophore bacterial pull-down strategy. Results from these two systems suggest that the whole-cell LSPR sensing platform is versatile and could be extended to a wide range of super-molecular analytes (e.g., bacteria, viruses, fungi) by swapping target-specific affinity reagents. Thus, the whole-cell bacterial pull-down biosensor offers the opportunity to expand the diagnostic tool box for use against infectious agents.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

EMBODIMENTS

For reasons of completeness, various aspects of the present disclosure are set out in the following numbered embodiments:

Embodiment 1

A biosensor for detection of analytes, the biosensor comprising:
a. an array of gold nanoparticles;
b. biotinylated polyethylene glycol thiol in direct contact with one or more of the gold nanoparticles;
c. polyethylene glycol thiol in direct contact with one or more of the gold nanoparticles;
d. at least one neutravidin molecule immobilized on a surface of the biotinylated polyethylene glycol thiol; and
e. at least one affinity reagent immobilized on a surface of the at least one neutravidin molecule.

Embodiment 2

The biosensor of embodiment 1, wherein the array of gold nanoparticles comprises gold nanotriangles.

Embodiment 3

The biosensor of embodiment 1 or 2, wherein the biosensor comprises a hexagonal array of gold nanoparticles.

Embodiment 4

The biosensor of any one of embodiments 1-3, wherein the biosensor comprises biotinylated polyethylene glycol thiol and polyethylene glycol thiol in a ratio of about 1:3 by volume.

Embodiment 5

The biosensor of any one of embodiments 1-4, wherein the affinity reagent is a biotinylated aptamer.

Embodiment 6

The biosensor of embodiment 5, wherein the biotinylated aptamer selectively binds *Pseudomonas aeruginosa*.

Embodiment 7

The biosensor of embodiment 6, wherein the biotinylated aptamer selectively binds *Pseudomonas aeruginosa* strain PAO1.

Embodiment 8

The biosensor of embodiment 7, wherein the biotinylated aptamer is encoded by the nucleotide sequence of SEQ ID NO: 1.

Embodiment 9

The biosensor of any one of embodiments 1-4, wherein the affinity reagent is a biotinylated siderophore.

Embodiment 10

The biosensor of embodiment 9, wherein the biotinylated siderophore is a biscatecholate-monohydroxamate mixed ligand siderophore.

Embodiment 11

The biosensor of embodiment 10, wherein the biscatecholate-monohydroxamate mixed ligand siderophore comprises three repeating polyethylene glycol units linked to a biotin molecule.

Embodiment 12

The biosensor of any one of embodiments 9-11, wherein the biotinylated siderophore selectively binds *Acinetobacter baumannii*.

Embodiment 13

A method of detecting one or more whole bacterial cells in a sample, the method comprising contacting the sample with the biosensor of any one of embodiments 1-12.

Embodiment 14

A method of detecting a bacterial infection in a subject, the method comprising:
a. obtaining a sample from the subject;
b. contacting the sample with a biosensor, wherein the biosensor comprises
  i. an array of gold nanoparticles;
  ii. biotinylated polyethylene glycol thiol in direct contact with one or more of the gold nanoparticles;
  iii. polyethylene glycol thiol in direct contact with one or more of the gold nanoparticles;
  iv. at least one neutravidin molecule immobilized on a surface of the biotinylated polyethylene glycol thiol; and
  v. at least one affinity reagent immobilized on a surface of the at least one neutravidin molecule;
c. detecting a localized surface plasmon resonance wavelength of the sample; and
d. comparing the localized surface plasmon resonance wavelength of the sample to a localized surface plasmon resonance wavelength in a control sample,
  wherein a shift in the wavelength of maximum extinction of the localized surface plasmon resonance of the sample relative to the wavelength of maximum extinction of the localized surface plasmon resonance of the control sample indicates a bacterial infection in the subject.

Embodiment 15

The method of embodiment 14, wherein the array of gold nanoparticles comprises gold nanotriangles.

Embodiment 16

The method of embodiment 14 or 15, wherein the biosensor comprises a hexagonal array of gold nanoparticles.

Embodiment 17

The method of any one of embodiments 13-16, wherein the biosensor comprises biotinylated polyethylene glycol thiol and polyethylene glycol thiol in a ratio of about 1:3 by volume.

Embodiment 18

The method of any one of embodiments 13-17, wherein the affinity reagent is a biotinylated aptamer.

Embodiment 19

The method of embodiment 18, wherein the biotinylated aptamer selectively binds Pseudomonas aeruginosa.

Embodiment 20

The method of embodiment 19, wherein the biotinylated aptamer selectively binds Pseudomonas aeruginosa strain PAO1.

Embodiment 21

The method of embodiment 20, wherein the biotinylated aptamer is encoded by the nucleotide sequence of SEQ ID NO: 1.

Embodiment 22

The method of any one of embodiments 13-17, wherein the affinity reagent is a biotinylated siderophore.

Embodiment 23

The method of embodiment 22, wherein the biotinylated siderophore is a biscatecholate-monohydroxamate mixed ligand siderophore.

Embodiment 24

The method of embodiment 23, wherein the biscatecholate-monohydroxamate mixed ligand siderophore comprises three repeating polyethylene glycol units linked to a biotin molecule.

Embodiment 25

The method of any one of embodiments 22-24, wherein the biotinylated siderophore selectively binds Acinetobacter baumannii.

Embodiment 26

The method of any one of embodiments 13-25, wherein a concentration of bacteria of about $4 \times 10^6$ cfu/mL or less produces a positive shift in the wavelength of maximum extinction of the localized surface plasmon resonance of the sample, indicating bacterial infection in the subject.

Embodiment 27

The method of any one of embodiments 13-26, wherein the method detects a bacterial infection in the subject in approximately 3 hours.

Embodiment 28

The method of any one of embodiments 13-27, wherein the bacterial infection in the subject is a Pseudomonas aeruginosa infection or an Acinetobacter baumannii infection.

---

SEQUENCE LISTING

Biotinylated aptamer
(SEQ ID NO: 1)
(Bt-aptamer, 5' [Bt]ATACCAGCTTATTCAATTCCCC
CGTTGCTTTCGCTTTTCCTTTCGCTTTTGTTCGTTTCGTCCCT
GCTTCCTTTCTTGAGATAGTAAGTGCAATCT3')

fluorescently labeled biotinylated aptamer
(SEQ ID NO: 2)
(6FAM-aptamer-Bt, 5' [6-carboxyfluorescein-
ATACCAGCTTATTCAATTCCCCCGTTGCTTTCGCTTTTCCTTTC
GCTTTTGTTCGTTTCGTCCCTGCTTCCTTTCTTGAGATAGTAAG
TGCAATCT-[Bt]3')

---

What is claimed is:

1. A biosensor for detection of analytes, the biosensor comprising:
   (a) an array of gold nanoparticles;
   (b) biotinylated polyethylene glycol thiol in direct contact with one or more of the gold nanoparticles;
   (c) polyethylene glycol thiol in direct contact with one or more of the gold nanoparticles;
   (d) at least one deglycosylated avidin molecule immobilized on a surface of the biotinylated polyethylene glycol thiol; and
   (e) at least one affinity reagent comprising a biotinylated aptamer encoded by a nucleotide sequence having at least 95% sequence identity to SEQ ID NO: 1, the affinity reagent being immobilized on a surface of the at least one deglycosylated avidin molecule.

2. The biosensor of claim 1, wherein the array of gold nanoparticles comprises gold nanotriangles.

3. The biosensor of claim 1, wherein the biosensor comprises a hexagonal array of gold nanoparticles.

4. The biosensor of claim 1, wherein the biosensor comprises biotinylated polyethylene glycol thiol and polyethylene glycol thiol in a ratio of about 1:3 by volume.

5. The biosensor of claim 1, wherein the biotinylated aptamer selectively binds *Pseudomonas aeruginosa*.

6. The biosensor of claim 5, wherein the biotinylated aptamer selectively binds *Pseudomonas aeruginosa* strain PAO1.

7. The biosensor of claim 1, wherein the biotinylated aptamer is encoded by the nucleotide sequence of SEQ ID NO: 1.

8. A method of detecting one or more whole bacterial cells in a sample, the method comprising:
   (i) contacting the sample with the biosensor of claim 1;
   (ii) detecting a localized surface plasmon resonance wavelength of the sample; and
   (iii) comparing the localized surface plasmon resonance wavelength of the sample to a localized surface plasmon resonance wavelength in a control sample, wherein a shift in the wavelength of maximum extinction of the localized surface plasmon resonance of the sample relative to the wavelength of maximum extinction of the localized surface plasmon resonance of the control sample indicates presence of one or more whole bacterial cells in the sample.

9. A method of detecting bacterial presence in a subject, the method comprising:
   (a) obtaining a sample from the subject;
   (b) contacting the sample with a biosensor, wherein the biosensor comprises:
      (i) an array of gold nanoparticles;
      (ii) biotinylated polyethylene glycol thiol in direct contact with one or more of the gold nanoparticles;
      (iii) polyethylene glycol thiol in direct contact with one or more of the gold nanoparticles;
      (iv) at least one deglycosylated avidin molecule immobilized on a surface of the biotinylated polyethylene glycol thiol; and
      (v) at least one affinity reagent comprising a biotinylated aptamer encoded by a nucleotide sequence having at least 95% sequence identity to SEQ ID NO: 1, the affinity reagent being immobilized on a surface of the at least one deglycosylated avidin molecule;
   (c) detecting a localized surface plasmon resonance wavelength of the sample; and
   (d) comparing the localized surface plasmon resonance wavelength of the sample to a localized surface plasmon resonance wavelength in a control sample, wherein a shift in the wavelength of maximum extinction of the localized surface plasmon resonance of the sample relative to the wavelength of maximum extinction of the localized surface plasmon resonance of the control sample indicates a bacterial presence in the subject.

10. The method of claim 9, wherein the array of gold nanoparticles comprises gold nanotriangles.

11. The method of claim 9, wherein the biosensor comprises a hexagonal array of gold nanoparticles.

12. The method of claim 9, wherein the biosensor comprises biotinylated polyethylene glycol thiol and polyethylene glycol thiol in a ratio of about 1:3 by volume.

13. The method of claim 9, wherein the biotinylated aptamer selectively binds *Pseudomonas aeruginosa*.

14. The method of claim 13, wherein the biotinylated aptamer selectively binds *Pseudomonas aeruginosa* strain PAO1.

15. The method of claim 9, wherein the biotinylated aptamer is encoded by the nucleotide sequence of SEQ ID NO: 1.

16. The method of claim 9, wherein a concentration of bacteria of about $4 \times 10^6$ cfu/mL or less produces a positive shift in the wavelength of maximum extinction of the localized surface plasmon resonance of the sample, indicating bacterial infection in the subject.

17. The method of claim 9, wherein the method detects a bacterial presence in the subject in approximately 3 hours.

18. The method of claim 16, wherein the bacterial infection in the subject is a *Pseudomonas aeruginosa* infection or an *Acinetobacter baumannii* infection.

* * * * *